(12) United States Patent
Waldraff et al.

(10) Patent No.: US 9,307,767 B2
(45) Date of Patent: Apr. 12, 2016

(54) HERBICIDALLY AND INSECTICIDALLY ACTIVE THIAZOLOPYRIDINONES

(71) Applicant: BAYER INTELLECTUAL PROPERTY GMBH, Monheim (DE)

(72) Inventors: Christian Waldraff, Bad Vilbel (DE); Stefan Lehr, Lyons (FR); Alfred Angermann, Kriftel (DE); Hansjoerg Dietrich, Liederbach am Taunus (DE); Jan Dittgen, Frankfurt (DE); Elmar Gatzweiler, Bad Nauheim (DE); Christopher Hugh Rosinger, Hofheim (DE); Angela Becker, Duesseldorf (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 14 days.

(21) Appl. No.: 14/386,155

(22) PCT Filed: Mar. 25, 2013

(86) PCT No.: PCT/EP2013/056311
§ 371 (c)(1),
(2) Date: Sep. 18, 2014

(87) PCT Pub. No.: WO2013/144096
PCT Pub. Date: Oct. 3, 2013

(65) Prior Publication Data
US 2015/0045217 A1    Feb. 12, 2015

(30) Foreign Application Priority Data
Mar. 27, 2012 (EP) .................. 12161413

(51) Int. Cl.
*A01N 43/90* (2006.01)
*C07D 513/04* (2006.01)

(52) U.S. Cl.
CPC ........... *A01N 43/90* (2013.01); *C07D 513/04* (2013.01)

(58) Field of Classification Search
CPC .................. A01N 43/90; C07D 513/04
See application file for complete search history.

(56) References Cited

U.S. PATENT DOCUMENTS 7,902,356 B2 *  3/2011  Amegadzie .......... C07D 513/04
                                                        544/105
8,686,000 B2 *  4/2014  Lehr ..................... C07D 231/40
                                                        514/301
2004/0087577 A1 *  5/2004  Pratt ..................... C07D 213/69
                                                        514/222.8

FOREIGN PATENT DOCUMENTS

WO       2011051212 A1    5/2011
WO    WO2011051212 A1 *  5/2011   ............ A01N 43/90
WO       2012028582 A1    3/2012
WO    WO2012028582 A1 *  3/2012   ............ C07D 471/04

OTHER PUBLICATIONS

International Search Report from corresponding PCT/EP2013/056311, mailed Jul. 9, 2013.
Wermuth, "Molecular Variations Based on Isosteric Replacements", The Practice of Medicinal Chemistry, ISBN 0-12-744640-0, 1996, pp. 203-237.

* cited by examiner

*Primary Examiner* — Jane C Oswecki
(74) *Attorney, Agent, or Firm* — MMWV IP, LLC

(57) ABSTRACT

Thiazolopyridinones of the general formula (I) are described as herbicides.

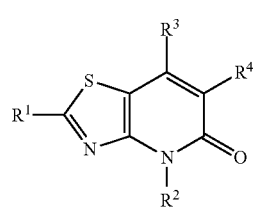

(I)

In this formula (I), $R^1$, $R^2$, $R^3$ and $R^4$ represent radicals such as hydrogen, organic radicals such as alkyl and other radicals such as halogen, nitro and cyano.

17 Claims, No Drawings

HERBICIDALLY AND INSECTICIDALLY ACTIVE THIAZOLOPYRIDINONES

CROSS REFERENCE TO RELATED APPLICATIONS

This application is a §371 National Stage Application of PCT/EP2013/056311, filed Mar. 25, 2013, which claims priority to EP 12161413.5, filed Mar. 27, 2012.

BACKGROUND

1. Field of the Invention

The invention relates to the technical field of herbicides and insecticides, especially that of herbicides for selective control of broad-leaved weeds and weed grasses and also for the control of insects in crops of useful plants.

Specifically, it relates to substituted pyridinone derivatives, to processes for their preparation and to their use as herbicides.

2. Description of Related Art

Various publications describe herbicidally active pyridinones which form a fused ring system with five- or six-membered heterocyclic rings. WO2011/051212 discloses pyridinones which are fused to selected five-membered heterocycles and which are substituted in the 3-position of the pyridine ring by aryl and heteroaryl radicals. WO 2012/028582 A1 discloses pyridinones which are fused to selected five- and six-membered heterocycles and which are substituted in the 3-position of the pyridine ring by aryl radicals.

The herbicidal activity of the compounds known from these publications, however, is frequently inadequate. Accordingly, it is an object of the present invention to provide further herbicidally active compounds.

SUMMARY

It has now been found that thiazolopyridinones substituted in the 3-position of the pyridine ring by specific aromatic radicals are particularly suitable as herbicides. The present invention thus provides diketopyridines of the formula (I) or salts thereof

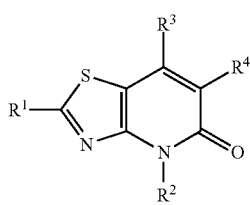
(I)

in which $R^1$ represents hydrogen, halogen, nitro, cyano, $(C_1-C_6)$-alkyl, $(C_2-C_6)$-alkenyl, $(C_2-C_6)$-alkynyl, $(C_1-C_6)$-alkoxy, $(C_1-C_6)$-alkylthio, $(C_1-C_6)$-alkylsulfinyl, $(C_1-C_6)$-alkylsulfonyl, $(C_3-C_6)$-cycloalkyl, $(C_1-C_6)$-alkoxy-$(C_1-C_6)$-alkyl, di-$(C_1-C_6)$-alkoxy-$(C_1-C_6)$-alkyl or $(C_1-C_6)$-alkylthio-$(C_1-C_6)$-alkyl, each of which is substituted by n halogen atoms, $R^2$ represents hydrogen, $(C_1-C_6)$-alkyl, $(C_2-C_6)$-alkenyl, $(C_3-C_6)$-alkynyl, $(C_3-C_6)$-cycloalkyl, $(C_1-C_6)$-alkoxy-$(C_1-C_6)$-alkyl or di-$(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_3-C_6)$-cycloalkyl-$(C_1-C_6)$-alkyl, cyano-$(C_1-C_6)$-alkyl, each of which is substituted by n halogen atoms, or phenyl or benzyl, each of which is substituted by n radicals from the group consisting of halogen, $(C_1-C_6)$-alkyl and $(C_1-C_6)$-alkoxy, $R^3$ represents hydroxy, O—C(=O)$R^7$, O—C(=L)M$R^8$, O—SO$_2R^9$, O—P(=L)$R^{10}R^{11}$, O—C(=L)N$R^{12}R^{13}$, O-E or O—$R^{14}$, $R^4$ represents $R^{4a}$ or $R^{4b}$, $R^{4a}$ represents aryl which is substituted by n radicals $R^5$ and one radical $R^6$, $R^{4b}$ represents 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-1-yl, 1,2,4-triazol-3-yl, 1,2,4-triazol-4-yl, 1,2,4-triazol-5-yl, 1,2,3-triazol-1-yl, 1,2,3-triazol-2-yl, 1,2,3-triazol-4-yl, tetrazol-1-yl, tetrazol-2-yl, tetrazol-5-yl, indol-1-yl, indol-2-yl, indol-3-yl, isoindol-1-yl, isoindol-2-yl, benzofur-2-yl, benzothiophen-2-yl, benzofur-3-yl, benzothiophen-3-yl, benzoxazol-2-yl, benzothiazol-2-yl, benzimidazol-2-yl, indazol-1-yl, indazol-2-yl, indazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl or 1,2,4-triazin-6-yl, each of which is substituted by n radicals $R^5$ and by m radicals $R^6$, $R^5$ represents hydrogen, halogen, nitro, cyano, $(C_1-C_6)$-alkyl, $(C_2-C_6)$-alkenyl, $(C_2-C_6)$-alkynyl, $(C_1-C_6)$-alkoxy, $(C_1-C_6)$-alkylthio, $(C_1-C_6)$-alkylsulfinyl, $(C_1-C_6)$-alkylsulfonyl, $(C_3-C_6)$-cycloalkyl, $(C_1-C_6)$-alkoxy-$(C_1-C_6)$-alkyl or $(C_1-C_6)$-alkylthio-$(C_1-C_6)$-alkyl, each of which is substituted by n halogen atoms, $R^6$ represents aryl or heteroaryl, each of which is substituted by s radicals $R^5$, E represents a metal ion equivalent or an ammonium ion, L represents oxygen or sulfur, M represents oxygen or sulfur, $R^7$ represents $(C_1-C_6)$-alkyl, $(C_2-C_6)$-alkenyl, $(C_1-C_6)$-alkoxy-$(C_1-C_6)$-alkyl, di-$(C_1-C_6)$-alkoxy-$(C_1-C_6)$-alkyl or $(C_1-C_6)$-alkylthio-$(C_1-C_6)$-alkyl, each of which is substituted by n halogen atoms, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, $(C_1-C_6)$-alkyl and $(C_1-C_6)$-alkoxy, or $(C_3-C_6)$-cycloalkyl, phenyl, phenyl-$(C_1-C_6)$-alkyl, phenoxy-$(C_1-C_6)$-alkyl or heteroaryloxy-$(C_1-C_6)$-alkyl, each of which is substituted by n radicals from the group consisting of halogen, $(C_1-C_6)$-alkyl and $(C_1-C_6)$-alkoxy, $R^8$ represents $(C_1-C_6)$-alkyl, $(C_2-C_6)$-alkenyl, $(C_1-C_6)$-alkoxy-$(C_1-C_6)$-alkyl or di-$(C_1-C_6)$-alkoxy-$(C_1-C_6)$-alkyl, each of which is substituted by n halogen atoms, or $(C_3-C_6)$-cycloalkyl, phenyl or benzyl, each of which is substituted by n radicals from the group consisting of halogen, $(C_1-C_6)$-alkyl and $(C_1-C_6)$-alkoxy, $R^9$, $R^{10}$, $R^{11}$ independently of one another represent $(C_1-C_6)$-alkyl, $(C_1-C_6)$-alkoxy, N—$(C_1-C_6)$-alkylamino, N,N-di-$(C_1-C_6)$-Alkylamino, $(C_1-C_6)$-alkylthio, $(C_2-C_6)$-alkenyl or $(C_3-C_6)$-cycloalkylthio, each of which is substituted by n halogen atoms, or phenyl, benzyl, phenoxy or phenylthio, each of which is substituted by n radicals from the group consisting of halogen, $(C_1-C_6)$-alkyl and $(C_1-C_6)$-alkoxy, $R^{12}$, $R^{13}$ independently of one another each represent hydrogen, $(C_1-C_6)$-alkyl, $(C_3-C_6)$-cycloalkyl, $(C_2-C_6)$-alkenyl, $(C_1-C_6)$-alkoxy or $(C_1-C_6)$-alkoxy-$(C_1-C_6)$-alkyl, substituted by n halogen atoms, phenyl or benzyl, each of which is substituted by n radicals from the group consisting of halogen, $(C_1-C_6)$-alkyl and $(C_1-C_6)$-alkoxy, or $R^{12}$ and $R^{13}$ together with the nitrogen atom to which they are attached form a 3- to 6-membered ring containing 2 to 5 carbon atoms and in each case 0 or 1 oxygen or sulfur atoms;

$R^{14}$ represents $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_1-C_6)$-alkylthio-$(C_1-C_6)$-alkyl or di-$(C_1-C_6)$-alkoxy-$(C_1-C_6)$-alkyl, each of which is substituted by n halogen atoms, $(C_3-C_6)$-cycloalkyl substituted by n radicals from the group consisting of halogen, $(C_1-C_6)$-alkyl and $(C_1-C_6)$-alkoxy, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, $(C_1-C_6)$-alkyl and $(C_1-C_6)$-alkoxy, phenyl, phenyl-$(C_1-C_6)$-alkyl, heteroaryl, phenoxy-$(C_1-C_6)$-alkyl or heteroaryloxy-$(C_1-C_6)$-alkyl, substituted by n radicals from the group consisting of halogen, $(C_1-C_6)$-alkyl and $(C_1-C_6)$-alkoxy, m represents 0 or 1,
n represents 0, 1, 2 or 3,
s represents 0, 1, 2, 3 or 4.

DETAILED DESCRIPTION OF A PREFERRED EMBODIMENT

Alkyl represents saturated straight-chain or branched hydrocarbyl radicals having 1 to 8 carbon atoms, for example $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Haloalkyl represents straight-chain or branched alkyl groups having 1 to 8 carbon atoms, where in these groups some or all of the hydrogen atoms may be replaced by halogen atoms, for example $C_1-C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Alkenyl represents unsaturated straight-chain or branched hydrocarbyl radicals having 2 to 8 carbon atoms and one double bond in any position, for example $C_2-C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl represents straight-chain or branched hydrocarbyl radicals having 2 to 8 carbon atoms and one triple bond in any position, for example $C_2-C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Alkoxy represents saturated straight-chain or branched alkoxy radicals having 1 to 8 carbon atoms, for example $C_1-C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, haloalkoxy represents straight-chain or branched alkoxy groups having 1 to 8 carbon atoms (as mentioned above), where in these groups some or all of the hydrogen atoms may be replaced by halogen atoms as mentioned above, for example $C_1-C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-,2-difluoroethoxy, 2,2-dichloro-2-fluoroethoxy, 2,2,2-trichloroethoxy, pentafluoroethoxy and 1,1,1-trifluoroprop-2-oxy.

Alkylthio represents saturated, straight-chain or branched alkylthio radicals having 1 to 8 carbon atoms, for example $C_1-C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio.

Haloalkylthio represents straight-chain or branched alkylthio groups having 1 to 8 carbon atoms (as mentioned above), where in these groups some or all of the hydrogen atoms may be replaced by halogen atoms as mentioned above, for example $C_1$-$C_2$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-,2-difluoroethylthio, 2,2-dichloro-2-fluoroethylthio, 2,2,2-trichloroethylthio, pentafluoroethylthio and 1,1,1-trifluoroprop-2-ylthio.

Aryl represents phenyl or naphthyl.

Heteroaryl represents in particular 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-1-yl, 1,2,4-triazol-3-yl, 1,2,4-triazol-4-yl, 1,2,4-triazol-5-yl, 1,2,3-triazol-1-yl, 1,2,3-triazol-2-yl, 1,2,3-triazol-4-yl, tetrazol-1-yl, tetrazol-2-yl, tetrazol-5-yl, indol-1-yl, indol-2-yl, indol-3-yl, isoindol-1-yl, isoindol-2-yl, benzofur-2-yl, benzothiophen-2-yl, benzofur-3-yl, benzothiophen-3-yl, benzoxazol-2-yl, benzothiazol-2-yl, benzimidazol-2-yl, indazol-1-yl, indazol-2-yl, indazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl or 1,2,4-triazin-6-yl. This heteroaryl is—unless stated otherwise—in each case unsubstituted or in each case mono- or polysubstituted by identical or different radicals selected from fluorine, chlorine, bromine, iodine, cyano, hydroxyl, mercapto, amino, methyl, ethyl, n-propyl, isopropyl, n-butyl, isobutyl, sec-butyl, tert-butyl, cyclopropyl, 1-chlorocyclopropyl, vinyl, ethynyl, methoxy, ethoxy, isopropoxy, methylthio, ethylthio, trifluoromethylthio, chlorodifluoromethyl, dichlorofluoromethyl, chlorofluoromethyl, chloromethyl, dichloromethyl, trichloromethyl, fluoromethyl, difluoromethyl, trifluoromethyl, 2,2,2-trifluoroethyl, trifluoromethoxy, trifluoromethylthio, 2,2,2-trifluorothoxy, 2,2-dichloro-2-fluoroethyl, 2,2-difluoro-2-chloroethyl, 2-chloro-2-fluoroethyl, 2,2,2-trichloroethyl, 2,2,2-trifluoroethyl, 2-fluoroethyl, 2,2-difluoroethyl, 2-methoxyethoxy, acetyl, propionyl, methoxycarbonyl, ethoxycarbonyl, N-methylamino, N,N-dimethylamino, N-ethylamino, N,N-diethylamino, aminocarbonyl, methylaminocarbonyl, dimethylaminocarbonyl, dimethylcarbamoylamino, methoxycarbonylamino, methoxycarbonyloxy, ethoxycarbonylamino, ethoxycarbonyloxy, methylsulfamoyl, dimethylsulfamoyl, phenyl or phenoxy.

A saturated or unsaturated five-membered heterocycle is to be understood to mean a five-membered ring system which, in addition to carbon atoms, contains 1 to 4 heteroatoms from the group consisting of oxygen, sulfur and nitrogen. Examples of such a heterocycle are furan, thiophene, 1,2-oxazole, 1,3-oxazole, 1,2-thiazole, 1,3-thiaxazole, imidazole, pyrazole, 1,2-diazole, 1,2,5-oxadiazole and in each case their unsaturated and partially saturated analogs.

Depending inter alia on the nature of the substituents, the compounds of the formula (I) can be present as geometrical and/or optical isomers or isomer mixtures of varying composition which, if desired, can be separated in a customary manner. The present invention provides both the pure isomers and the isomer mixtures, their preparation and use and compositions comprising them. For the sake of simplicity, however, reference is always made hereinafter to compounds of the formula (I), even though this means both the pure compounds and, if appropriate, mixtures having different proportions of isomeric compounds.

A metal ion equivalent is a metal ion having a positive charge, such as $Na^+$, $K^+$, $(Mg^{2+})_{1/2}$, $(Ca^{2+})_{1/2}$, $MgH^+$, $CaH^+$, $(Al^{3+})_{1/3}$ $(Fe^{2+})_{1/2}$ or $(Fe^{3+})_{1/3}$.

Halogen is fluorine, chlorine, bromine or iodine.

Where a group is substituted by a plurality of radicals, this means that this group is substituted by one or more identical or different representatives of the radicals mentioned.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis.

Examples of inorganic acids are hydrohalic acids such as hydrogen fluoride, hydrogen chloride, hydrogen bromide and hydrogen iodide, sulfuric acid, phosphoric acid and nitric acid, and acidic salts such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulfonic acid, salicylic acid, p-aminosalicylic acid, 2-phenoxybenzoic acid, 2-acetoxybenzoic acid, etc. Suitable metal ions are in particular the ions of the elements of the second main group, in particular calcium and magnesium, of the third and fourth main group, in particular aluminum, tin and lead, and also of the first to eighth transition group, in particular chromium, manganese, iron, cobalt, nickel, copper, zinc and others. Particular preference is given to the metal ions of the elements of the fourth period. Here, the metals can be present in the various valencies that they can assume.

If the compounds of the formula (I) carry hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $(C_1-C_4)$-alkyl groups, mono-, di- and trialkanolamines of $(C_1-C_4)$-alkanols, choline and chlorocholine.

According to the nature of the substituents and the way in which they are joined, the compounds of the formula (I) may be present as stereoisomers. If, for example, one or more asymmetrically substituted carbon atoms or sulfoxides are present, enantiomers and diastereomers may occur. Stereoisomers may be obtained from the mixtures resulting from the preparation using customary separation methods, for example by chromatographic separation techniques. It is equally possible to selectively prepare stereoisomers by using stereoselective reactions using optically active starting materials and/or auxiliaries. The invention also relates to all stereoisomers and mixtures thereof which are encompassed by the formula (I) but not defined specifically.

In all the formulae specified hereinafter, the substituents and symbols have the same meaning as in formula (I), unless defined differently.

Preference is given to thiazolopyridinones of the formula (I) in which $R^1$ represents hydrogen,
$(C_1-C_6)$-alkyl, $(C_1-C_6)$-alkoxy, $(C_1-C_6)$-alkylthio, $(C_1-C_6)$-alkylsulfonyl, $(C_3-C_6)$-cycloalkyl, $(C_1-C_6)$-alkoxy-$(C_1-C_6)$-alkyl or $(C_1-C_6)$-alkylthio-$(C_1-C_6)$-alkyl, each of which is substituted by n halogen atoms, $R^2$ represents hydrogen,
$(C_1-C_6)$-alkyl, $(C_2-C_6)$-alkenyl, $(C_3-C_6)$-alkynyl, $(C_1-C_6)$-alkoxy-$(C_1-C_6)$-alkyl, $(C_1-C_6)$-alkylthio-$(C_1-C_6)$-alkyl, $(C_3-C_6)$-cycloalkyl-$(C_1-C_6)$-alkyl, cyano-$(C_1-C_6)$-alkyl, each of which is substituted by n halogen atoms, or phenyl or benzyl, each of which is substituted by n radicals from the group consisting of halogen, $(C_1-C_6)$-alkyl and $(C_1-C_6)$-alkoxy, $R^3$ represents hydroxy, O—C(=O)$R^7$, O—C(=L)M$R^8$, O—SO$_2$$R^9$, O—P(=L)$R^{10}$$R^{11}$, O—C(=L)N$R^{12}$$R^{13}$, O-E or O—$R^{14}$, $R^4$ represents $R^{4a}$ or $R^{4b}$, $R^{4a}$ represents phenyl which is substituted by one, two or three radicals $R^5$ and one radical $R^6$, $R^{4b}$ represents 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-1-yl, 1,2,4-triazol-3-yl, 1,2,4-triazol-4-yl, 1,2,4-triazol-5-yl, 1,2,3-triazol-1-yl, 1,2,3-triazol-2-yl, 1,2,3-triazol-4-yl, tetrazol-1-yl, tetrazol-2-yl, tetrazol-5-yl, indol-1-yl, indol-2-yl, indol-3-yl, isoindol-1-yl, isoindol-2-yl, benzofur-2-yl, benzothiophen-2-yl, benzofur-3-yl, benzothiophen-3-yl, benzoxazol-2-yl, benzothiazol-2-yl, benzimidazol-2-yl, indazol-1-yl, indazol-2-yl, indazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl or 1,2,4-triazin-6-yl, substituted by one or two radicals $R^5$ and by m radicals $R^6$, $R^5$ represents hydrogen, halogen,
$(C_1-C_6)$-alkyl, $(C_2-C_6)$-alkenyl, $(C_2-C_6)$-alkynyl, $(C_1-C_6)$-alkoxy, $(C_3-C_6)$-cycloalkyl or $(C_1-C_6)$-alkoxy-$(C_1-C_6)$-alkyl, each of which is substituted by n halogen atoms, $R^6$ represents phenyl substituted by n radicals $R^5$ or heteroaryl substituted by one, two or three radicals $R^5$, E represents a metal ion equivalent or an ammonium ion, L represents oxygen or sulfur, M represents oxygen or sulfur, $R^7$ represents $(C_1-C_6)$-alkyl, $(C_2-C_6)$-alkenyl, $(C_1-C_6)$-alkoxy-$(C_1-C_6)$-alkyl, di-$(C_1-C_6)$-alkoxy-$(C_1-C_6)$-alkyl or $(C_1-C_6)$-alkylthio-$(C_1-C_6)$-alkyl, each of which is substituted by n halogen atoms, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, $(C_1-C_6)$-alkyl and $(C_1-C_6)$-alkoxy, or $(C_3-C_6)$-cycloalkyl, phenyl, phenyl-$(C_1-C_6)$-alkyl, phenoxy-$(C_1-C_6)$-alkyl or heteroaryloxy-$(C_1-C_6)$-alkyl, each of which is substituted by n radicals from the group consisting of halogen, $(C_1-C_6)$-alkyl and $(C_1-C_6)$-alkoxy, $R^8$ represents $(C_1-C_6)$-alkyl, $(C_2-C_6)$-alkenyl, $(C_1-C_6)$-alkoxy-$(C_1-C_6)$-alkyl or di-$(C_1-C_6)$-alkoxy-$(C_1-C_6)$-alkyl, each of which is substituted by n halogen atoms, or $(C_3-C_6)$-cycloalkyl, phenyl or benzyl, each of which is substituted by n radicals from the group consisting of halogen, $(C_1-C_6)$-alkyl and $(C_1-C_6)$-alkoxy, $R^9$, $R^{10}$, $R^{11}$ independently of one another represent $(C_1-C_6)$-alkyl, $(C_1-C_6)$-alkoxy, N—$(C_1-C_6)$-alkylamino, N,N-di-$(C_1-C_6)$-Alkylamino, $(C_1-C_6)$-alkylthio, $(C_2-C_6)$-alkenyl or $(C_3-C_6)$-cycloalkylthio, each of which is substituted by n halogen atoms, or phenyl, benzyl, phenoxy or phenylthio, each of which is substituted by n radicals from the group consisting of halogen, $(C_1-C_6)$-alkyl and $(C_1-C_6)$-alkoxy, $R^{12}$, $R^{13}$ independently of one another each represent hydrogen, $(C_1-C_6)$-alkyl, $(C_3-C_6)$-cycloalkyl, $(C_2-C_6)$-alkenyl, $(C_1-C_6)$-alkoxy or $(C_1-C_6)$-alkoxy-$(C_1-C_6)$-alkyl, substituted by n halogen atoms, phenyl or benzyl, each of which is substituted by n radicals from the group consisting of halogen, $(C_1-C_6)$-alkyl and $(C_1-C_6)$-alkoxy, or $R^{12}$ and $R^{13}$ together with the nitrogen atom to which they are attached form a 3- to 6-membered ring containing 2 to 5 carbon atoms and in each case 0 or 1 oxygen or sulfur atoms;

$R^{14}$ represents $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_1-C_6)$-alkylthio-$(C_1-C_6)$-alkyl or di-$(C_1-C_6)$-alkoxy-$(C_1-C_6)$-alkyl, each of which is substituted by n halogen atoms, $(C_3-C_6)$-cycloalkyl substituted by n radicals from the group consisting of halogen, $(C_1-C_6)$-alkyl and $(C_1-C_6)$-alkoxy, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, $(C_1-C_6)$-alkyl and $(C_1-C_6)$-alkoxy, phenyl, phenyl-$(C_1-C_6)$-alkyl, heteroaryl, phenoxy-$(C_1-C_6)$-alkyl or heteroaryloxy-$(C_1-C_6)$-alkyl, substituted by n radicals from the group consisting of halogen, $(C_1-C_6)$-alkyl and $(C_1-C_6)$-alkoxy, m represents 0 or 1, n represents 0, 1, 2 or 3, s represents 0, 1, 2, 3 or 4.

Particular preference is given to the compounds of the formula (I) listed below.

TABLE 1

Compounds of the formula (I) according to the invention in which $R^1$ represents hydrogen, $R^2$ represents 2,2-difluoroethyl and $R^3$ represents hydroxy.

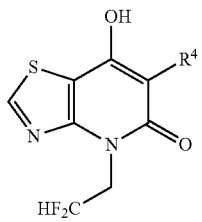

| No. | $R^4$ |
|---|---|
| 1 | 2-chloro-4-(5-chloro-2-thienyl)-6-ethylphenyl |
| 2 | 2-chloro-4-(2,4-dichlorophenyl)-6-ethylphenyl |
| 3 | 2-chloro-4-(4-chlorophenyl)-6-ethylphenyl |
| 4 | 2,6-dichloro-3-(5-chloro-2-thienyl)phenyl |
| 5 | 2,6-dichloro-3-(2,4-dichlorophenyl)phenyl |
| 6 | 3-(4-chlorophenyl)-2,6-dichlorophenyl |
| 7 | 2-chloro-3-(5-chloro-2-thienyl)-6-fluorophenyl |
| 8 | 2-chloro-3-(2,4-dichlorophenyl)-6-fluorophenyl |
| 9 | 2-chloro-3-(4-chlorophenyl)-6-fluorophenyl |
| 10 | 2-chloro-4-(4-chlorophenyl)phenyl |
| 11 | 2-chloro-3-(4-chlorophenyl)phenyl |
| 12 | 5-(4-chlorophenyl)-2-methylphenyl |
| 13 | 3-(3-chlorophenyl)-2,6-dichlorophenyl |
| 14 | 2,6-dichloro-(3-phenyl)phenyl |
| 15 | 2-chloro-4-(4-fluorophenyl)phenyl |
| 16 | 4-(4-bromophenyl)-2-chlorophenyl |
| 17 | 2-chloro-4-(4-iodophenyl)phenyl |
| 18 | 2-bromo-4-(4-chlorophenyl)phenyl |
| 19 | 2-bromo-4-(4-fluorophenyl)phenyl |
| 20 | 2-bromo-4-(4-iodophenyl)phenyl |
| 21 | 4-(4-chlorophenyl)-3-fluorophenyl |
| 22 | 4-(4-bromophenyl)-3-fluorophenyl |
| 23 | 3-fluoro-4-(4-iodophenyl)phenyl |
| 24 | 3-fluoro-4-(4-fluorophenyl)phenyl |
| 25 | 4-(4-chlorophenyl)-2-iodophenyl |
| 26 | 4-(4-bromophenyl)-2-iodophenyl |
| 27 | 4-(4-fluorophenyl)-2-iodophenyl |
| 28 | 2-iodo-4-(4-iodophenyl)phenyl |
| 29 | 4-(4-fluorophenyl)-2-trifluoromethylphenyl |
| 30 | 4-(4-chlorophenyl)-2-trifluoromethylphenyl |
| 31 | 4-(4-iodophenyl)-2-trifluoromethylphenyl |
| 32 | 4-(4-bromophenyl)-2-trifluoromethylphenyl |
| 33 | 5-chloro-2-(4-chlorophenyl)-1,3-thiazol-4-yl |
| 34 | 2-(2-chlorophenyl)-5-methyl-1,3-thiazol-4-yl |
| 35 | 5-bromo-2-(4-chlorophenyl)-1,3-thiazol-4-yl |
| 36 | 3-(4-fluorophenyl)-1-methyl-1H-1,2,4-triazol-5-yl |
| 37 | 1-[2,6-dichloro-4-(trifluoromethyl)phenyl]-3,5-dimethyl-1H-pyrazol-4-yl |
| 38 | 1-[2,6-dichloro-4-(trifluoromethoxy)phenyl]-3,5-dimethyl-1H-pyrazol-4-yl |
| 39 | 2-chloro-3-thiophenyl |
| 40 | 4-chloro-5-methyl-3-(trifluoromethyl)-1H-pyrazol-1-yl |
| 41 | 5-methyl-3-(trifluoromethyl)-1H-pyrazol-1-yl |
| 42 | 3,5-bis(trifluoromethyl)-1H-pyrazol-1-yl |
| 43 | 3,5-bis(difluoromethyl)-1H-pyrazol-1-yl |
| 44 | 6-chloropyridin-3-yl |
| 45 | 4-chloropyridin-2-yl |
| 46 | 2-chloropyridin-4-yl |
| 47 | 4,6-dichloropyridin-3-yl |
| 48 | 2-chloropyridin-3-yl |
| 49 | 5-chloro-3-(trifluoromethyl)pyridin-2-yl |
| 50 | 5-chloro-2-thiophenyl |
| 51 | 2-chloro-1,3-thiazol-5-yl |
| 52 | 2-(4-chlorophenyl)-1,3-thiazol-4-yl |
| 53 | 2-(3-chlorophenyl)-1,3-thiazol-4-yl |
| 54 | 2-(4-chlorophenyl)-1,3-oxazol-4-yl |
| 55 | 5-(4-chlorophenyl)-1,2-oxazol-3-yl |
| 56 | 5-chloro-3-methyl-1,2-oxazol-4-yl |
| 57 | 3,5-dimethyl-1,2-oxazol-4-yl |

TABLE 1-continued

Compounds of the formula (I) according to the invention in which $R^1$ represents hydrogen, $R^2$ represents 2,2-difluoroethyl and $R^3$ represents hydroxy.

| No. | $R^4$ |
|---|---|
| 58 | 4-nitro-1H-pyrazol-1-yl |
| 59 | 4-chloro-5-methyl-3-nitro-1H-pyrazol-1-yl |
| 60 | 4-chloro-3-cyclopropyl-1H-pyrazol-1-yl |
| 61 | 3-(4-chlorophenyl)-5-methyl-1H-pyrazol-1-yl |
| 62 | 1-(5-chloropyridin-2-yl)-3,5-dimethyl-1H-pyrazol-4-yl |
| 63 | 4-chloro-1H-pyrazol-1yl |
| 64 | 4-nitro-1H-imidazol-1yl |
| 65 | 4,5-dichloro-1H-imidazol-1yl |
| 66 | 3-(2-chlorophenyl)-1,2,4-oxadiazol-5-yl |
| 67 | 3-(3-chlorophenyl)-1,2,4-oxadiazol-5-yl |
| 68 | 5-(3-chlorophenyl)-1,3,4-oxadiazol-2-yl |
| 69 | 1H-1,2,4-triazol-1-yl |
| 70 | 1-(2,4-dichlorophenyl)-1H-1,2,3-triazol-5-yl |
| 71 | 1H-tetrazol-1-yl |
| 72 | 1-ethyl-3-(4-fluorophenyl)-1H-1,2,4-triazol-5-yl |
| 73 | 3-(4-chlorophenyl)-1-methyl-1H-1,2,4-triazol-5-yl |
| 74 | 3-(4-chlorophenyl)-1-ethyl-1H-1,2,4-triazol-5-yl |
| 75 | 5-methyl-3-phenyl-1H-pyrazol-1-yl |
| 76 | 3-(4-chlorophenyl)-5-ethyl-1H-pyrazol-1-yl |
| 77 | 3-(4-chlorophenyl)-5-propyl-1H-pyrazol-1-yl |
| 78 | 3-(3-chlorophenyl)-5-methyl-1H-pyrazol-1-yl |
| 79 | 3-(3,4-dichlorophenyl)-5-methyl-1H-pyrazol-1-yl |
| 80 | 3-(4-bromophenyl)-5-methyl-1H-pyrazol-1-yl |
| 81 | 3-(3-bromophenyl)-5-methyl-1H-pyrazol-1-yl |
| 82 | 5-methyl-3-(4-trifluoromethylphenyl)-1H-pyrazol-1-yl |
| 83 | 5-methyl-3-(3-trifluoromethylphenyl)-1H-pyrazol-1-yl |
| 84 | 1-methyl-3-phenyl-1H-1,2,4-triazol-5-yl |
| 85 | 1-ethyl-3-phenyl-1H-1,2,4-triazol-5-yl |
| 86 | 1-cyclopropyl-3-phenyl-1H-1,2,4-triazol-5-yl |
| 87 | 3-(2-chlorophenyl)-1-methyl-1H-1,2,4-triazol-5-yl |
| 88 | 3-(2-chlorophenyl)-1-ethyl-1H-1,2,4-triazol-5-yl |
| 89 | 3-(2-chlorophenyl)-1-cyclopropyl-1H-1,2,4-triazol-5-yl |
| 90 | 3-(3-chlorophenyl)-1-methyl-1H-1,2,4-triazol-5-yl |
| 91 | 3-(3-chlorophenyl)-1-ethyl-1H-1,2,4-triazol-5-yl |
| 92 | 3-(3-chlorophenyl)-1-cyclopropyl-1H-1,2,4-triazol-5-yl |
| 93 | 3-(4-chlorophenyl)-1-cyclopropyly1-1H-1,2,4-triazol-5-yl |
| 94 | 3-(2-fluorophenyl)-1-methyl-1H-1,2,4-triazol-5-yl |
| 95 | 1-ethyl-3-(2-fluorophenyl)-1H-1,2,4-triazol-5-yl |
| 96 | 1-cyclopropyl-3-(2-fluorophenyl)-1H-1,2,4-triazol-5-yl |
| 97 | 1-cyclopropyl-3-(4-fluorophenyl)-1H-1,2,4-triazol-5-yl |
| 98 | 3-(2,4-difluorophenyl)-1-methyl-1H-1,2,4-triazol-5-yl |
| 99 | 3-(2,4-difluorophenyl)-1-ethyl-1H-1,2,4-triazol-5-yl |
| 100 | 1-cyclopropyl-3-(2,4-difluorophenyl)-1H-1,2,4-triazol-5-yl |
| 101 | 1-methyl-3-(2-trifluoromethylphenyl)-1H-1,2,4-triazol-5-yl |
| 102 | 1-ethyl-3-(2-trifluoromethylphenyl)-1H-1,2,4-triazol-5-yl |
| 103 | 1-cyclopropyl-3-(2-trifluoromethylphenyl)-1H-1,2,4-triazol-5-yl |
| 104 | 3-(2,4-dichlorophenyl)-1-methyl-1H-1,2,4-triazol-5-yl |
| 105 | 3-(2,4-dichlorophenyl)-1-ethyl-1H-1,2,4-triazol-5-yl |
| 106 | 1-cyclopropyl-3-(2,4-dichlorophenyl)-1H-1,2,4-triazol-5-yl |
| 107 | 3-[4-chloro-2-(trifluoromethyl)phenyl]-1-methyl-1H-1,2,4-triazol-5-yl |
| 108 | 3-[4-chloro-2-[trifluoromethyl)phenyl]-1-ethyl-1H-1,2,4-triazol-5-yl |
| 109 | 3-[4-chloro-2-(trifluoromethyl)phenyl)-1-cyclopropyl-1H-1,2,4-triazol-5-yl |
| 110 | 3-(2-chloro-4-methylphenyl)-1-methyl-1H-1,2,4-triazol-5-yl |
| 111 | 3-(2-chloro-4-methylphenyl)-1-ethyl-1H-1,2,4-triazol-5-yl |
| 112 | 3-(2-chloro-4-methylphenyl)-1-cyclopropyl-1H-1,2,4-triazol-5-yl |
| 113 | 3-(2,4-dichlorophenyl)-1-(2,2-difluoroethyl)-1H-1,2,4-triazol-5-yl |
| 114 | 3-(4,5-dihydro-1,2-oxazol-3-yl)-2-(trifluoromethyl)phenyl |

Table 2: Compounds of the formula (I) according to the invention in which $R^1$ represents hydrogen, $R^2$ represents 2,2,2-trifluoroethoxy and $R^3$ represents hydroxy and $R^4$ has the meanings given in Table 1:

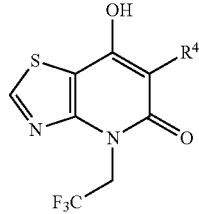

Table 3: Compounds of the formula (I) according to the invention in which $R^1$ represents hydrogen, $R^2$ represents methyl and $R^3$ represents hydroxy and $R^4$ has the meanings given in Table 1:

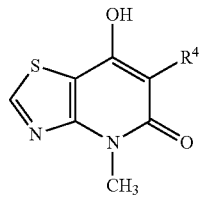

Table 4: Compounds of the formula (I) according to the invention in which $R^1$ represents hydrogen, $R^2$ represents ethyl and $R^3$ represents hydroxy and $R^4$ has the meanings given in Table 1:

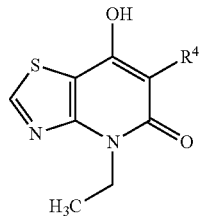

Table 5: Compounds of the formula (I) according to the invention in which $R^1$ represents hydrogen, $R^2$ represents isopropyl and $R^3$ represents hydroxy and $R^4$ has the meanings given in Table 1:

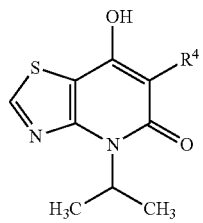

Table 6: Compounds of the formula (I) according to the invention in which $R^1$ represents hydrogen, $R^2$ represents propargyl and $R^3$ represents hydroxy and $R^4$ has the meanings given in Table 1:

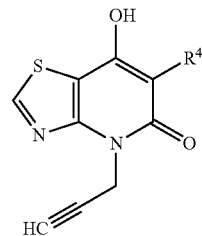

Table 7: Compounds of the formula (I) according to the invention in which $R^1$ represents hydrogen, $R^2$ represents allyl and $R^3$ represents hydroxy and $R^4$ has the meanings given in Table 1:

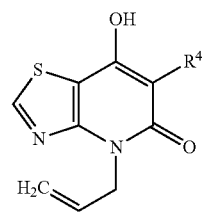

Table 8: Compounds of the formula (I) according to the invention in which $R^1$ represents hydrogen, $R^2$ represents cyanomethyl and $R^3$ represents hydroxy and $R^4$ has the meanings given in Table 1:

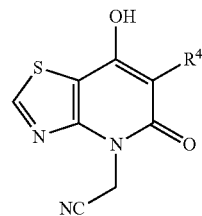

Table 9: Compounds of the formula (I) according to the invention in which $R^1$ represents hydrogen, $R^2$ represents methoxyethyl and $R^3$ represents hydroxy and $R^4$ has the meanings given in Table 1:

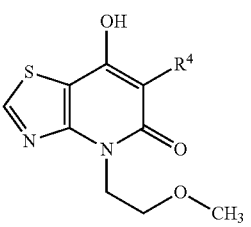

Table 10: Compounds of the formula (I) according to the invention in which $R^1$ represents hydrogen, $R^2$ represents methylthioethyl and $R^3$ represents hydroxy and $R^4$ has the meanings given in Table 1:

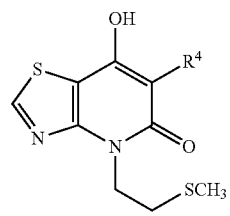

Table 11: Compounds of the formula (I) according to the invention in which R¹ represents methylthio, R² represents 2,2-difluoroethyl and R³ represents hydroxy and R⁴ has the meanings given in Table 1:

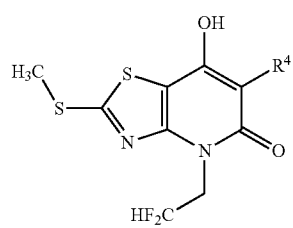

Table 12: Compounds of the formula (I) according to the invention in which R¹ represents methylthio, R² represents 2,2,2-trifluoroethyl and R³ represents hydroxy and R⁴ has the meanings given in Table 1:

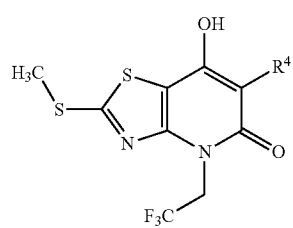

Table 13: Compounds of the formula (I) according to the invention in which R¹ represents methylthio, R² represents methyl and R³ represents hydroxy and R⁴ has the meanings given in Table 1:

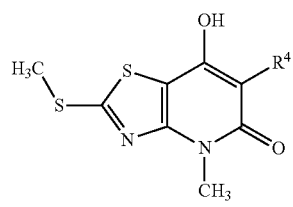

Table 14: Compounds of the formula (I) according to the invention in which R¹ represents methylthio, R² represents ethyl and R³ represents hydroxy and R⁴ has the meanings given in Table 1:

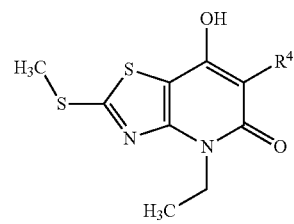

Table 15: Compounds of the formula (I) according to the invention in which R¹ represents methylthio, R² represents isopropyl and R³ represents hydroxy and R⁴ has the meanings given in Table 1:

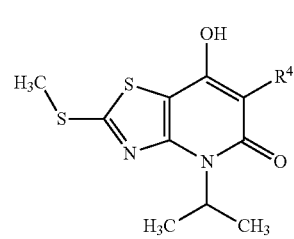

Table 16: Compounds of the formula (I) according to the invention in which R¹ represents methylthio, R² represents propargyl and R³ represents hydroxy and R⁴ has the meanings given in Table 1:

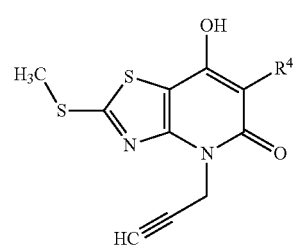

Table 17: Compounds of the formula (I) according to the invention in which R¹ represents methylthio, R² represents allyl and R³ represents hydroxy and R⁴ has the meanings given in Table 1:

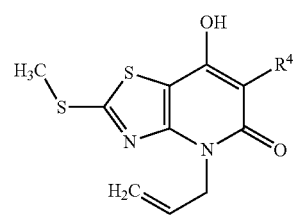

Table 18: Compounds of the formula (I) according to the invention in which R¹ represents methylthio, R² represents cyanomethyl and R³ represents hydroxy and R⁴ has the meanings given in Table 1:

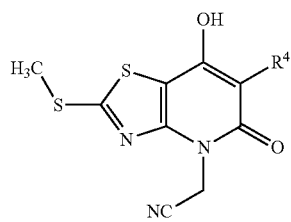

Table 19: Compounds of the formula (I) according to the invention in which $R^1$ represents methylthio, $R^2$ represents methoxyethyl and $R^3$ represents hydroxy and $R^4$ has the meanings given in Table 1:

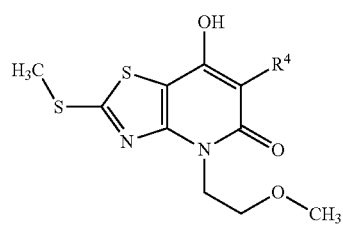

Table 20: Compounds of the formula (I) according to the invention in which $R^1$ represents methylthio, $R^2$ represents methylthioethyl and $R^3$ represents hydroxy and $R^4$ has the meanings given in Table 1:

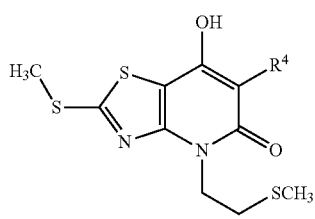

Table 11: Compounds of the formula (I) according to the invention in which $R^1$ represents methyl-sulfonyl, $R^2$ represents 2,2-difluoroethyl and $R^3$ represents hydroxy and $R^4$ has the meanings given in Table 1:

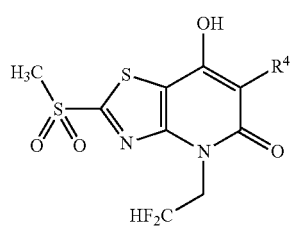

Table 12: Compounds of the formula (I) according to the invention in which $R^1$ represents methyl-sulfonyl, $R^2$ represents 2,2,2-trifluoroethyl and $R^3$ represents hydroxy and $R^4$ has the meanings given in Table 1:

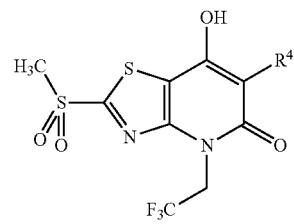

Table 13: Compounds of the formula (I) according to the invention in which $R^1$ represents methyl-sulfonyl, $R^2$ represents methyl and $R^3$ represents hydroxy and $R^4$ has the meanings given in Table 1:

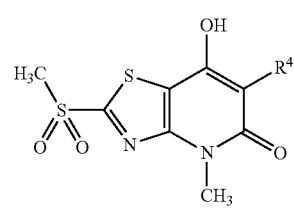

Table 14: Compounds of the formula (I) according to the invention in which $R^1$ represents methyl-sulfonyl, $R^2$ represents ethyl and $R^3$ represents hydroxy and $R^4$ has the meanings given in Table 1:

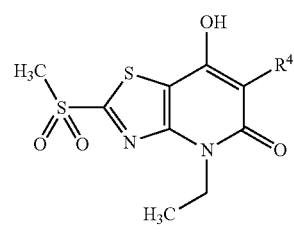

Table 15: Compounds of the formula (I) according to the invention in which $R^1$ represents methyl-sulfonyl, $R^2$ represents isopropyl and $R^3$ represents hydroxy and $R^4$ has the meanings given in Table 1:

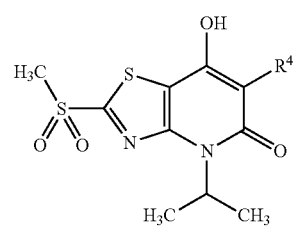

Table 16: Compounds of the formula (I) according to the invention in which $R^1$ represents methyl-sulfonyl, $R^2$ represents propargyl and $R^3$ represents hydroxy and $R^4$ has the meanings given in Table 1:

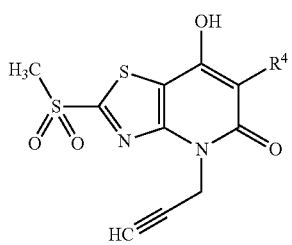

Table 17: Compounds of the formula (I) according to the invention in which $R^1$ represents methyl-sulfonyl, $R^2$ represents allyl and $R^3$ represents hydroxy and $R^4$ has the meanings given in Table 1:

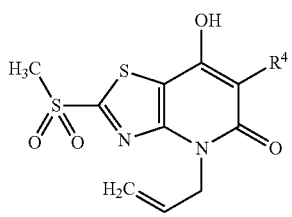

Table 18: Compounds of the formula (I) according to the invention in which $R^1$ represents methyl-sulfonyl, $R^2$ represents benzyl and $R^3$ represents hydroxy and $R^4$ has the meanings given in Table 1:

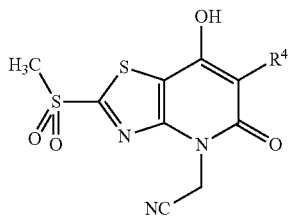

Table 19: Compounds of the formula (I) according to the invention in which $R^1$ represents methyl-sulfonyl, $R^2$ represents methoxyethyl and $R^3$ represents hydroxy and $R^4$ has the meanings given in Table 1:

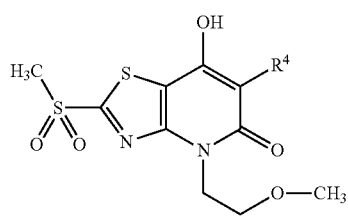

Table 20: Compounds of the formula (I) according to the invention in which $R^1$ represents methyl-sulfonyl, $R^2$ represents methylthioethyl and $R^3$ represents hydroxy and $R^4$ has the meanings given in Table 1:

Table 21: Compounds of the formula (I) according to the invention in which $R^1$ represents methyl, $R^2$ represents 2,2-difluoroethyl and $R^3$ represents hydroxy and $R^4$ has the meanings given in Table 1:

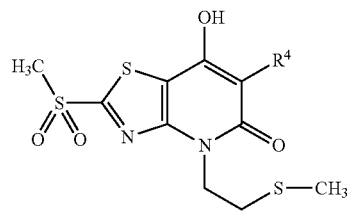

Table 22: Compounds of the formula (I) according to the invention in which $R^1$ represents methyl, $R^2$ represents 2,2,2-trifluoroethyl and $R^3$ represents hydroxy and $R^4$ has the meanings given in Table 1:

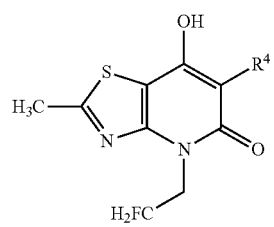

Table 23: Compounds of the formula (I) according to the invention in which $R^1$ represents methyl, $R^2$ represents methyl and $R^3$ represents hydroxy and $R^4$ has the meanings given in Table 1:

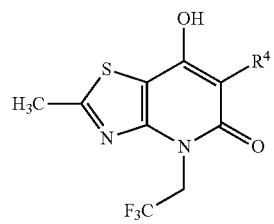

Table 24: Compounds of the formula (I) according to the invention in which $R^1$ represents methyl, $R^2$ represents ethyl and $R^3$ represents hydroxy and $R^4$ has the meanings given in Table 1:

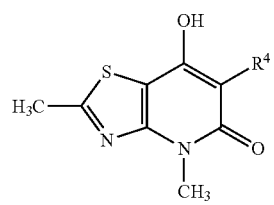

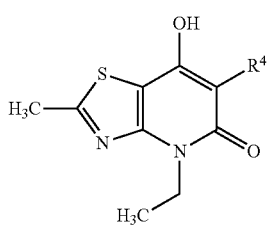

Table 25: Compounds of the formula (I) according to the invention in which R¹ represents methyl, R² represents isopropyl and R³ represents hydroxy and R⁴ has the meanings given in Table 1:

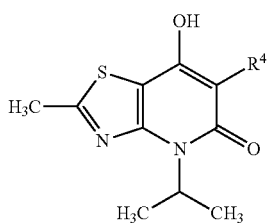

Table 26: Compounds of the formula (I) according to the invention in which R¹ represents methyl, R² represents propargyl and R³ represents hydroxy and R⁴ has the meanings given in Table 1:

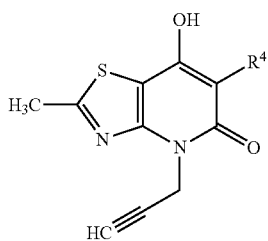

Table 27: Compounds of the formula (I) according to the invention in which R¹ represents methyl, R² represents allyl and R³ represents hydroxy and R⁴ has the meanings given in Table 1:

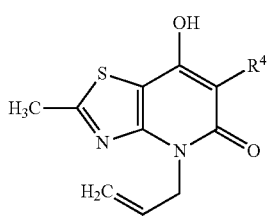

Table 28: Compounds of the formula (I) according to the invention in which R¹ represents methyl, R² represents cyanomethyl and R³ represents hydroxy and R⁴ has the meanings given in Table 1:

Table 29: Compounds of the formula (I) according to the invention in which R¹ represents methyl, R² represents methoxyethyl and R³ represents hydroxy and R⁴ has the meanings given in Table 1:

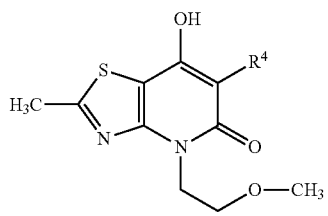

Table 30: Compounds of the formula (I) according to the invention in which R¹ represents methyl, R² represents methylthioethyl and R³ represents hydroxy and R⁴ has the meanings given in Table 1:

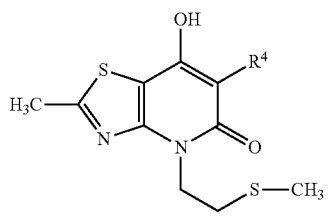

Table 31: Compounds of the formula (I) according to the invention in which R¹ represents cyclopropyl, R² represents 2,2-difluoroethyl and R³ represents hydroxy and R⁴ has the meanings given in Table 1:

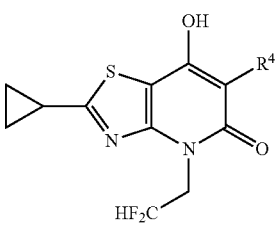

Table 32: Compounds of the formula (I) according to the invention in which R¹ represents cyclopropyl, R² represents 2,2,2-trifluoroethyl and R³ represents hydroxy and R⁴ has the meanings given in Table 1:

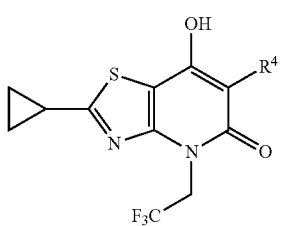

Table 33: Compounds of the formula (I) according to the invention in which $R^1$ represents cyclopropyl, $R^2$ represents methyl and $R^3$ represents hydroxy and $R^4$ has the meanings given in Table 1:

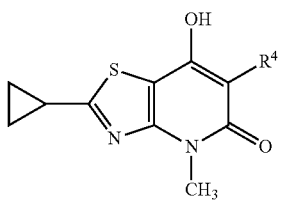

Table 34: Compounds of the formula (I) according to the invention in which $R^1$ represents cyclopropyl, $R^2$ represents ethyl and $R^3$ represents hydroxy and $R^4$ has the meanings given in Table 1:

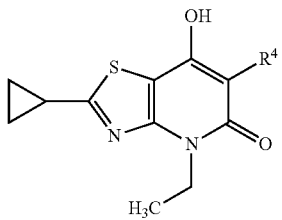

Table 35: Compounds of the formula (I) according to the invention in which $R^1$ represents cyclopropyl, $R^2$ represents isopropyl and $R^3$ represents hydroxy and $R^4$ has the meanings given in Table 1:

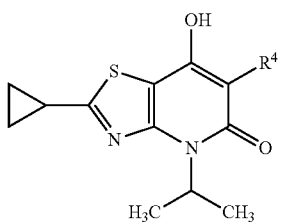

Table 36: Compounds of the formula (I) according to the invention in which $R^1$ represents cyclopropyl, $R^2$ represents propargyl and $R^3$ represents hydroxy and $R^4$ has the meanings given in Table 1:

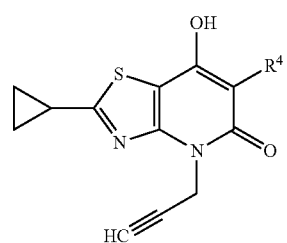

Table 37: Compounds of the formula (I) according to the invention in which $R^1$ represents cyclopropyl, $R^2$ represents allyl and $R^3$ represents hydroxy and $R^4$ has the meanings given in Table 1:

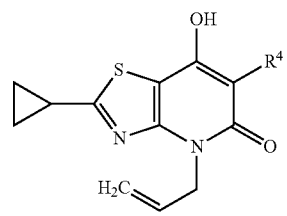

Table 38: Compounds of the formula (I) according to the invention in which $R^1$ represents cyclopropyl, $R^2$ represents cyanomethyl and $R^3$ represents hydroxy and $R^4$ has the meanings given in Table 1:

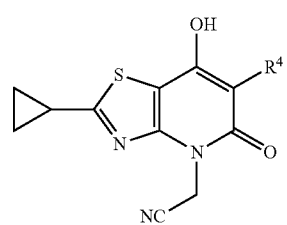

Table 39: Compounds of the formula (I) according to the invention in which $R^1$ represents cyclopropyl, $R^2$ represents methoxyethyl and $R^3$ represents hydroxy and $R^4$ has the meanings given in Table 1:

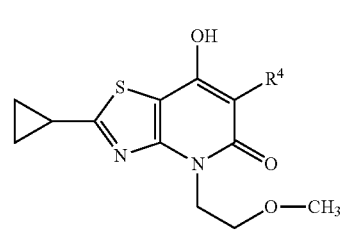

Table 40: Compounds of the formula (I) according to the invention in which $R^1$ represents cyclopropyl, $R^2$ represents methylthioethyl and $R^3$ represents hydroxy and $R^4$ has the meanings given in Table 1:

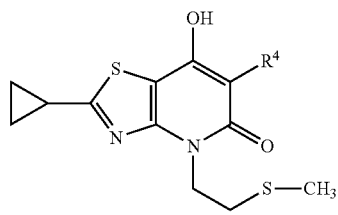

Table 41: Compounds of the formula (I) according to the invention in which $R^1$ represents methoxy, $R^2$ represents 2,2-difluoroethyl and $R^3$ represents hydroxy and $R^4$ has the meanings given in Table 1:

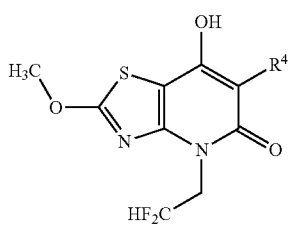

Table 42: Compounds of the formula (I) according to the invention in which $R^1$ represents methoxy, $R^2$ represents 2,2,2-trifluoroethyl and $R^3$ represents hydroxy and $R^4$ has the meanings given in Table 1:

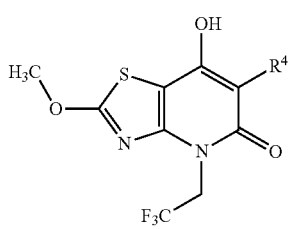

Table 43: Compounds of the formula (I) according to the invention in which $R^1$ represents methoxy, $R^2$ represents methyl and $R^3$ represents hydroxy and $R^4$ has the meanings given in Table 1:

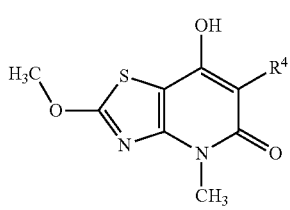

Table 44: Compounds of the formula (I) according to the invention in which $R^1$ represents methoxy, $R^2$ represents ethyl and $R^3$ represents hydroxy and $R^4$ has the meanings given in Table 1:

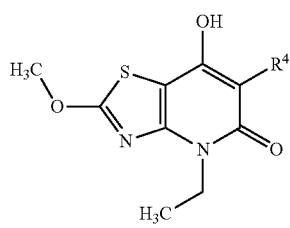

Table 45: Compounds of the formula (I) according to the invention in which $R^1$ represents methoxy, $R^2$ represents isopropyl and $R^3$ represents hydroxy and $R^4$ has the meanings given in Table 1:

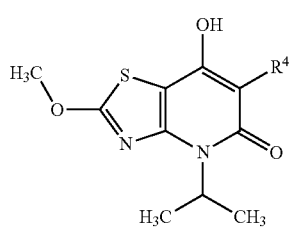

Table 46: Compounds of the formula (I) according to the invention in which $R^1$ represents methoxy, $R^2$ represents propargyl and $R^3$ represents hydroxy and $R^4$ has the meanings given in Table 1:

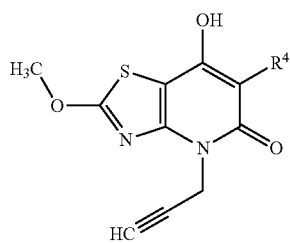

Table 47: Compounds of the formula (I) according to the invention in which $R^1$ represents methoxy, $R^2$ represents allyl and $R^3$ represents hydroxy and $R^4$ has the meanings given in Table 1:

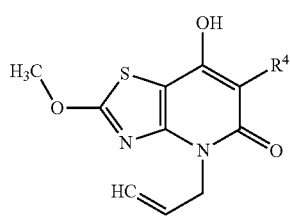

Table 48: Compounds of the formula (I) according to the invention in which $R^1$ represents methoxy, $R^2$ represents cyanomethyl and $R^3$ represents hydroxy and $R^4$ has the meanings given in Table 1:

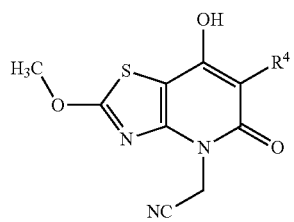

Table 49: Compounds of the formula (I) according to the invention in which R¹ represents methoxy, R² represents methoxyethyl and R³ represents hydroxy and R⁴ has the meanings given in Table 1:

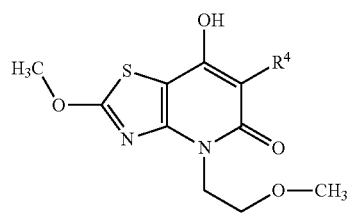

Table 50: Compounds of the formula (I) according to the invention in which R¹ represents methoxy, R² represents methylthioethyl and R³ represents hydroxy and R⁴ has the meanings given in Table 1:

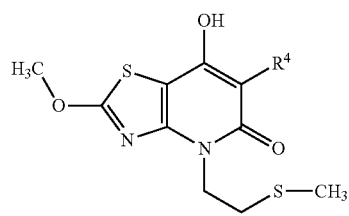

Table 51: Compounds of the formula (I) according to the invention in which R¹ represents ethoxy, R² represents 2,2-difluoroethyl and R³ represents hydroxy and R⁴ has the meanings given in Table 1:

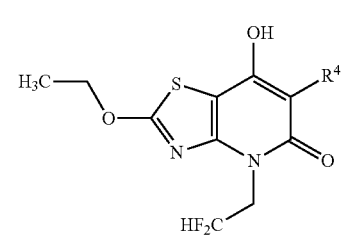

Table 52: Compounds of the formula (I) according to the invention in which R¹ represents ethoxy, R² represents 2,2,2-trifluoroethyl and R³ represents hydroxy and R⁴ has the meanings given in Table 1:

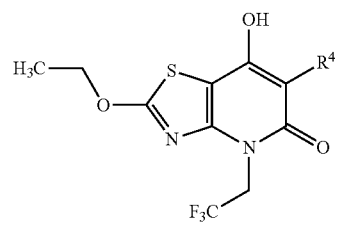

Table 53: Compounds of the formula (I) according to the invention in which R¹ represents ethoxy, R² represents methyl and R³ represents hydroxy and R⁴ has the meanings given in Table 1:

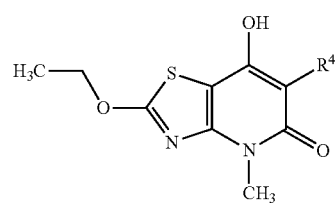

Table 54: Compounds of the formula (I) according to the invention in which R¹ represents ethoxy, R² represents ethyl and R³ represents hydroxy and R⁴ has the meanings given in Table 1:

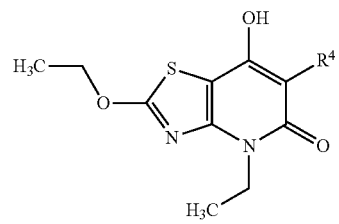

Table 55: Compounds of the formula (I) according to the invention in which R¹ represents ethoxy, R² represents isopropyl and R³ represents hydroxy and R⁴ has the meanings given in Table 1:

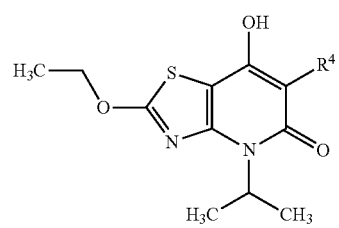

Table 56: Compounds of the formula (I) according to the invention in which R¹ represents ethoxy, R² represents propargyl and R³ represents hydroxy and R⁴ has the meanings given in Table 1:

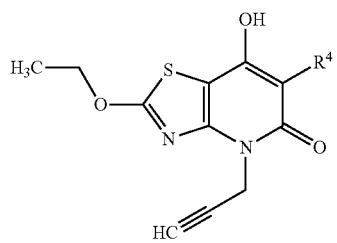

Table 57: Compounds of the formula (I) according to the invention in which $R^1$ represents ethoxy, $R^2$ represents allyl and $R^3$ represents hydroxy and $R^4$ has the meanings given in Table 1:

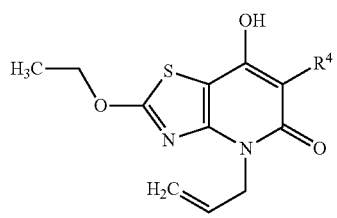

Table 58: Compounds of the formula (I) according to the invention in which $R^1$ represents ethoxy, $R^2$ represents cyanomethyl and $R^3$ represents hydroxy and $R^4$ has the meanings given in Table 1:

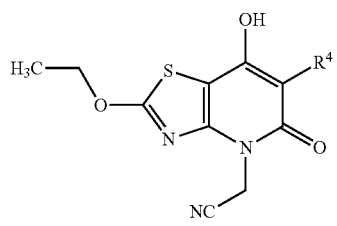

Table 59: Compounds of the formula (I) according to the invention in which $R^1$ represents ethoxy, $R^2$ represents methoxyethyl and $R^3$ represents hydroxy and $R^4$ has the meanings given in Table 1:

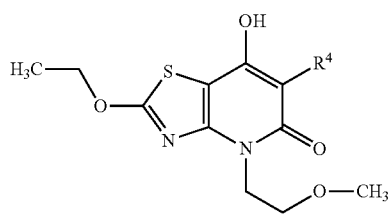

Table 60: Compounds of the formula (I) according to the invention in which $R^1$ represents ethoxy, $R^2$ represents methylthioethyl and $R^3$ represents hydroxy and $R^4$ has the meanings given in Table 1:

Table 61: Compounds of the formula (I) according to the invention in which $R^1$ represents methoxy-ethoxy, $R^2$ represents 2,2-difluoroethyl and $R^3$ represents hydroxy and $R^4$ has the meanings given in Table 1:

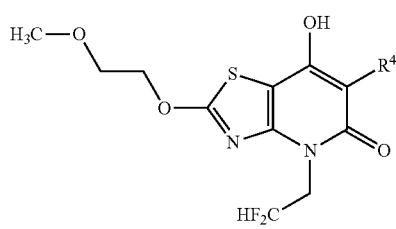

Table 62: Compounds of the formula (I) according to the invention in which $R^1$ represents methoxyethoxy, $R^2$ represents 2,2,2-trifluoroethyl and $R^3$ represents hydroxy and $R^4$ has the meanings given in Table 1:

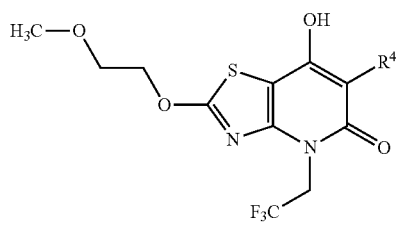

Table 63: Compounds of the formula (I) according to the invention in which $R^1$ represents methoxy-ethoxy, $R^2$ represents methyl and $R^3$ represents hydroxy and $R^4$ has the meanings given in Table 1:

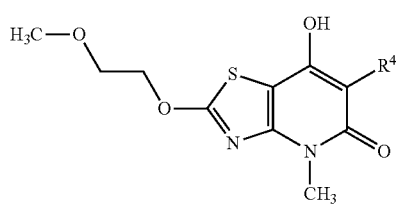

Table 64: Compounds of the formula (I) according to the invention in which $R^1$ represents methoxy-ethoxy, $R^2$ represents ethyl and $R^3$ represents hydroxy and $R^4$ has the meanings given in Table 1:

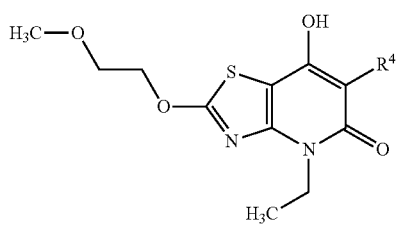

Table 65: Compounds of the formula (I) according to the invention in which $R^1$ represents methoxy-ethoxy, $R^2$ represents isopropyl and $R^3$ represents hydroxy and $R^4$ has the meanings given in Table 1:

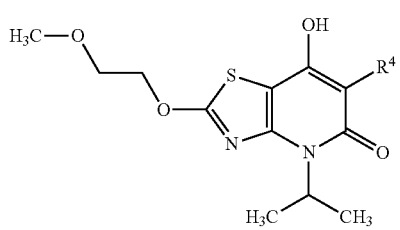

Table 66: Compounds of the formula (I) according to the invention in which $R^1$ represents methoxy-ethoxy, $R^2$ represents propargyl and $R^3$ represents hydroxy and $R^4$ has the meanings given in Table 1:

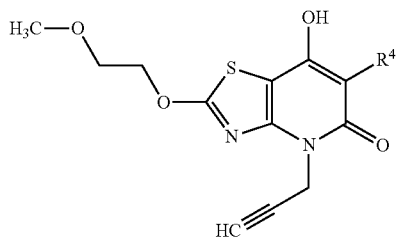

Table 67: Compounds of the formula (I) according to the invention in which $R^1$ represents methoxy-ethoxy, $R^2$ represents allyl and $R^3$ represents hydroxy and $R^4$ has the meanings given in Table 1:

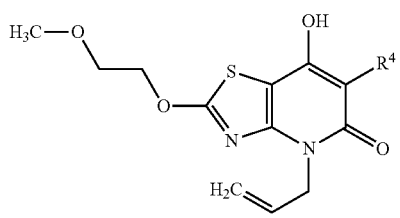

Table 68: Compounds of the formula (I) according to the invention in which $R^1$ represents methoxy-ethoxy, $R^2$ represents cyanomethyl and $R^3$ represents hydroxy and $R^4$ has the meanings given in Table 1:

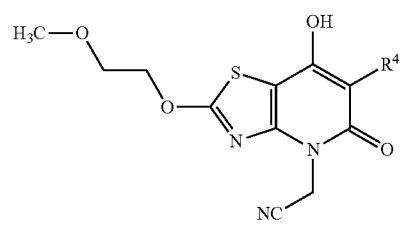

Table 69: Compounds of the formula (I) according to the invention in which $R^1$ represents methoxy-ethoxy, $R^2$ represents methoxyethyl and $R^3$ represents hydroxy and $R^4$ has the meanings given in Table 1:

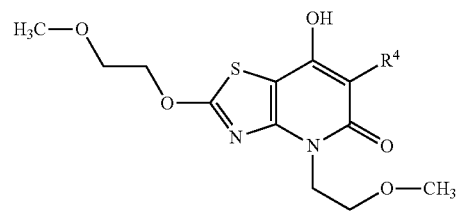

Table 70: Compounds of the formula (I) according to the invention in which $R^1$ represents methoxy-ethoxy, $R^2$ represents methylthioethyl and $R^3$ represents hydroxy and $R^4$ has the meanings given in Table 1:

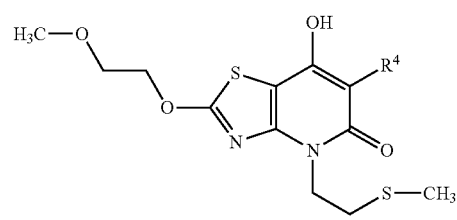

Compounds of the formula (I) according to the invention in which $R^3$ represents hydrogen can be prepared, for example, in accordance with the method shown in Scheme 1 by a base-induced condensation reaction of compounds of the formula (II). Here, $R^7$ represents $(C_1\text{-}C_6)$-alkyl, in particular methyl or ethyl.

Scheme 1

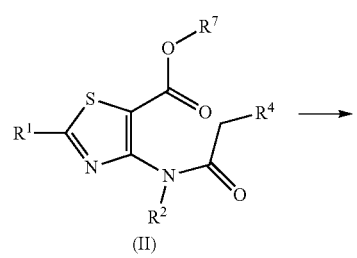

(II)

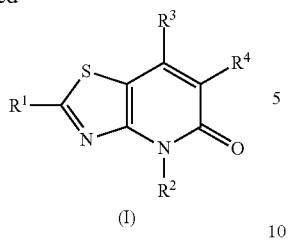

(I)

Compounds of the formula (II) can be prepared, for example, in accordance with the methods shown in Scheme 1a by reaction of aminocarboxylic acid derivatives with phenylacetic acid derivatives. Here, U represents a leaving group introduced by reagents for the activation of carboxylic acids, such as carbonyldiimidazole, carbonyldiimides (such as, for example, dicyclohexylcarbodiimide), phosphorylating agents (such as, for example, $POCl_3$, BOP-Cl), halogenating agents such as, for example, thionyl chloride, oxalyl chloride, phosgene or chloroformic esters. Such methods are also known to the person skilled in the art from WO2008/009908 A1 and WO2008/071918 A1 and WO2009/063180 and the documents cited therein. Compounds compounds of the formula (II) are novel and also form part of the subject matter of the present invention.

Scheme 1a

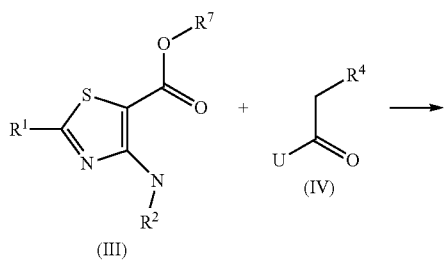

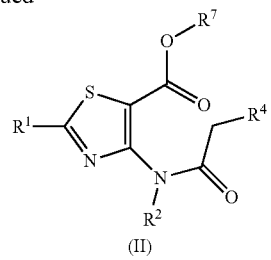

(II)

The free phenylacetic acids required for preparing the phenylacetic acid derivatives shown in Scheme 1a, i.e. those in which U is hydroxyl, are known or can be prepared by processes known per se and, for example, from WO 2005/075401, WO 2001/96277, WO 1996/35664 and WO 1996/25395. If $R^2$ represents a radical different from hydrogen, a radical $R^{2'}$ may be introduced by methods known from the literature, for example via reductive amination of a corresponding amino acid ester with an aldehyde followed by reduction for example with sodium cyanoborohydride. $R^{2'}$ represents $(C_1-C_6)$-alkyl, $(C_2-C_6)$-alkenyl, $(C_3-C_6)$-alkynyl, $(C_3-C_6)$-cycloalkyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl, $(C_3-C_6)$-cycloalkyl-$(C_1-C_6)$-alkyl, each of which is substituted by n halogen atoms. Furthermore, it is known that reactions with $R^{2'}$-halides or else corresponding sulfonates with appropriate amino acid esters lead to the desired precursors. Alternatively, it is also possible to carry out the alkylation with $R^{2'}$-halides or sulfonates after the condensation of the amino acid ester with the appropriate phenylacetic acid has taken place (see Scheme 1b), which then likewise leads to the intermediates (II) according to the invention.

Scheme 1b

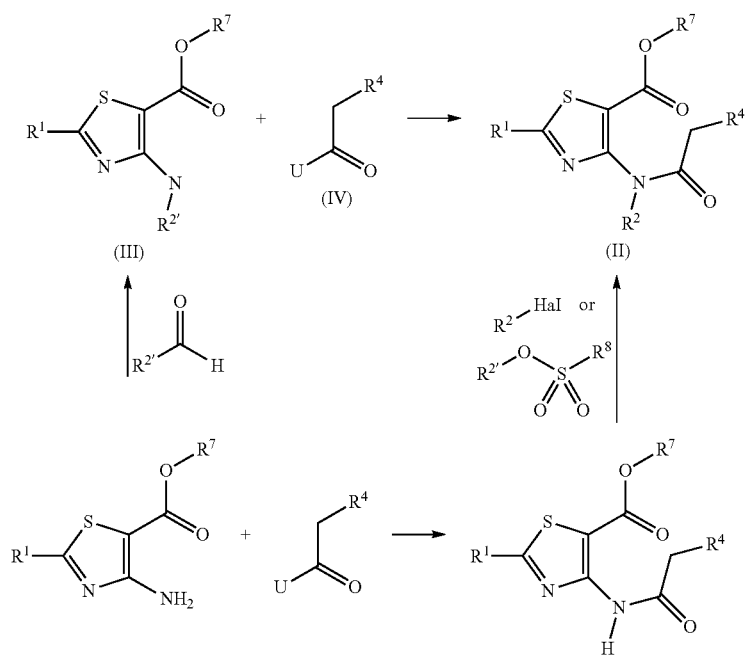

However, certain phenylacetic acid derivatives can also be prepared using acetate enolates in the presence of palladium catalysts formed, for example, from a palladium source (for example $Pd_2(dba)_3$ or $Pd(Oac)_2$) and a ligand (for example $(t-Bu)_3P$, iMes*HCl or 2'-(N,N-dimethylamino)-2-(dicyclohexylphosphanyl)biphenyl) (WO 2005/048710, J. Am. Chem. Soc 2002. 124, 12557, J. Am. Chem. Soc 2003. 125, 11176 or J. Am. Chem. Soc. 2001, 123, 799). In addition, certain substituted aryl halides can be converted under copper catalysis into the corresponding substituted malonic esters (described, for example, in Org. Lett. 2002, 2, 269, WO 2004/108727), which can be converted by known methods into phenylacetic acids. Compounds of the formula (I) according to the invention in which $R^3$ represents OH can also be prepared, for example, according to the method shown in Scheme 2 by reaction of compounds of the formula (I) in which $R^3$ represents alkoxy, preferably methoxy, with strong mineral bases such as sodium hydroxide or potassium hydroxide, or in concentrated mineral acids such as hydrobromic acid.

Scheme 2

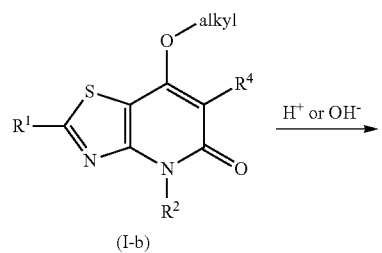

Compounds of the formula (I) according to the invention in which $R^3$ represents $O-C(=O)R^8$ can be prepared, for example, by reactions known to the person skilled in the art of compounds of the formula (I) in which $R^3$ represents hydrogen with carbonyl halides of the formula $Hal-CO-R^8$ or with carboxylic anhydrides of the formula $R^8-CO-O-CO-R^8$.

Compounds of the formula (I) according to the invention in which $R^3$ represents $O-C(=L)MR^9$ can be prepared, for example, by reactions known to the person skilled in the art of compounds of the formula (I) in which $R^3$ represents hydrogen with a) chloroformic esters or chloroformic thioesters of the formula $R^9-M-COOR^8$ or b) with chloroformyl halides or chlorothioformyl halides.

Compounds of the formula (I) according to the invention in which $R^3$ represents $SO_2R^{10}$ can be prepared, for example, by reactions known to the person skilled in the art of compounds of the formula (I) in which $R^3$ represents hydrogen with sulfonyl chlorides of the formula $R^{10}-SO_2-Cl$.

Compounds of the formula (I) according to the invention in which $R^3$ represents $P(=L)R^{11}R^{12}$ can be prepared, for example, by reactions known to the person skilled in the art of compounds of the formula (I) in which $R^3$ represents hydrogen with phosphoryl chlorides of the formula $Hal-P(=L)R^{11}R^{12}$.

Compounds of the formula (I) according to the invention in which $R^3$ represents E can be prepared, for example, by reactions known to the person skilled in the art of compounds of the formula (I) in which $R^3$ represents hydrogen with metal compounds of the formula $Met(OR^{13})_t$ or with amines. Here, Met is a monovalent or divalent metal ion, preferably an alkali metal or alkaline earth metal such as lithium, sodium, potassium, magnesium or calcium. The index t represents 1 or 2. An ammonium ion represents the group $NH_4^+$ or $R^{14}R^{15}R^{16}R^{17}N^+$ in which $R^{14}$, $R^{15}$, $R^{16}$ and $R^{17}$ independently of one another preferably represent $(C_1-C_6)$-alkyl or benzyl.

Compounds of the formula (I) according to the invention in which $R^3$ represents $C(=L)NR^{18}R^{19}$ can be prepared, for example, by reactions known to the person skilled in the art of compounds of the formula (I) in which $R^3$ represents hydrogen with isocyanates or isothiocyanates of the formula $R^{18}-N=C=L$ or with carbamoyl chlorides or thiocarbamoyl chlorides of the formula $R^{18}R^{19}N-C(=L)Cl$.

Compounds of the formula (I) according to the invention in which $R^3$ represents alkoxy, preferably methoxy, can also be prepared, for example, according to Scheme 3 by reactions known to the person skilled in the art of compounds of the formula (I-c) with compounds of the formula (V). Here, L represents bromine or iodine and Q represents a trialkyltin group, a magnesium halide group or preferably a boronic acid or an ester thereof. These reactions are usually carried out in the presence of a catalyst (for example Pd salts or Pd complexes) and in the presence of a base (for example sodium carbonate, potassium phosphate).

Scheme 3

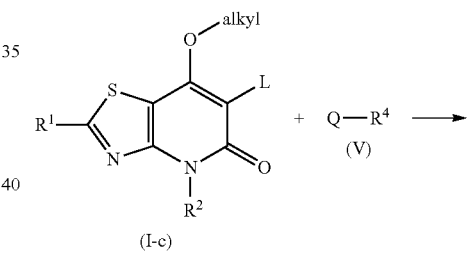

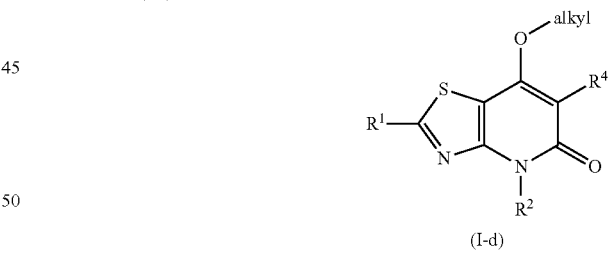

The compounds of the general formula (II-c) can be obtained by reacting the compounds of the general formula (II-b) with (het)arylboronic acids or (het)arylboronic esters under Suzuki conditions with a catalytic amount of a transition metal catalyst, preferably of a palladium catalyst, for example palladium(II) acetate, and of a ligand compound, preferably trialkylphosphine or triarylphosphine, for example tricyclohexylphosphine, and a base, preferably potassium tert-butoxide, trialkylamines or potassium carbonate or cesium carbonate or potassium phosphate, in an inert solvent (e.g. toluene or dimethylformamide, in each case optionally in a mixture with water (3:1)), at reaction temperatures between −20° C. and the reflux temperature of the solvent (Scheme 4).

Scheme 4

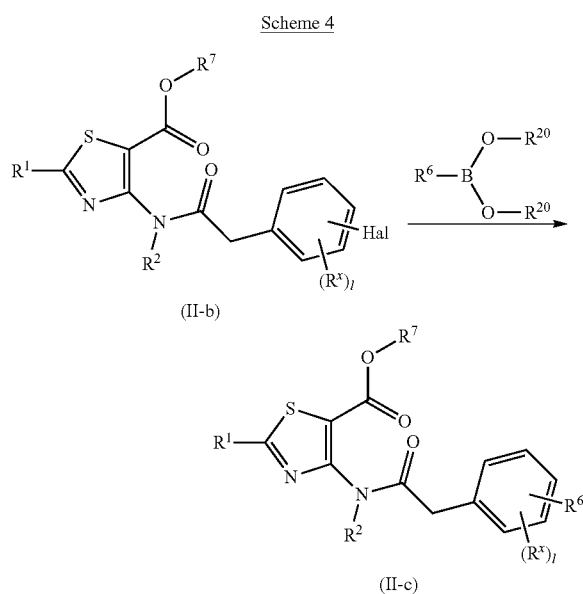

The workup of the respective reaction mixtures is generally effected by known processes, for example by crystallization, aqueous-extractive workup, by chromatographic methods or by a combination of these methods.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Neb. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds of the formula (I) according to the invention (and/or salts thereof), collectively referred to hereinafter as "compounds according to the invention", have excellent herbicidal efficacy against a broad spectrum of economically important monocotyledonous and dicotyledonous annual weed plants. The active compounds also have good control over perennial weed plants which are difficult to control and produce shoots from rhizomes, root stocks or other perennial organs.

The present invention therefore also provides a method for controlling unwanted plants or for regulating the growth of plants, preferably in plant crops, in which one or more compound(s) according to the invention is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The compounds according to the invention can be deployed, for example, prior to sowing (if appropriate also by incorporation into the soil), prior to emergence or after emergence. Specific examples of some representatives of the monocotyledonous and dicotyledonous weed flora which can be controlled by the compounds according to the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium,*

*Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing and eventually, after three to four weeks have elapsed, die completely.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. For these reasons, the present compounds are very suitable for the selective control of unwanted plant growth in plant crops such as agriculturally useful plants or ornamentals.

In addition, the compounds according to the invention (depending on their particular structure and the application rate deployed) have outstanding growth-regulating properties in crop plants. They intervene to regulate the plant's metabolism and can thus be used for controlled influence on plant constituents and to facilitate harvesting, for example by triggering desiccation and stunted growth. In addition, they are also suitable for general control and inhibition of unwanted vegetative growth without killing the plants. Inhibiting vegetative growth plays a major role for many monocotyledonous and dicotyledonous crops, since, for example, this can reduce or completely prevent lodging.

By virtue of their herbicidal and plant-growth-regulating properties, the active compounds can also be used for controlling harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferred, with respect to transgenic crops, to use the compounds according to the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Preference is given to the use of the compounds according to the invention or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the compounds according to the invention can be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

- recombinant modifications of crop plants for the purpose of modifying the starch synthesized in the plants (e.g. WO 92/11376, WO 92/14827, WO 91/19806),
- transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659),
- transgenic crop plants, for example cotton, with the ability to produce *Bacillus thuringiensis* toxins (Bt toxins) which make the plants resistant to particular pests (EP-A-0142924, EP-A-0193259),
- transgenic crop plants with a modified fatty acid composition (WO 91/13972),
- genetically modified crop plants with novel plant constituents or secondary metabolites, for example novel phytoalexins, which bring about an increased disease resistance (EPA 309862, EPA0464461),
- genetically modified plants with reduced photorespiration, which feature higher yields and higher stress tolerance (EPA 0305398),
- transgenic crop plants which produce pharmaceutically or diagnostically important proteins ("molecular pharming"),
- transgenic crop plants which are distinguished by higher yields or better quality
- transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

To carry out such recombinant manipulations, nucleic acid molecules which allow mutagenesis or a sequence change by recombination of DNA sequences can be introduced into plasmids. For example, base substitutions can be carried out, part-sequences can be removed, or natural or synthetic sequences may be added with the aid of standard methods.

For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

Preferably, the compounds according to the invention can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

On employment of the active compounds according to the invention in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds according to the invention as herbicides for control of weed plants in transgenic crop plants.

The compounds according to the invention can be applied in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and further additives, are likewise known and described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Technology], volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyrdiethyl, cyprosulfamide, isoxadifen-ethyl, cloquintocetmexyl and dichlormid.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To prepare the wettable powders, the herbicidally active compounds are ground finely, for example in customary apparatus such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may be, for example: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active substance onto adsorptive granular inert material or by applying active substance concentrates to the surface of carriers, such as sand, kaolinites or granular inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of compounds according to the invention.

In wettable powders, the active compound concentration is, for example, about 10 to 90% by weight, the remainder to 100% consisting of customary formulation constituents. In the case of emulsifiable concentrates, the active compound concentration can be from about 1 to 90, preferably from 5 to 80, % by weight. Formulations in the form of dusts comprise 1 to 30% by weight of active compound, preferably usually 5 to 20% by weight of active compound; sprayable solutions contain about 0.05 to 80, preferably 2 to 50, % by weight of active compound. In the case of water-dispersible granules, the active compound content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more active substance, but it is preferably between 0.005 and 750 g/ha.

The compounds according to the invention also display high insecticidal activities. Accordingly, the present invention further provides insecticidal compositions comprising compounds of the formula (I).

The examples below illustrate the invention.

A. CHEMICAL EXAMPLES

1. Preparation of 6-(4'-chloro-4-methylbiphenyl-3-yl)-7-hydroxy-4-(prop-2-yn-1-yl)[1,3]thiazolo[4,5-b]pyridin-5(4H)-one (compound I-a-40)

1.1. Preparation of methyl 4-{[(4'-chloro-4-methylbiphenyl-3-yl)acetyl]amino}-1,3-thiazole-5-carboxylate 1.8 g (11.38 mmol) of methyl 4-amino-1,3-thiazole-5-carboxylate were dissolved in 40 acetonitrile, and 1.8 ml (22.76 mmol) of pyridine were added. After 5 min of stirring at room temperature (RT), a solution of 3.18 g (11.38 mmol) of (4'-chloro-4-methylbiphenyl-3-yl)acetyl chloride (obtained from (4'-chloro-4-methylbiphenyl-3-yl)acetic acid according to WO 99/48869 A1) in 20 ml of acetonitrile was added dropwise. The mixture was stirred at RT for 12 h. The precipitate formed was filtered off, washed with water and dried under reduced pressure. The resulting mother liquor was concentrated by evaporation, dissolved in chloroform and chromatographed (ethyl acetate/n-heptane: 20/80 to 80/20). This gives a total of 1.81 g of methyl 4-{[(4'-chloro-4-methylbiphenyl-3-yl)acetyl]amino}-1,3-thiazole-5-carboxylate.

$^1$H NMR (400 MHz, CDCl$_3$): 9.78 (br s, 1H), 8.84 (s, 1H), 7.58 (m, 2H), 7.52 (m, 1H), 7.44 (m, 1H), 7.40 (m, 2H), 7.32 (m, 1H), 3.95 (br s, 2H), 3.76 (s, 3H), 2.42 (s, 3H).

1.2. Preparation of methyl 4-{[(4'-chloro-4-methylbiphenyl-3-yl)acetyl](prop-2-yn-1-yl)amino}-1,3-thiazole-5-carboxylate 600 mg (1.5 mmol) of methyl 4-{[(4'-chloro-4-methylbiphenyl-3-yl)acetyl]amino}-1,3-thiazole-5-carboxylate were dissolved in 20 ml of acetonitrile, and 1.2 g (3.7 mmol) of cesium carbonate, 449 mg (3 mmol) of sodium iodide and 0.33 ml (3 mmol, 80% pure) of propargyl bromide were added. The mixture was then stirred at RT for 12. The resulting suspension was filtered. The mother liquor was concentrated by evaporation. The residue was taken up in water and the solution was extracted with dichloromethane. The organic phase was dried and concentrated by evaporation. The residue was taken up in acetonitrile and chromatographed (acetonitrile/water (0.05% trifluoroacetic acid 20/80 to 100/0)). This gave 415 mg of methyl 4-{[(4'-chloro-4-methylbiphenyl-3-yl)acetyl](prop-2-yn-1-yl)amino}-1,3-thiazole-5-carboxylate.

$^1$H NMR (400 MHz, CDCl$_3$): 8.82 (s, 1H), 7.45 (m, 2H), 7.37 (m, 2H), 7.29 (m, 2H), 7.14 (m, 1H), 7.07 (br s, 1H), 4.64 (br d, 2H), 3.78 (s, 3H), 3.64 (br s, 2H), 2.20 (s, 3H), 2.14 (br s, 1H).

1.3 Preparation of 6-(4'-chloro-4-methylbiphenyl-3-yl)-7-hydroxy-4-(prop-2-yn-1-yl)[1,3]thiazolo[4,5-b]pyridin-5(4H)-one (compound I-a-40)

415 mg (0.95 mmol) of methyl 4-{[(4'-chloro-4-methylbiphenyl-3-yl)acetyl](prop-2-yn-1-yl)amino}-1,3-thiazole-5-carboxylate were dissolved in 15 ml of THF, and 34 mg (1.4 mmol) of NaH were added at RT. The reaction mixture was stirred at RT for 4 h. The THF was then removed under reduced pressure and the residue was taken up in water. The aqueous solution was washed with dichloromethane and then acidified with 1N hydrochloric acid. The mixture was then extracted with dichloromethane and the organic phase was dried and concentrated by evaporation. This gave 397 mg of 6-(4'-chloro-4-methylbiphenyl-3-yl)-7-hydroxy-4-(prop-2-yn-1-yl)[1,3]thiazolo[4,5-b]pyridin-5(4H)-one.

2. Preparation of O-[6-(4'-chloro-4-methylbiphenyl-3-yl)-5-oxo-4-(prop-2-yn-1-yl)-4,5-dihydro[1,3]thiazolo[4,5-b]pyridin-7-yl]S-methyl thiocarbonate (compound I-a-41)

150 mg (0.37 mmol) of 6-(4'-chloro-4-methylbiphenyl-3-yl)-7-hydroxy-4-(prop-2-yn-1-yl)[1,3]thiazolo[4,5-b]pyridin-5(4H)-one were dissolved in 15 ml of dichloromethane, and 0.05 ml (0.55 mmol) of pyridine and 1.3 ml (0.44 mmol) of S-methyl chloroformate were added. The mixture was then stirred at RT for 5 h. The dichloromethane was subsequently removed under reduced pressure and the residue was taken up in water. The aqueous solution was extracted with dichloromethane and the organic phase was dried and concentrated by evaporation. Chromatography (ethyl acetate/n-heptane: 20/80 to 80/20) gave 114 mg of O-[6-(4'-chloro-4-methylbiphenyl-3-yl)-5-oxo-4-(prop-2-yn-1-yl)-4,5-dihydro[1,3]thiazolo[4,5-b]pyridin-7-yl]S-methyl thiocarbonate.

3. Preparation of 6-(4'-chloro-4-methylbiphenyl-3-yl)-5-oxo-4-(prop-2-yn-1-yl)-4,5-dihydro[1,3]thiazolo[4,5]pyridin-7-yl2-methylpropanoate (compound I-a-42)

150 mg (0.37 mmol) of 6-(4'-chloro-4-methylbiphenyl-3-yl)-7-hydroxy-4-(prop-2-yn-1-yl)[1,3]thiazolo[4,5-b]pyridin-5(4H)-one were dissolved in 15 ml of dichloromethane, and 0.05 ml (0.55 mmol) of pyridine and then 47.1 mg (0.44 mmol) of 2-methylpropionyl chloride were added. After 4 h of stirring at RT, the reaction solution was washed with 2N hydrochloric acid and concentrated by evaporation. The residue was chromatographed: (acetonitrile/water (0.05% trifluoroacetic acid 20/80 to 100/0)). This gave 76 mg of 6-(4'-chloro-4-methylbiphenyl-3-yl)-5-oxo-4-(prop-2-yn-1-yl)-4,5-dihydro[1,3]thiazolo[4,5]pyridin-7-yl 2-methylpropanoate.

4. Preparation of 6-[2,6-dichloro-3-(5-chloro-2-thienyl)phenyl]-4-(2,2-difluoroethyl)-7-hydroxy[1,3]thiazolo[4,5-b]pyridin-5(4H)-one (compound I-a-14)

4.1. Preparation of methyl 4-{[(3-bromo-2,6-dichlorophenyl)acetyl]amino}-1,3-thiazole-5-carboxylate 2.0 g (12.64 mmol) of methyl 4-amino-1,3-thiazole-5-carboxylate were dissolved in 20 acetonitrile, and 2.05 ml (25.29 mmol) of pyridine were added. After 5 min of stirring at room temperature, a solution of 4.21 g (13.91 mmol) of (3-bromo-2,6-dichlorophenyl)acetyl chloride (obtained from (3-bromo-2,6-dichlorophenyl)acetic acid, see WO9736868) in 10 ml of acetonitrile was added dropwise. The reaction mixture was stirred at RT for 12 h. The precipitate formed was filtered off, washed with water and dried under reduced pressure. The resulting mother liquor was concentrated by evaporation, dissolved in chloroform and chromatographed (ethyl acetate/n-heptane: 20/80 to 80/20). This gives a total of 4.01 g of methyl 4-{[(3-bromo-2,6-dichlorophenyl)acetyl]amino}-1,3-thiazole-5-carboxylate.

$^1$H NMR (400 MHz; DMSO-d$_6$): 10.71 (br s, 1H), 9.22 (s, 1H), 7.76 (d, 1H), 7.47 (d, 1H), 4.23 (s, 2H), 3.76 (s, 3H).

4.2. Preparation of methyl 4-({[2,6-dichloro-3-(5-chloro-2-thienyl)phenyl]acetyl}amino)-1,3-thiazole-5-carboxylate 300 mg (0.71 mmol) of methyl 4-{[(3-bromo-2,6-dichlorophenyl)acetyl]amino}-1,3-thiazole-5-carboxylate and 230 mg (1.41 mmol) of (5-chloro-2-thienyl)boronic acid were dissolved in a mixture of 18 ml of toluene and 3 ml of water, and 450 mg (2.12 mmol) of potassium phosphate, 15.9 mg (0.07 mmol) of palladium acetate and 20 mg (0.07 mmol) of tricyclohexylphosphine were added in succession. With microwave irradiation, the reaction mixture was then heated at 180° C. for 1 h. The mixture was filtered and the filtrate was taken up in ethyl acetate and water. The organic phase was dried and concentrated by evaporation. This gave 170 mg of methyl 4-({[2,6-dichloro-3-(5-chloro-2-thienyl)phenyl]acetyl}amino)-1,3-thiazole-5-carboxylate, which were reacted further without further purification.

$^1$H NMR (400 MHz, CDCl$_3$): 9.80 (br s, 1H), 8.83 (s, 1H), 7.57 (m, 1H), 7.25 (m, 1H), 6.85 (d, 1H), 6.83 (d, 1H), 4.42 (br s, 2H), 3.87 (s, 3H).

4.3. Preparation of methyl 4-[{[2,6-dichloro-3-(5-chloro-2-thienyl)phenyl]acetyl}(2,2-difluoroethyl)amino]-1,3-thiazole-5-carboxylate Under an atmosphere of argon, 300 mg (0.65 mmol) of methyl 4-({[2,6-dichloro-3-(5-chloro-2-thienyl)phenyl]acetyl}amino)-1,3-thiazole-5-carboxylate were dissolved in 15 ml of tetrahydrofuran, and 23 mg (0.97 mmol) of sodium hydride were added at room temperature. The reaction mixture was stirred at RT for 5 min, and a solution of 167 mg (0.78 mmol) of 2,2-difluoroethyl trifluoromethanesulfonate in 6 ml of THF was then added over a period of 10 min. The mixture is then stirred at RT for 12 h. The THF is removed under reduced pressure and the residue is taken up in water. The aqueous phase is extracted with dichloromethane and the organic phase is dried and concentrated by evaporation. The residue is chromatographed (acetonitrile/water (0.05% trifluoroacetic acid 20/80 to 100/0)). This gave 120 mg of methyl 4-[{[2,6-dichloro-3-(5-chloro-2-thienyl)phenyl]acetyl}(2,2-difluoroethyl)amino]-1,3-thiazole-5-carboxylate.

$^1$H NMR (400 MHz, CDCl$_3$): 8.88 (s, 1H), 7.31 (d, 1H), 7.28 (d, 1H), 7.01 (d, 1H), 6.90 (d, 1H), 6.10 (tt, 1H), 4.12 (td, 2H), 3.95 (s, 3H), 3.93 (s, 2H).

4.4. Preparation of 6-[2,6-dichloro-3-(5-chloro-2-thienyl)phenyl]-4-(2,2-difluoroethyl)-7-hydroxy[1,3]thiazolo[4,5-b]pyridin-5(4H)-one (compound I-a-14)

120 mg (0.23 mmol) of methyl 4-[{[2,6-dichloro-3-(5-chloro-2-thienyl)phenyl]acetyl}(2,2- difluoroethyl)amino]-1,3-thiazole-5-carboxylate were dissolved in 10 ml of THF, and 6.6 mg (0.27 mmol) of sodium hydride were added under an atmosphere of argon. The reaction mixture was stirred at RT for 4 h. The THF was then removed under reduced pressure and the residue was taken up in water. The aqueous phase was extracted with dichloromethane, the organic phase was dried and concentrated by evaporation, the aqueous phase was acidified with 1N hydrochloric acid. After extraction with dichloromethane, the organic phase was dried and concentrated by evaporation. The product-containing residues were chromatographed (acetonitrile/water (0.05% trifluoroacetic acid) 20/80 to 100/0)). This gave 50 mg of 6-[2,6-dichloro-3-(5-chloro-2-thienyl)phenyl]-4-(2,2-difluoroethyl)-7-hydroxy[1,3]thiazolo[4,5-b]pyridin-5(4H)-one.

The compounds of the formula (I) listed in the tables below are obtained analogously to the preparation methods mentioned above. The abbreviations Me and Et represent methyl and ethyl.

TABLE 71

Compounds according to the invention in which R$^1$ represents hydrogen and the other substituents have the meanings listed in Table 71. R$^2$ represents methyl (a), 2,2-difluoroethyl (b), propargyl (c) or 2,2,2-trifluoroethyl (d). Ph represents phenyl.

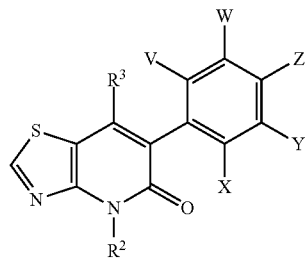

| No. | R$^2$ | R$^3$ | X | Y | Z | W | V | $^1$H NMR |
|---|---|---|---|---|---|---|---|---|
| I-a-1 | a | OH | Et | H | 2,4-Cl$_2$—Ph | H | Cl | |
| I-a-2 | b | OH | Et | H | 2,4-Cl$_2$—Ph | H | Cl | 400 MHz, CDCl$_3$: 8.97 (s, 1H), 7.50 (dd, 2H), 7.33 (3H), 6.29 (tt, 1H), 4.88 (m, 2H), 2.55 (m, 2H), 1.15 (t, 3H) |
| I-a-3 | c | OH | Et | H | 2,4-Cl$_2$—Ph | H | Cl | |
| I-a-4 | a | OH | Et | H | 5-Cl-thien-2-yl | H | Cl | |
| I-a-5 | b | OH | Et | H | 5-Cl-thien-2-yl | H | Cl | 400 MHz, DMSO-d$_6$: 11.43 (br s, 1H), 9.41 (s, 1H), 7.63 (d, 1H), 7.54 (d, 1H), 7.48 (d, 1H), 7.21 (d, 1H), 6.34 (tt, 1H), 4.75 (m, 2H), 2.42 (q, 2H), 1.04 (t, 3H) |
| I-a-6 | c | OH | Et | H | 5-Cl-thien-2-yl | H | Cl | 400 MHz, CDCl$_3$: 9.00 (s, 1H), 7.55 (d, 1H), 7.40 (d, 1H), 7.14 (d, 1H), 6.93 (d, 1H), 5.81 (br s, 1H), 5.29 (dd, 1H), 5.22 (dd, 1H), 2.54 (m, 2H), 2.22 (t, 1H), 1.15 (t, 3H) |
| I-a-7 | a | OH | Cl | 4-Cl—Ph | H | H | Cl | 400 MHz, DMSO-d$_6$: 11.36 (br s, 1H), 9.41 (s, 1H), 7.61 (d, 1H), 7.55 (m, 2H), 7.45 (m, 3H), 3.71 (s, 3H) |

TABLE 71-continued

Compounds according to the invention in which R¹ represents hydrogen and the other substituents have the meanings listed in Table 71. R² represents methyl (a), 2,2-difluoroethyl (b), propargyl (c) or 2,2,2-trifluoroethyl (d). Ph represents phenyl.

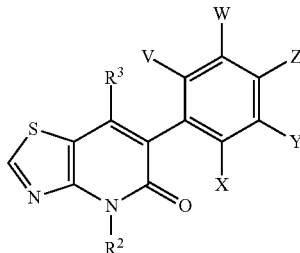

| No. | R² | R³ | X | Y | Z | W | V | ¹H NMR |
|---|---|---|---|---|---|---|---|---|
| I-a-8 | b | OH | Cl | 4-Cl—Ph | H | H | Cl | 400 MHz, CDCl₃: 8.94 (s, 1H), 7.42 (d, 1H), 7.35 (m, 2H), 7.25 (m, 3H), 6.22 (tt, 1H), 4.83 (td, 2H) |
| I-a-9 | c | OH | Cl | 4-Cl—Ph | H | H | Cl | 400 MHz, DMSO-d₆: 11.60 (br s, 1H), 9.45 (s, 1H) 7.62 (d, 1H), 7.55 (m, 2H), 7.46 (m, 3H), 5.05 (d, 2H), 3.16 (t, 1H) |
| I-a-10 | a | OH | Cl | 2,4-Cl₂—Ph | H | H | Cl | |
| I-a-11 | b | OH | Cl | 2,4-Cl₂—Ph | H | H | Cl | 400 MHz, CDCl₃: 8.97 (s, 1H), 7.56 (d, 1H), 7.51 (m, 1H), 7.31 (m, 3H), 6.27 (tt, 1H), 5.41 (br s, 1H), 4.87 (m, 2H) |
| I-a-12 | c | OH | Cl | 2,4-Cl₂—Ph | H | H | Cl | |
| I-a-13 | a | OH | Cl | 5-Cl-thien-2-yl | H | H | Cl | |
| I-a-14 | b | OH | Cl | 5-Cl-thien-2-yl | H | H | Cl | 400 MHz, CDCl₃: 8.98 (s, 1H), 7.52 (br s, 2H), 7.11 (d, 1H), 6.93 (d, 1H), 6.28 (tt, 1H), 4.87 (td, 2H) |
| I-a-15 | c | OH | Cl | 5-Cl-thien-2-yl | H | H | Cl | |
| I-a-16 | a | OH | Cl | 4-Cl—Ph | H | H | F | 400 MHz, DMSO-d₆: 11.48 (br s, 1H), 9.41 (s, 1H), 7.54 (m, 2H), 7.47 (m, 3H), 7.36 (t, 1H), 3.71 (s, 3H) |
| I-a-17 | b | OH | Cl | 4-Cl—Ph | H | H | F | 400 MHz, DMSO-d₆: 11.81 (br s, 1H), 9.44 s, 1H) 7.54 (m, 2H), 7.47 (m, 3H), 7.37 (t, 1H), 6.36 (tt, 1H), 4.75 (td, 2H) |
| I-a-18 | c | OH | Cl | 4-Cl—Ph | H | H | F | 400 MHz, DMSO-d₆: 11.71 (br s, 1H), 9.45 (s, 1H), 7.55 (m, 2H), 7.48 (m, 3H), 7.37 (t, 1H), 5.05 (d, 2H), 3.17 (t, 1H) |
| I-a-19 | a | OH | Cl | 2,4-Cl₂—Ph | H | H | F | 400 MHz, CDCl₃: 8.94 (s, 1H), 7.49 (d, 1H), 7.30 (m, 2H), 7.19 (m, 2H), 3.90 (s, 3H) |
| I-a-20 | b | OH | Cl | 2,4-Cl₂—Ph | H | H | F | 400 MHz, DMSO-d₆: 9.43 (s, 1H), 7.77 (dd, 1H), 7.54 (dt, 1H), 7.40 (m, 3H), 6.36 (tq, 1H), 4.74 (m, 2H) |
| I-a-21 | c | OH | Cl | 2,4-Cl₂—Ph | H | H | F | 400 MHz, CDCl₃: 9.01 (s, 1H), 7.54 (m, 1H), 7.35 (m, 2H), 7.25 (m, 2H), 5.25 (d, 2H), 2.23 (t, 1H) |

TABLE 71-continued

Compounds according to the invention in which $R^1$ represents hydrogen and the other substituents have the meanings listed in Table 71. $R^2$ represents methyl (a), 2,2-difluoroethyl (b), propargyl (c) or 2,2,2-trifluoroethyl (d). Ph represents phenyl.

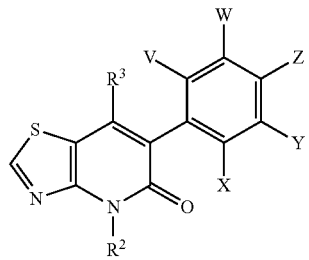

| No. | $R^2$ | $R^3$ | X | Y | Z | W | V | $^1$H NMR |
|---|---|---|---|---|---|---|---|---|
| I-a-22 | a | OH | Cl | 5-Cl-thien-2-yl | H | H | F | 400 MHz, DMSO-$d_6$: 11.51 (br s, 1H), 9.42 (s, 1H), 7.69 (dd, 1H), 3.66 (t, 1H), 7.27 (d, 1H), 7.21 (d, 1H), 3.71 (s, 3H) |
| I-a-23 | a | OC(O)OEt | Cl | 5-Cl-thien-2-yl | H | H | F | 400 MHz, CDCl$_3$: 8.99 (s, 1H), 7.50 (dd, 1H), 7.14 (t, 1H), 7.04 (d, 1H), 6.91 (d, 1H), 4.23 (q, 2H), 3.97 (s, 3H), 1.24 (t, 3H) |
| I-a-24 | b | OH | Cl | 5-Cl-thien-2-yl | H | H | F | 400 MHz, CDCl$_3$: 8.96 (s, 1H), 7.51 (dd, 1H), 7.14 (t, 1H), 7.02 (d, 1H), 6.91 (d, 1H), 6.25 (tt, 1H), 4.84 (td, 2H) |
| I-a-25 | c | OH | Cl | 5-Cl-thien-2-yl | H | H | F | 400 MHz, CDCl$_3$: 9.00 (s, 1H), 7.54 (dd, 1H), 7.16 (t, 1H), 7.04 (d, 1H), 6.91 (d, 1H), 5.24 (m, 2H), 2.23 (t, 1H) |
| I-a-26 | c | OC(O)OEt | Cl | 5-Cl-thien-2-yl | H | H | F | 400 MHz, CDCl$_3$: 9.04 (s, 1H), 7.50 (dd, 1H), 7.14 (t, 1H), 7.04 (d, 1H), 6.91 (d, 1H), 5.30 (s, 2H), 4.23 (q, 2H), 2.26 (t, 1H), 1.24 (t, 3H) |
| I-a-27 | a | OH | Et | H | 4-Cl—Ph | H | Cl | |
| I-a-28 | b | OH | Et | H | 4-Cl—Ph | H | Cl | 400 MHz, CDCl$_3$: 8.97 (s, 1H), 7.60 (d, 1H), 7.53 (m, 2H), 7.45 (m, 3H), 6.29 (tt, 1H), 5.80 (br s, 1H), 4.88 (m, 2H), 2.56 (m, 2H), 1.16 (t, 3H) |
| I-a-29 | c | OH | Et | H | 4-Cl—Ph | H | Cl | 400 MHz, CDCl$_3$: 9.00 (s, 1H), 7.59 (d, 1H), 7.53 (m, 2H), 7.45 (m, 3H), 5.84 (br s, 1H), 5.30 (dd, 1H), 5.22 (dd, 1H), 2.57 (m, 2H), 2.22 (t, 1H), 1.16 (t, 3H) |
| I-a-30 | a | OH | H | H | 4-Cl—Ph | H | Cl | 400 MHz, CDCl$_3$: 8.93 (s, 1H), 7.73 (d, 1H), 7.55 (dd, 1H), 7.51 (m, 2H), 7.44 (m, 2H), 6.11 (br s, 1H), 3.89 (s, 3H) |
| I-a-31 | b | OH | H | H | 4-Cl—Ph | H | Cl | 400 MHz, DMSO-$d_6$: 11.50 (br s, 1H), 9.42 (s, 1H), 7.83 (d, 1H), 7.79 (m, 2H), 7.68 (dd, 1H), 7.56 (m, 2H), 7.41 (d, 1H), 6.36 (tt, 1H), 4.75 (td, 2H) |

TABLE 71-continued

Compounds according to the invention in which R¹ represents hydrogen and the other substituents have the meanings listed in Table 71. R² represents methyl (a), 2,2-difluoroethyl (b), propargyl (c) or 2,2,2-trifluoroethyl (d). Ph represents phenyl.

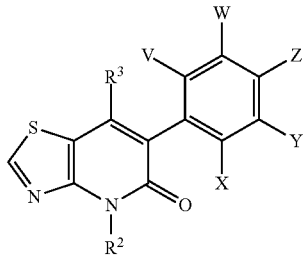

| No. | R² | R³ | X | Y | Z | W | V | ¹H NMR |
|---|---|---|---|---|---|---|---|---|
| I-a-32 | b | OCH₂—CHF₂ | H | H | 4-Cl—Ph | H | Cl | 400 MHz, CDCl₃: 8.97 (s, 1H), 7.59 (m, 2H), 7.55 (m, 1H), 7.52 (m, 1H), 7.50 (m, 1H), 7.41 (m, 2H), 6.30 (tt, 1H), 5.82 (tt, 1H), 4.88 (td, 2H), 3.92 (m, 2H) |
| I-a-33 | c | OH | H | H | 4-Cl—Ph | H | Cl | 400 MHz, CDCl₃: 9.00 (s, 1H), 7.75 (d, 1H), 7.58 (dd, 1H), 7.51 (m, 3H), 7.45 (m, 2H), 5.29 (dd, 1H), 2.60 (dd, 1H), 2.23 (t, 1H) |
| I-a-34 | a | OH | H | 4-Cl—Ph | H | H | Cl | 400 MHz, CDCl₃: 8.95 (s, 1H), 7.63 (m,1H), 7.57 (m, 2H), 7.49 (m, 2H), 7.39 (m, 2H), 5.95 (s, 1H), 3.91 (s, 3H) |
| I-a-35 | b | OH | H | 4-Cl—Ph | H | H | Cl | 400 MHz, CDCl₃: 8.96 (s, 1H), 7.64 (m, 1H), 7.58 (m, 2H), 7.49 (m, 2H), 7.40 (m, 2H), 6.29 (tt, 1H), 6.15 (br s, 1H), 4.86 (td, 2H) |
| I-a-36 | b | OC(O)SMe | H | 4-Cl—Ph | H | H | Cl | 400 MHz, CDCl₃: 8.99 (s, 1H), 7.57 (d, 1H), 7.53 (dd, 1H), 7.49 (m, 2H), 7.46 (m, 1H), 7.40 (m, 2H), 6.32 (tt, 1H), 4.92 (td, 2H), 2.28 (s, 3H) |
| I-a-37 | c | OH | H | 4-Cl—Ph | H | H | Cl | 400 MHz, DMSO-d₆: 11.40 (br s, 1H), 9.43 (s, 1H), 7.72 (m, 3H), 7.61 (m, 2H), 7.51 (m, 2H), 5.05 (d, 2H), 3.16 (t, 1H) |
| I-a-38 | a | OH | H | 4-Cl—Ph | H | H | Me | 400 MHz, CDCl₃: 8.93 (s, 1H), 7.53 (dd, 1H), 7.48 (m, 2H), 7.44 (m, 2H), 7.36 (m, 2H), 5.92 (br s, 1H), 3.91 (s, 3H), 2.25 (s, 3H) |
| I-a-39 | b | OH | H | 4-Cl—Ph | H | H | Me | 400 MHz, CDCl₃: 8.95 (s, 1H), 7.57 (dd, 1H), 7.51 (m, 2H), 7.46 (m, 2H), 7.39 (m, 2H), 6.30 (tt, 1H), 6.06 (br s, 1H), 4.88 (m, 2H), 2.26 (s, 3H) |
| I-a-40 | c | OH | H | 4-Cl—Ph | H | H | Me | 400 MHz, CDCl₃: 8.98 (s, 1H), 7.54 (m, 1H), 7.50 (m, 2H), 7.44 (m, 2H), 7.38 (m, 2H), 5.30 (s, 1H), 5.26 (dd, 2H), 2.26 (s, 3H), 2.23 (t, 3H) |

TABLE 71-continued

Compounds according to the invention in which $R^1$ represents hydrogen and the other substituents have the meanings listed in Table 71. $R^2$ represents methyl (a), 2,2-difluoroethyl (b), propargyl (c) or 2,2,2-trifluoroethyl (d). Ph represents phenyl.

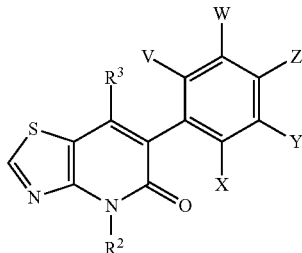

| No. | $R^2$ | $R^3$ | X | Y | Z | W | V | $^1$H NMR |
|---|---|---|---|---|---|---|---|---|
| I-a-41 | c | OC(O)SMe | H | 4-Cl—Ph | H | H | Me | 400 MHz, CDCl$_3$: 9.00 (s, 1H), 7.49 (m, 3H), 7.36 (m, 4H), 5.29 (d, 2H), 2.25 (t, 1H), 2.24 (s, 3H), 2.22 (s, 3H) |
| I-a-42 | c | OC(O)CMe$_2$ | H | 4-Cl—Ph | H | H | Me | 400 MHz, CDCl$_3$: 8.98 (s, 1H), 7.47 (m, 3H), 7.35 (m, 4H), 5.30 (d, 2H), 2.52 (spt, 1H), 2.26 (t, 1H), 2.23 (s, 3H), 0.92 (d, 3H), 0.90 (d, 3H) |
| I-a-43 | a | OC(O)OEt | Cl | 2,4-Cl$_2$—Ph | H | H | F | 400 MHz, CDCl$_3$: 8.98 (s, 1H), 7.51 (m, 1H), 7.30 (m, 3H), 7.18 (m, 1H), 4.20 (q, 2H), 3.97 (s, 3H), 1.23 (t, 3H) |
| I-a-44 | a | OC(O)SMe | Cl | 2,4-Cl$_2$—Ph | H | H | F | 400 MHz, CDCl$_3$: 8.98 (s, 1H), 7.51 (m, 1H), 7.30 (m, 3H), 7.19 (m, 1H), 3.97 (s, 3H), 2.32 (s, 3H) |
| I-a-45 | b | OH | Cl | 3-Cl—Ph | H | H | Cl | 400 MHz, DMSO-d$_6$: 9.43 (s, 1H), 7.60-7.30 (m, 6H), 6.34 (m, 1H), 4.75 (m, 2H) |
| I-a-46 | b | OH | Cl | Ph | H | H | Cl | 400 MHz, DMSO-d$_6$: 9.42 (s, 1H), 7.60 (d, 1H), 7.43 (m, 6H), 6.34 (m, 1H), 4.75 (m, 2H) |
| I-a-47 | d | OH | Cl | Ph | H | H | Cl | 400 MHz, DMSO-d$_6$: 9.43 (s, 1H), 7.61 (d, 1H), 7.43 (m, 6H), 5.14 (q, 2H) |
| I-a-48 | a | OH | Cl | Ph | H | H | Cl | 400 MHz, DMSO-d$_6$: 9.40 (s, 1H), 7.59 (d, 1H), 7.43 (m, 6H), 3.71 (s, 3H) |
| I-a-49 | b | OH | CF$_3$ | 4,5-dihydro-1,2-oxazol-3-yl | H | H | H | 400 MHz, DMSO-d$_6$: 11.48 (br s, 1H); 9.41 (s, 1H); 7.75 (t, 1H); 7.58 (d, 1H); 7.41 (d, 1H); 6.32 (tt, 1H); 4.73 (tt, 2H); 4.42 (t, 2H); 3.34 (t, 2H) |
| I-a-50 | b | OCH$_2$CHF$_2$ | CF$_3$ | 4,5-dihydro-1,2-oxazol-3-yl | H | H | H | 400 MHz, DMSO-d$_6$: 9.52 (s, 1H); 7.80 (t, 1H); 7.66 (d, 1H); 7.53 (d, 1H); 6.36 (tt, 1H); 6.12 (tt, 1H); 4.79 (tt, 2H); 4.43 (t, 2H); 9.63 (m, 2H); 3.35 (t, 2H) |

TABLE 72

Compounds according to the invention in which $R^1$ represents hydrogen. $R^2$ represents methyl (a), 2,2-difluoroethyl (b) or propargyl (c). Ph represents phenyl. Py represents pyridine.

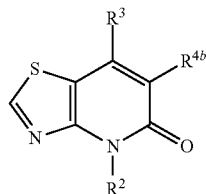

| No. | $R^2$ | $R^3$ | $R^{4b}$ | $^1$H NMR |
|---|---|---|---|---|
| I-b-1 | a | OH | 6-Cl—Py-3-yl | |
| I-b-2 | b | OH | 6-Cl—Py-3-yl | 400 MHz, DMSO-$d_6$: 11.79 (br s, 1H); 9.42 (s, 1H); 8.42 (dd, 1H; 7.89 (dd, 1H); 7.55 (dd, 1H); 6.37 (tt, 1H); 4.74 (td, 2H) |
| I-b-3 | c | OH | 6-Cl—Py-3-yl | |
| I-b-4 | a | OH | 4-Cl—Py-2-yl | |
| I-b-5 | b | OH | 4-Cl—Py-2-yl | |
| I-b-6 | c | OH | 4-Cl—Py-2-yl | |
| I-b-7 | a | OH | 2-Cl—Py-4-yl | |
| I-b-8 | b | OH | 2-Cl—Py-4-yl | |
| I-b-9 | c | OH | 2-Cl—Py-4-yl | |
| I-b-10 | a | OH | 4,6-Cl$_2$—Py-3-yl | |
| I-b-11 | b | OH | 4,6-Cl$_2$—Py-3-yl | |
| I-b-12 | c | OH | 4,6-Cl$_2$—Py-3-yl | |
| I-b-13 | a | OH | 2-Cl—Py-3-yl | |
| I-b-14 | b | OH | 2-Cl—Py-3-yl | 400 MHz, DMSO-$d_6$: 9.02 (s, 1H); 8.14 (dd, 1H); 7.65 (dd, 1H); 7.26 (dd, 1H); 6.26 (tt, 1H); 4.55 (td, 2H) |
| I-b-15 | c | OH | 2-Cl—Py-3-yl | |
| I-b-16 | a | OH | 5-Cl-3-CF$_3$—Py-2-yl | |
| I-b-17 | b | OH | 5-Cl-3-CF$_3$—Py-2-yl | 400 MHz, DMSO-$d_6$: 11.72 (br s, 1H); 9.45 (s, 1H); 9.00 (d, 1H); 8.46 (d, 1H); 6.32 (tt, 1H); 4.71 (td, 2H) |
| I-b-18 | c | OH | 5-Cl-3-CF$_3$—Py-2-yl | |
| I-b-19 | a | OH | 2-Cl-3-thiophenyl | |
| I-b-20 | b | OH | 2-Cl-3-thiophenyl | |
| I-b-21 | c | OH | 2-Cl-3-thiophenyl | |
| I-b-22 | a | OH | 5-Cl-2-thiophenyl | |
| I-b-23 | b | OH | 5-Cl-2-thiophenyl | |
| I-b-24 | c | OH | 5-Cl-2-thiophenyl | |
| I-b-25 | a | OH | 2-Cl-1,3-thiazol-5-yl | |
| I-b-26 | b | OH | 2-Cl-1,3-thiazol-5-yl | |
| I-b-27 | c | OH | 2-Cl-1,3-thiazol-5-yl | |
| I-b-28 | a | OH | 5-Cl-2-(4-Cl—Ph)-1,3-thiazol-4-yl | |
| I-b-29 | b | OH | 5-Cl-2-(4-Cl—Ph)-1,3-thiazol-4-yl | |
| I-b-30 | c | OH | 5-Cl-2-(4-Cl—Ph)-1,3-thiazol-4-yl | |
| I-b-31 | a | OH | 2-(2-Cl—Ph)-5-methyl-1,3-thiazol-4-yl | 400 MHz, CDCl$_3$: 8.92 (s, 1H), 7.97 (m, 1H), 7.53 (m, 2H), 7.38 (m, 1H), 3.93 (s, 3H), 2.65 (s, 3H) |
| I-b-32 | b | OH | 2-(2-Cl—Ph)-5-methyl-1,3-thiazol-4-yl | 400 MHz, CDCl$_3$: 8.93 (s, 1H), 7.97 (m, 1H), 7.54 (m, 1H), 7.39 (m, 2H), 6.31 (tt, 1H), 4.91 (td, 2H), 2.62 (s, 3H) |
| I-b-33 | c | OH | 2-(2-Cl—Ph)-5-methyl-1,3-thiazol-4-yl | |
| I-b-34 | a | OH | 5-Br-2-(4-Cl—Ph)-1,3-thiazol-4-yl | |
| I-b-35 | b | OH | 5-Br-2-(4-Cl—Ph)-1,3-thiazol-4-yl | 400 MHz, DMSO-$d_6$: 11.78 (br s, 1H); 9.46 (s, 1H); 7.93 (m, 2H); 7.59 (m, 2H); 6.38 (tt, 1H); 4.74 (td, 2H) |
| I-b-36 | c | OH | 5-Br-2-(4-Cl—Ph)-1,3-thiazol-4-yl | |
| I-b-37 | a | OH | 5-Cl-2-(4-Cl—Ph)-1,3-thiazol-4-yl | |
| I-b-38 | b | OH | 5-Cl-2-(4-Cl—Ph)-1,3-thiazol-4-yl | |
| I-b-39 | c | OH | 5-Cl-2-(4-Cl—Ph)-1,3-thiazol-4-yl | |
| I-b-40 | a | OH | 2-(4-Cl—Ph)-1,3-thiazol-4-yl | |
| I-b-41 | b | OH | 2-(4-Cl—Ph)-1,3-thiazol-4-yl | |

TABLE 72-continued

Compounds according to the invention in which $R^1$ represents hydrogen. $R^2$ represents methyl (a), 2,2-difluoroethyl (b) or propargyl (c). Ph represents phenyl. Py represents pyridine.

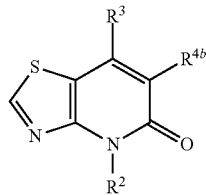

| No. | $R^2$ | $R^3$ | $R^{4b}$ | $^1$H NMR |
|---|---|---|---|---|
| I-b-42 | c | OH | 2-(4-Cl—Ph)-1,3-thiazol-4-yl | |
| I-b-43 | a | OH | 2-(3-Cl—Ph)-1,3-thiazol-4-yl | |
| I-b-44 | b | OH | 2-(3-Cl—Ph)-1,3-thiazol-4-yl | 400 MHz, CDCl$_3$: 14.91 (s, 1H), 8.97 (s, 1H), 8.77 (s, 1H), 7.92 (m, 1H), 7.81 (dt, 1H), 7.46 (m, 2H), 6.33 (tt, 1H), 4.93 (td, 2H) |
| I-b-45 | c | OH | 2-(3-Cl—Ph)-1,3-thiazol-4-yl | |
| I-b-46 | a | OH | 2-(4-Cl—Ph)-1,3-oxazol-4-yl | |
| I-b-47 | b | OH | 2-(4-Cl—Ph)-1,3-oxazol-4-yl | 400 MHz, DMSO-d$_6$: 14.81 (s, 1H), 9.52 (s, 1H), 8.77 (s, 1H), 8.03 (m, 2H), 7.66 (m, 2H), 6.44 (tt, 1H), 4.86 (td, 2H) |
| I-b-48 | c | OH | 2-(4-Cl—Ph)-1,3-oxazol-4-yl | |
| I-b-49 | a | OH | 5-(4-Cl—Ph)-1,2-oxazol-3-yl | |
| I-b-50 | b | OH | 5-(4-Cl—Ph)-1,2-oxazol-3-yl | |
| I-b-51 | c | OH | 5-(4-Cl—Ph)-1,2-oxazol-3-yl | |
| I-b-52 | a | OH | 5-chloro-3-methyl-1,2-oxazol-4-yl | |
| I-b-53 | b | OH | 5-chloro-3-methyl-1,2-oxazol-4-yl | 400 MHz, DMSO-d$_6$: 12.03 (br s, 1H), 9.45 (s, 1H), 6.37 (tt, 1H), 4.74 (td, 2H), 2.13 (s, 3H) |
| I-b-54 | c | OH | 5-chloro-3-methyl-1,2-oxazol-4-yl | |
| I-b-55 | a | OH | 3,5-dimethyl-1,2-oxazol-4-yl | |
| I-b-56 | b | OH | 3,5-dimethyl-1,2-oxazol-4-yl | |
| I-b-57 | c | OH | 3,5-dimethyl-1,2-oxazol-4-yl | |
| I-b-58 | a | OH | 4-nitro-1H-pyrazol-1-yl | |
| I-b-59 | b | OH | 4-nitro-1H-pyrazol-1-yl | 400 MHz, DMSO-d$_6$: 9.15 (s, 1H), 8.54 (d, 1H), 8.24 (d, 1H), 6.28 (tt, 1H), 4.55 (td, 2H) |
| I-b-60 | c | OH | 4-nitro-1H-pyrazol-1-yl | |
| I-b-61 | a | OH | 4-chloro-5-methyl-3-nitro-1H-pyrazol-1-yl | |
| I-b-62 | b | OH | 4-chloro-5-methyl-3-nitro-1H-pyrazol-1-yl | 400 MHz, DMSO-d$_6$: 9.52 (s, 1H); 6.37 (tt, 1H); 4.73 (m, 2H); 2.14 (s, 3H) |
| I-b-63 | c | OH | 4-chloro-5-methyl-3-nitro-1H-pyrazol-1-yl | |
| I-b-64 | a | OH | 4-chloro-3-cyclopropyl-1H-pyrazol-1-yl | |
| I-b-65 | b | OH | 4-chloro-3-cyclopropyl-1H-pyrazol-1-yl | |
| I-b-66 | c | OH | 4-chloro-3-cyclopropyl-1H-pyrazol-1-yl | |
| I-b-67 | a | OH | 3-(4-Cl—Ph)-5-methyl-1H-pyrazol-1-yl | |
| I-b-68 | b | OH | 3-(4-Cl—Ph)-5-methyl-1H-pyrazol-1-yl | 400 MHz, DMSO-d$_6$: 9.50 (s, 1H), 7.81 (m, 2H), 7.45 (m, 2H), 6.70 (d, 1H), 6.38 (tt, 1H), 4.74 (td, 2H), 2.09 (br s, 3H) |
| I-b-69 | b | O(CO)SMe | 3-(4-Cl—Ph)-5-methyl-1H-pyrazol-1-yl | 400 MHZ, CDCl$_3$: 9.04 (s, 1H), 7.73 (m, 2H), 7.35 (m, 2H), 6.47 (d, 1H), 6.28 (tt, 1H), 4.92 (m, 2H), 2.29 (d, 3H), 2.23 (s, 3H) |
| I-b-70 | b | O(CO)OEt | 3-(4-Cl—Ph)-5-methyl-1H-pyrazol-1-yl | 400 MHz, CDCl$_3$: 9.04 (s, 1H), 7.72 (m, 1H), 7.35 (m, 1H), 6.48 (d, 1H), 6.29 (tt, 1H), 5.93 (m, 2H), 4.09 (m, 2H), 2.31 (d, 3H), 1.09 (t, 3H) |
| I-b-71 | c | OH | 3-(4-Cl—Ph)-5-methyl-1H-pyrazol-1-yl | |
| I-b-72 | a | OH | 1-(5-Cl—Py-2-yl)-3,5-dimethyl-1H-pyrazol-4-yl | |
| I-b-73 | b | OH | 1-(5-Cl—Py-2-yl)-3,5-dimethyl-1H-pyrazol-4-yl | |
| I-b-74 | c | OH | 1-(5-Cl—Py-2-yl)-3,5-dimethyl-1H-pyrazol-4-yl | |
| I-b-75 | a | OH | 4-chloro-1H-pyrazol-1yl | |

TABLE 72-continued

Compounds according to the invention in which R¹ represents hydrogen. R² represents methyl (a), 2,2-difluoroethyl (b) or propargyl (c). Ph represents phenyl. Py represents pyridine.

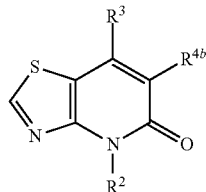

| No. | R² | R³ | R⁴ᵇ | ¹H NMR |
|---|---|---|---|---|
| I-b-76 | b | OH | 4-chloro-1H-pyrazol-1yl | 400 MHz, DMSO-d₆: 9.49 (s, 1H); 8.09 (d, 1H); 7.78 (d, 1H); 6.36 (tt, 1H); 4.73 (td, 2H) |
| I-b-77 | c | OH | 4-chloro-1H-pyrazol-1yl | |
| I-b-78 | a | OH | 1-(2,6-Cl₂-4-CF₃—Ph)-3,5-dimethyl-1H-pyrazol-4-yl | 400 MHz, CDCl₃: 8.95 (s, 1H), 7.78 (d, 1H), 7.74 (d, 1H), 3.93 (s, 3H), 2.25 (s, 3H), 2.02 (s, 3H) |
| I-b-79 | b | OH | 1-(2,6-Cl₂-4-CF₃—Ph)-3,5-dimethyl-1H-pyrazol-4-yl | 400 MHz, CDCl₃: 8.98 (s, 1H), 7.79 (d, 1H), 7.75 (d, 1H), 6.31 (tt, 1H), 4.90 (tdd, 2H), 2.26 (s, 3H), 2.03 (s, 3H) |
| I-b-80 | c | OH | 1-(2,6-Cl₂-4-CF₃—Ph)-3,5-dimethyl-1H-pyrazol-4-yl | 400 MHz, CDCl₃: 9.01 (s, 1H), 7.78 (d, 1H), 7.74 (d, 1H), 5.28 (m, 2H), 2.26 (s, 3H), 2.24 (t, 1H), 2.04 (s, 3H) |
| I-b-81 | c | OCH₂C≡CH | 1[2,6-Cl₂-4-CF₃-phenyl]-3,5-dimethyl-1H-pyrazol-4-yl | 400 MHz, CDCl₃: 8.97 (s, 1H), 7.77 (d, 1H), 7.74 (d, 1H), 5.28 (d, 2H), 4.55 (m, 2H), 2.45 (t, 2H), 2.26 (t, 1H), 2.25 (s, 3H), 2.05 (s, 3H) |
| I-b-82 | a | OH | 1-(2,6-Cl₂-4-OCF₃—Ph)-3,5-dimethyl-1H-pyrazol-4-yl | 400 MHz, CDCl₃: 8.96 (s, 1H), 7.40 (m, 1H), 7.37 (m, 1H), 3.93 (s, 3H), 2.25 (s, 3H), 2.02 (s, 3H) |
| I-b-83 | b | OH | 1-(2,6-Cl₂-4-OCF₃—Ph)-3,5-dimethyl-1H-pyrazol-4-yl | 400 MHz, CDCl₃: 8.96 (s, 1H), 7.41 (d, 1H), 7.37 (d, 1H), 6.31 (tt, 1H), 4.89 (tdd, 2H), 2.25 (s, 3H), 2.02 (s, 3H) |
| I-b-84 | c | OH | 1-(2,6-Cl₂-4-OCF₃—Ph)-3,5-dimethyl-1H-pyrazol-4-yl | 400 MHz, CDCl₃: 9.00 (s, 1H), 7.40 (m, 1H), 7.37 (m, 1H), 5.27 (m, 2H), 2.25 (s, 3H), 2.24 (t, 1H), 2.03 (s, 3H) |
| I-b-85 | c | OCH₂C≡CH | 1-(2,6-Cl₂-4-OCF₃—Ph)-3,5-dimethyl-1H-pyrazol-4-yl | 400 MHz, CDCl₃: 8.96 (s, 1H), 7.40 (d, 1H), 7.37 (d, 1H), 5.27 (d, 2H), 4.54 (m, 2H), 2.45 (t, 1H), 2.26 (t, 1H), 2.26 (s, 3H), 2.05 (s, 3H) |
| I-b-86 | a | OH | 4-Cl-5-methyl-3-CF₃-1H-pyrazol-1-yl | 400 MHz, CDCl₃: 8.98 (s, 1H); 3.87 (s, 3H); 2.27 (s, 3H) |
| I-b-87 | b | OH | 4-Cl-5-methyl-3-CF₃-1H-pyrazol-1-yl | 400 MHz, DMSO-d₆: 9.52 (s, 1H); 6.37 (tt, 1H); 4.72 (m, 2H); 2.10 (s, 3H) |
| I-b-88 | c | OH | 4-Cl-5-methyl-3-CF₃-1H-pyrazol-1-yl | |
| I-b-89 | a | OH | 5-methyl-3-CF₃-1H-pyrazol-1-yl | 400 MHz, DMSO-d₆: 9.50 (s, 1H); 6.64 (s, 1H); 3.71 (s, 3H); 2.10 (s, 3H) |
| I-b-90 | b | OH | 5-methyl-3-CF₃-1H-pyrazol-1-yl | 400 MHz, DMSO-d₆: 9.51 (s, 1H); 6.64 (s, 1H); 6.38 (tt, 1H); 4.73 (td, 2H); 2.10 (s, 3H) |
| I-b-91 | c | OH | 5-methyl-3-CF₃-1H-pyrazol-1-yl | |
| I-b-92 | a | OH | 3,5-bis(trifluoromethyl)-1H-pyrazol-1-yl | 400 MHz, DMSO-d₆: 9.53 (s, 1H); 7.71 (s, 1H); 3.70 (s, 3H) |

TABLE 72-continued

Compounds according to the invention in which R¹ represents hydrogen. R² represents methyl (a), 2,2-difluoroethyl (b) or propargyl (c). Ph represents phenyl. Py represents pyridine.

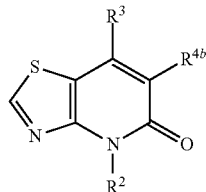

| No. | R² | R³ | R⁴ᵇ | ¹H NMR |
|---|---|---|---|---|
| I-b-93 | b | OH | 3,5-bis(trifluoromethyl)-1H-pyrazol-1-yl | 400 MHz, DMSO-d₆: 9.54 (s, 1H); 7.71 (s, 1H); 6.35 (tt, 1H); 4.72 (m, 2H) |
| I-b-94 | c | OH | 3,5-bis(trifluoromethyl)-1H-pyrazol-1-yl | |
| I-b-95 | a | OH | 3,5-bis(difluoromethyl)-1H-pyrazol-1-yl | 400 MHz, DMSO-d₆: 9.51 (s, 1H); 7.08 (t, 1H); 7.03 (s, 1H); 6.91 (t, 1H); 3.70 (s, 3H) |
| I-b-96 | b | OH | 3,5-bis(difluoromethyl)-1H-pyrazol-1-yl | 400 MHz, DMSO-d₆: 9.51 (s, 1H); 7.08 (t, 1H); 7.03 (s, 1H); 6.92 (t, 1H); 6.35 (tt, 1H); 4.71 (td, 2H) |
| I-b-97 | c | OH | 3,5-bis(difluoromethyl)-1H-pyrazol-1-yl | |
| I-b-98 | a | OH | 4-nitro-1H-imidazol-1yl | |
| I-b-99 | b | OH | 4-nitro-1H-imidazol-1yl | |
| I-b-100 | c | OH | 4-nitro-1H-imidazol-1yl | |
| I-b-101 | a | OH | 4,5-Cl₂-1H-imidazol-1yl | |
| I-b-102 | b | OH | 4,5-Cl₂-1H-imidazol-1yl | |
| I-b-103 | c | OH | 4,5-Cl₂-1H-imidazol-1yl | |
| I-b-104 | a | OH | 3-(2-Cl—Ph)-1,2,4-oxadiazol-5-yl | |
| I-b-105 | b | OH | 3-(2-Cl—Ph)-1,2,4-oxadiazol-5-yl | |
| I-b-106 | c | OH | 3-(2-Cl—Ph)-1,2,4-oxadiazol-5-yl | |
| I-b-107 | a | OH | 3-(3-Cl—Ph)-1,2,4-oxadiazol-5-yl | |
| I-b-108 | b | OH | 3-(3-Cl—Ph)-1,2,4-oxadiazol-5-yl | |
| I-b-109 | c | OH | 3-(3-Cl—Ph)-1,2,4-oxadiazol-5-yl | |
| I-b-110 | a | OH | 5-(3-Cl—Ph)-1,3,4-oxadiazol-2-yl | |
| I-b-111 | b | OH | 5-(3-Cl—Ph)-1,3,4-oxadiazol-2-yl | |
| I-b-112 | c | OH | 5-(3-Cl—Ph)-1,3,4-oxadiazol-2-yl | |
| I-b-113 | a | OH | 1H-1,2,4-triazol-1-yl | |
| I-b-114 | b | OH | 1H-1,2,4-triazol-1-yl | |
| I-b-115 | c | OH | 1H-1,2,4-triazol-1-yl | |
| I-b-116 | a | OH | 1-(2,4-Cl₂—Ph)-1H-1,2,3-triazol-5-yl | 400 MHz, CDCl₃: 8.93 (s, 1H), 7.63 (d, 1H), 7.48 (m, 2H), 7.35 (dd, 1H), 3.68 (s, 3H) |
| I-b-117 | b | OH | 1-(2,4-Cl₂—Ph)-1H-1,2,3-triazol-5-yl | |
| I-b-118 | b | OC(O)OEt | 1-(2,4-Cl₂—Ph)-1H-1,2,3-triazol-5-yl | 400 MHz, CDCl₃: 9.00 (s, 1H), 7.90 (s, 1H), 7.52 (br s, 1H), 7.50 (d, 1H), 7.30 (dd, 1H), 5.98 (tt, 1H), 4.74 (td, 2H), 4.29 (q, 2H), 1.35 (t, 3H) |
| I-b-119 | c | OH | 1-(2,4-Cl₂—Ph)-1H-1,2,3-triazol-5-yl | |
| I-b-120 | a | OH | 3-(4-Cl—Ph)-1-ethyl-1H-1,2,4-triazol-5-yl | 400 MHz, DMSO-d₆: 9.48 (s, 1H); 8.03 (m, 2H); 7.54 (m, 2H); 4.01 (q, 2H); 3.71 (s, 3H); 1.37 (t, 3H) |
| I-b-121 | b | OH | 3-(4-Cl—Ph)-1-ethyl-1H-1,2,4-triazol-5-yl | 400 MHz, DMSO-d₆: 9.48 (s, 1H), 8.04 (m, 2H), 7.55 (m, 2H), 6.37 (tt, 1H), 4.73 (td, 2H), 4.04 (q, 2H), 1.37 (t, 3H) |
| I-b-122 | c | OH | 3-(4-Cl—Ph)-1-ethyl-1H-1,2,4-triazol-5-yl | 400 MHz, CDCl₃: 9.02 (s, 1H), 8.01 (br d, 2H), 7.43 (br d, 2H), 5.24 (d, 2H), 4.60 (q, 2H), 2.25 (t, 1H), 1.56 (t, 3H) |
| I-b-123 | a | OH | 1H-tetrazol-1-yl | |
| I-b-124 | b | OH | 1H-tetrazol-1-yl | |
| I-b-125 | c | OH | 1H-tetrazol-1-yl | |

TABLE 72-continued

Compounds according to the invention in which R¹ represents hydrogen. R² represents methyl (a), 2,2-difluoroethyl (b) or propargyl (c). Ph represents phenyl. Py represents pyridine.

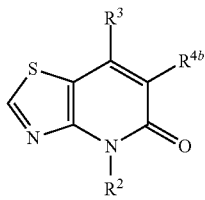

| No. | R² | R³ | R⁴ᵇ | ¹H NMR |
|---|---|---|---|---|
| I-b-126 | b | OCH₂CHF₂ | 3,5-bis(difluoromethyl)-1-H-pyrazol-1-yl | 400 MHz, DMSO-d₆: 9.64 (s, 1H); 7.19 (s, 1H); 7.14 (t, 1H); 7.06 (t, 1H); 6.40 (tt, 1H); 6.25 (tt, 1H); 4.78 (tt, 2H); 4.13 (m, 2H) |
| I-b-127 | b | OCH₂CHF₂ | 4-chloro-1-H-pyrazol-1-yl | 400 MHz, DMSO-d₆: 9.57 (s, 1H); 8.17 (d, 1H); 7.90 (d, 1H); 6.40 (tt, 1H); 6.25 (tt, 1H); 4.77 (td, 2H); 3.98 (td, 2H) |
| I-b-128 | b | OCH₂CHF₂ | 5-Cl-3-CF₃—Py-2-yl | 400 MHz, DMSO-d₆: 9.57 (s, 1H); 9.05 (d, 1H); 8.55 (d, 1H); 6.36 (tt, 1H); 6.13 (tt, 1H); 4.78 (m, 2H); 4.28 (m, 2H) |
| I-b-129 | a | OH | 3-Ph-5-methyl-1H-pyrazol-1-yl | 400 MHz, DMSO-d₆: 9.50 (s, 1H); 7.78 (m, 2H); 7.40 (m, 2H); 7.29 (m, 1H); 6.66 (d, 1H); 3.72 (s, 3H); 2.09 (d, 3H) |
| I-b-130 | b | OH | 3-Ph-5-methyl-1H-pyrazol-1-yl | 400 MHz, DMSO-d₆: 9.50 (s, 1H); 7.78 (m, 2H); 7.40 (m, 2H); 7.30 (m, 1H); 6.68 (d, 1H); 6.38 (tt, 1H); 4.75 (td, 2H); 2.10 (d, 3H) |
| I-b-131 | c | OH | 3-Ph-5-methyl-1H-pyrazol-1-yl | 400 MHz, DMSO-d₆: 9.52 (s, 1H); 7.79 (m, 2H); 7.40 (m, 2H); 7.30 (m, 1H); 6.68 (d, 1H); 5.05 (d, 2H); 3.20 (t, 1H); 2.09 (d, 3H) |
| I-b-132 | a | OH | 3-(4-Cl—Ph)-5-ethyl-1H-pyrazol-1-yl | 400 MHz, DMSO-d₆: 9.48 (s, 1H); 7.83 (m, 2H); 7.45 (m, 2H); 6.72 (br s, 1H); 3.71 (s, 3H); 2.40 (m, 2H); 1.16 (t, 3H) |
| I-b-133 | b | OH | 3-(4-Cl—Ph)-5-ethyl-1H-pyrazol-1-yl | 400 MHz, DMSO-d₆: 9.50 (s, 1H); 7.83 (m, 2H); 7.45 (m, 2H); 6.73 (br s, 1H); 6.37 (tt, 1H); 4.73 (td, 2H); 2.40 (br q, 2H); 1.16 (t, 3H) |
| I-b-134 | c | OH | 3-(4-Cl—Ph)-5-ethyl-1H-pyrazol-1-yl | 400 MHz, DMSO-d₆: 9.52 (s, 1H); 7.83 (m, 2H); 7.45 (m, 2H); 6.74 (br s, 1H); 5.04 (d, 2H); 3.20 (t, 1H); 2.39 (q, 2H); 1.16 (t, 3H) |
| I-b-135 | a | OH | 3-(4-Cl—Ph)-5-propyl-1H-pyrazol-1-yl | 400 MHz, DMSO-d₆: 9.48 (s, 1H); 7.83 (m, 2H); 7.44 (m, 2H); 6.72 (s, 1H); 3.71 (s, 3H); 2.35 (br t, 2H); 1.59 (sxt, 2H); 0.90 (t, 3H) |
| I-b-136 | b | OH | 3-(4-Cl—Ph)-5-propyl-1H-pyrazol-1-yl | 400 MHz, DMSO-d₆: 9.50 (s, 1H); 7.83 (m, 2H); 7.45 (m, 2H); 6.73 (s, 1H); 6.37 (tt, 1H); 4.74 (td, 2H); 2.36 (t, 2H); 1.58 (sxt, 2H); 0.90 (t, 3H) |

TABLE 72-continued

Compounds according to the invention in which R¹ represents hydrogen. R² represents methyl (a), 2,2-difluoroethyl (b) or propargyl (c). Ph represents phenyl. Py represents pyridine.

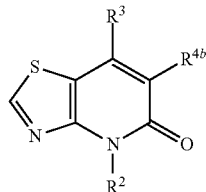

| No. | R² | R³ | R⁴ᵇ | ¹H NMR |
|---|---|---|---|---|
| I-b-137 | c | OH | 3-(4-Cl—Ph)-5-propyl-1H-pyrazol-1-yl | 400 MHz, DMSO-d₆: 8.89 (s, 1H); 7.33 (m, 2H); 7.21 (m, 2H); 6.43 (br s, 1H); 4.87 (br s, 2H); 2.49 (t, 2H); 2.19 (t, 1H); 1.66 (sxt, 2H); 0.99 (t, 3H) |
| I-b-138 | a | OH | 3-(3-Cl—Ph)-5-methyl-1H-pyrazol-1-yl | 400 MHz, DMSO-d₆: 9.48 (s, 1H); 7.81 (m, 1H); 7.75 (m, 1H); 7.43 (t, 1H); 7.35 (m, 1H); 6.75 (d, 1H); 3.71 (s, 3H); 2.09 (d, 3H) |
| I-b-139 | b | OH | 3-(3-Cl—Ph)-5-methyl-1H-pyrazol-1-yl | 400 MHz, DMSO-d₆: 9.51 (s, 1H); 7.82 (m, 1H); 7.75 (m, 1H); 7.44 (t, 1H); 7.35 (m, 1H); 6.76 (d, 1H); 6.38 (tt, 1H); 4.75 (td, 2H); 2.10 (d, 3H) |
| I-b-140 | c | OH | 3-(3-Cl—Ph)-5-methyl-1H-pyrazol-1-yl | 400 MHz, DMSO-d₆: 9.53 (s, 1H); 7.82 (br t, 1H); 7.76 (dt, 1H); 7.44 (t, 1H); 7.36 (m, 1H); 6.76 (d, 1H); 5.05 (d, 2H); 3.21 (t, 1H); 2.09 (d, 3H) |
| I-b-141 | a | OH | 3-(3,4-Cl₂—Ph)-5-methyl-1H-pyrazol-1-yl | |
| I-b-142 | b | OH | 3-(3,4-Cl₂—Ph)-5-methyl-1H-pyrazol-1-yl | 400 MHz, DMSO-d₆: 9.50 (s, 1H); 8.00 (d, 1H); 7.79 (dd, 1H); 7.66 (d, 1H); 6.80 (d, 1H); 6.38 (tt, 1H); 4.74 (td, 2H); 2.10 (d, 3H) |
| I-b-143 | c | OH | 3-(3,4-Cl₂—Ph)-5-methyl-1H-pyrazol-1-yl | |
| I-b-144 | a | OH | 3-(4-Br—Ph)-5-methyl-1H-pyrazol-1-yl | 400 MHz, DMSO-d₆: 9.48 (s, 1H); 7.74 (m, 2H); 7.58 (m, 2H); 6.69 (d, 1H); 3.71 (s, 3H); 2.08 (d, 3H) |
| I-b-145 | b | OH | 3-(4-Br—Ph)-5-methyl-1H-pyrazol-1-yl | 400 MHz, DMSO-d₆: 9.50 (s, 1H); 7.75 (m, 2H); 7.59 (m, 2H); 6.70 (d, 1H); 6.38 (tt, 1H); 4.74 (td, 2H); 2.09 (d, 3H) |
| I-b-146 | c | OH | 3-(4-Br—Ph)-5-methyl-1H-pyrazol-1-yl | |
| I-b-147 | a | OH | 3-(3-Br—Ph)-5-methyl-1H-pyrazol-1-yl | |
| I-b-148 | b | OH | 3-(3-Br—Ph)-5-methyl-1H-pyrazol-1-yl | |
| I-b-149 | c | OH | 3-(3-Br—Ph)-5-methyl-1H-pyrazol-1-yl | 400 MHz, DMSO-d₆: 9.52 (s, 1H); 7.75 (m, 2H); 7.58 (m, 2H); 6.70 (d, 1H); 5.05 (d, 2H); 3.20 (t, 1H); 2.09 (d, 3H) |
| I-b-150 | a | OH | 3-(4-CF₃—Ph)-5-methyl-1H-pyrazol-1-yl | |
| I-b-151 | b | OH | 3-(4-CF₃—Ph)-5-methyl-1H-pyrazol-1-yl | 400 MHz, DMSO-d₆: 9.50 (s, 1H); 8.00 (m, 2H); 7.75 (m, 2H); 6.81 (d, 1H); 6.39 (tt, 1H); 4.75 (td, 2H); 2.11 (d, 3H) |
| I-b-152 | c | OH | 3-(4-CF₃—Ph)-5-methyl-1H-pyrazol-1-yl | |
| I-b-153 | a | OH | 3-(3-CF₃—Ph)-5-methyl-1H-pyrazol-1-yl | |
| I-b-154 | b | OH | 3-(3-CF₃—Ph)-5-methyl-1H-pyrazol-1-yl | 400 MHz, DMSO-d₆: 9.51 (s, 1H); 8.09 (m, 2H); 7.66 (m, 2H); 6.84 (d, 1H); 6.39 (tt, 1H); 4.75 (td, 2H); 2.11 (d, 3H) |
| I-b-155 | c | OH | 3-(3-CF₃—Ph)-5-methyl-1H-pyrazol-1-yl | |
| I-b-156 | a | OH | 1-methyl-3-Ph-1H-1,2,4-triazol-5-yl | |

TABLE 72-continued

Compounds according to the invention in which R¹ represents hydrogen. R² represents methyl (a), 2,2-difluoroethyl (b) or propargyl (c). Ph represents phenyl. Py represents pyridine.

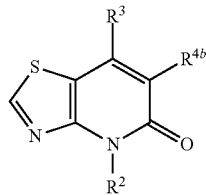

| No. | R² | R³ | R⁴ᵇ | ¹H NMR |
|---|---|---|---|---|
| I-b-157 | b | OH | 1-methyl-3-Ph-1H-1,2,4-triazol-5-yl | |
| I-b-158 | c | OH | 1-methyl-3-Ph-1H-1,2,4-triazol-5-yl | |
| I-b-159 | a | OH | 1-ethyl-3-Ph-1H-1,2,4-triazol-5-yl | |
| I-b-160 | b | OH | 1-ethyl-3-Ph-1H-1,2,4-triazol-5-yl | |
| I-b-161 | c | OH | 1-ethyl-3-Ph-1H-1,2,4-triazol-5-yl | |
| I-b-162 | a | OH | 1-cyclopropyl-3-Ph-1H-1,2,4-triazol-5-yl | |
| I-b-163 | b | OH | 1-cyclopropy-3-Ph-1H-1,2,4-triazol-5-yl | |
| I-b-164 | c | OH | 1-cyclopropy-3-Ph-1H-1,2,4-triazol-5-yl | |
| I-b-165 | a | OH | 3-(2-Cl—Ph)-1-methyl-1H-1,2,4-triazol-5-yl | |
| I-b-166 | b | OH | 3-(2-Cl—Ph)-1-methyl-1H-1,2,4-triazol-5-yl | |
| I-b-167 | c | OH | 3-(2-Cl—Ph)-1-methyl-1H-1,2,4-triazol-5-yl | |
| I-b-168 | a | OH | 3-(2-Cl—Ph)-1-ethyl-1H-1,2,4-triazol-5-yl | |
| I-b-169 | b | OH | 3-(2-Cl—Ph)-1-ethyl-1H-1,2,4-triazol-5-yl | |
| I-b-170 | c | OH | 3-(2-Cl—Ph)-1-ethyl-1H-1,2,4-triazol-5-yl | |
| I-b-171 | a | OH | 3-(2-Cl—Ph)-1-cyclopropyl-1H-1,2,4-triazol-5-yl | |
| I-b-172 | b | OH | 3-(2-Cl—Ph)-1-cyclopropyl-1H-1,2,4-triazol-5-yl | |
| I-b-173 | c | OH | 3-(2-Cl—Ph)-1-cyclopropyl-1H-1,2,4-triazol-5-yl | |
| I-b-174 | a | OH | 3-(3-Cl—Ph)-1-methyl-1H-1,2,4-triazol-5-yl | |
| I-b-175 | b | OH | 3-(3-Cl—Ph)-1-methyl-1H-1,2,4-triazol-5-yl | |
| I-b-176 | c | OH | 3-(3-Cl—Ph)-1-methyl-1H-1,2,4-triazol-5-yl | |
| I-b-177 | a | OH | 3-(3-Cl—Ph)-1-ethyl-1H-1,2,4-triazol-5-yl | |
| I-b-178 | b | OH | 3-(3-Cl—Ph)-1-ethyl-1H-1,2,4-triazol-5-yl | 400 MHz, DMSO-$d_6$: 9.49 (s, 1H); 8.01 (m, 1H); 7.99 (dt, 1H); 7.53 (td, 1H); 7.54 (dt, 1H); 6.37 (tt, 1H); 4.74 (td, 2H); 4.04 (q, 2H); 1.38 (t, 3H) |
| I-b-179 | c | OH | 3-(3-Cl—Ph)-1-ethyl-1H-1,2,4-triazol-5-yl | 400 MHz, DMSO-$d_6$: 9.51 (s, 1H); 7.99 (m, 2H); 7.51 (m, 2H); 5.05 (d, 2H); 4.03 (q, 2H); 3.20 (t, 1H); 1.38 (t, 3H) |
| I-b-180 | a | OH | 3-(3-Cl—Ph)-1-cyclopropyl-1H-1,2,4-triazol-5-yl | |
| I-b-181 | b | OH | 3-(3-Cl—Ph)-1-cyclopropyl-1H-1,2,4-triazol-5-yl | |
| I-b-182 | c | OH | 3-(3-Cl—Ph)-1-cyclopropyl-1H-1,2,4-triazol-5-yl | |
| I-b-183 | a | OH | 3-(4-Cl—Ph)-1-methyl-1H-1,2,4-triazol-5-yl | |
| I-b-184 | b | OH | 3-(4-Cl—Ph)-1-methyl-1H-1,2,4-triazol-5-yl | |
| I-b-185 | c | OH | 3-(4-Cl—Ph)-1-methyl-1H-1,2,4-triazol-5-yl | |
| I-b-186 | a | OH | 3-(4-Cl—Ph)-1-cyclopropylyl-1H-1,2,4-triazol-5-yl | |
| I-b-187 | b | OH | 3-(4-Cl—Ph)-1-cyclopropylyl-1H-1,2,4-triazol-5-yl | |
| I-b-188 | c | OH | 3-(4-Cl—Ph)-1-cyclopropylyl-1H-1,2,4-triazol-5-yl | |
| I-b-189 | a | OH | 3-(2-F—Ph)-1-methyl-1H-1,2,4-triazol-5-yl | |
| I-b-190 | b | OH | 3-(2-F—Ph)-1-methyl-1H-1,2,4-triazol-5-yl | |
| I-b-191 | c | OH | 3-(2-F—Ph)-1-methyl-1H-1,2,4-triazol-5-yl | |
| I-b-192 | a | OH | 3-(2-F—Ph)-1-ethyl-1H-1,2,4-triazol-5-yl | |
| I-b-193 | b | OH | 3-(2-F—Ph)-1-ethyl-1H-1,2,4-triazol-5-yl | |
| I-b-194 | c | OH | 3-(2-F—Ph)-1-ethyl-1H-1,2,4-triazol-5-yl | |
| I-b-195 | a | OH | 3-(2-F—Ph)-1-cyclopropyl-1H-1,2,4-triazol-5-yl | |
| I-b-196 | b | OH | 3-(2-F—Ph)-1-cyclopropyl-1H-1,2,4-triazol-5-yl | |
| I-b-197 | c | OH | 3-(2-F—Ph)-1-cyclopropyl-1H-1,2,4-triazol-5-yl | |
| I-b-198 | a | OH | 3-(4-F—Ph)-1-methyl1H-1,2,4-triazol-5-yl | |
| I-b-199 | b | OH | 3-(4-F—Ph)-1-methyl-1H-1,2,4-triazol-5-yl | |

TABLE 72-continued

Compounds according to the invention in which R¹ represents hydrogen. R² represents methyl (a), 2,2-difluoroethyl (b) or propargyl (c). Ph represents phenyl. Py represents pyridine.

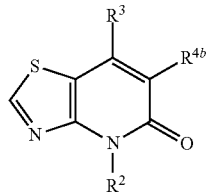

| No. | R² | R³ | R⁴ᵇ | ¹H NMR |
|---|---|---|---|---|
| I-b-200 | c | OH | 3-(4-F—Ph)-1-methyl-1H-1,2,4-triazol-5-yl | |
| I-b-201 | a | OH | 3-(4-F—Ph)-1-ethyl-1H-1,2,4-triazol-5-yl | 400 MHz, DMSO-d₆: 9.47 (s, 1H); 8.06 (m, 2H); 7.31 (m, 2H); 4.02 (q, 2H); 3.71 (s, 3H); 1.37 (t, 3H) |
| I-b-202 | b | OH | 3-(4-F—Ph)-1-ethyl-1H-1,2,4-triazol-5-yl | |
| I-b-203 | c | OH | 3-(4-F—Ph)-1-ethyl-1H-1,2,4-triazol-5-yl | 400 MHz, DMSO-d₆: 9.49 (s, 1H); 8.07 (m, 2H); 7.32 (m, 2H); 5.04 (d, 2H); 4.03 (q, 2H); 3.18 (t, 1H); 1.37 (t, 3H) |
| I-b-204 | a | OH | 3-(4-F—Ph)-1-cyclopropyl-1H-1,2,4-triazol-5-yl | |
| I-b-205 | b | OH | 3-(4-F—Ph)-1-cyclopropyl-1H-1,2,4-triazol-5-yl | |
| I-b-206 | c | OH | 3-(4-F—Ph)-1-cyclopropyl-1H-1,2,4-triazol-5-yl | |
| I-b-207 | a | OH | 3-(2,4-F₂—Ph)-1-methyl-1H-1,2,4-triazol-5-yl | |
| I-b-208 | b | OH | 3-(2,4-F₂—Ph)-1-methyl-1H-1,2,4-triazol-5-yl | |
| I-b-209 | c | OH | 3-(2,4-F₂—Ph)-1-methyl-1H-1,2,4-triazol-5-yl | |
| I-b-210 | a | OH | 3-(2,4-F₂—Ph)-1-ethyl-1H-1,2,4-triazol-5-yl | 400 MHz, DMSO-d₆: 9.48 (s, 1H); 8.08 (dt, 1H); 7.39 (m, 1H); 7.21 (m, 1H); 4.04 (q, 2H); 3.71 (s, 3H); 1.36 (t, 3H) |
| I-b-211 | b | OH | 3-(2,4-F₂—Ph)-1-ethyl-1H-1,2,4-triazol-5-yl | 400 MHz, DMSO-d₆: 9.49 (s, 1H); 8.07 (dt, 1H); 7.40 (ddd, 1H); 7.22 (td, 1H); 6.38 (tt, 1H); 4.74 (td, 2H); 4.06 (q, 2H); 1.37 (t, 3H) |
| I-b-212 | c | OH | 3-(2,4-F₂—Ph)-1-ethyl-1H-1,2,4-triazol-5-yl | |
| I-b-213 | a | OH | 3-(2,4-F₂—Ph)-1-cyclopropyl-1H-1,2,4-triazol-5-yl | |
| I-b-214 | b | OH | 3-(2,4-F₂—Ph)-1-cyclopropyl-1H-1,2,4-triazol-5-yl | |
| I-b-215 | c | OH | 3-(2,4-F₂—Ph)-1-cyclopropyl-1H-1,2,4-triazol-5-yl | |
| I-b-216 | a | OH | 3-(2-CF₃—Ph)-1-methyl-1H-1,2,4-triazol-5-yl | |
| I-b-217 | b | OH | 3-(2-CF₃—Ph)-1-methyl-1H-1,2,4-triazol-5-yl | |
| I-b-218 | c | OH | 3-(2-CF₃—Ph)-1-methyl-1H-1,2,4-triazol-5-yl | |
| I-b-219 | a | OH | 3-(2-CF₃—Ph)-1-ethyl-1H-1,2,4-triazol-5-yl | |
| I-b-220 | b | OH | 3-(2-CF₃—Ph)-1-ethyl-1H-1,2,4-triazol-5-yl | |
| I-b-221 | c | OH | 3-(2-CF₃—Ph)-1-ethyl-1H-1,2,4-triazol-5-yl | |
| I-b-222 | a | OH | 3-(2-CF₃—Ph)-1-cyclopropyl-1H-1,2,4-triazol-5-yl | |
| I-b-223 | b | OH | 3-(2-CF₃—Ph)-1-cyclopropyl-1H-1,2,4-triazol-5-yl | |
| I-b-224 | c | OH | 3-(2-CF₃—Ph)-1-cyclopropyl-1H-1,2,4-triazol-5-yl | |
| I-b-225 | a | OH | 3-(2,4-Cl₂—Ph)-1-methyl-1H-1,2,4-triazol-5-yl | |
| I-b-226 | b | OH | 3-(2,4-Cl₂—Ph)-1-methyl-1H-1,2,4-triazol-5-yl | |
| I-b-227 | c | OH | 3-(2,4-Cl₂—Ph)-1-methyl-1H-1,2,4-triazol-5-yl | |
| I-b-228 | a | OH | 3-(2,4-Cl₂—Ph)-1-ethyl-1H-1,2,4-triazol-5-yl | 400 MHz, DMSO-d₆: 9.48 (s, 1H); 8.02 (d, 1H); 7.75 (d, 1H); 7.55 (dd, 1H); 4.06 (q, 2H); 3.71 (s, 3H); 1.38 (t, 3H) |

TABLE 72-continued

Compounds according to the invention in which R¹ represents hydrogen. R² represents methyl (a), 2,2-difluoroethyl (b) or propargyl (c). Ph represents phenyl. Py represents pyridine.

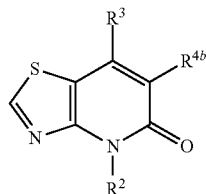

| No. | R² | R³ | R⁴ᵇ | ¹H NMR |
|---|---|---|---|---|
| I-b-229 | b | OH | 3-(2,4-Cl₂—Ph)-1-ethyl-1H-1,2,4-triazol-5-yl | |
| I-b-230 | c | OH | 3-(2,4-Cl₂—Ph)-1-ethyl-1H-1,2,4-triazol-5-yl | 400 MHz, DMSO-d₆: 9.51 (s, 1H); 8.02 (d, 1H); 7.76 (d, 1H); 7.55 (dd, 1H); 5.05 (d, 2H); 4.06 (q, 2H); 3.19 (t, 1H); 1.38 (t, 3H) |
| I-b-231 | a | OH | 3-(2,4-Cl₂—Ph)-1-cyclopropyl-1H-1,2,4-triazol-5-yl | |
| I-b-232 | b | OH | 3-(2,4-Cl₂—Ph)-1-cyclopropyl-1H-1,2,4-triazol-5-yl | |
| I-b-233 | c | OH | 3-(2,4-Cl₂—Ph)-1-cyclopropyl-1H-1,2,4-triazol-5-yl | |
| I-b-234 | a | OH | 3-(4-Cl-2-CF₃—Ph)-1-methyl-1H-1,2,4-triazol-5-yl | |
| I-b-235 | b | OH | 3-(4-Cl-2-CF₃—Ph)-1-methyl-1H-1,2,4-triazol-5-yl | |
| I-b-236 | c | OH | 3-(4-Cl-2-CF₃—Ph)-1-methyl-1H-1,2,4-triazol-5-yl | |
| I-b-237 | a | OH | 3-(4-Cl-2-CF₃—Ph)-1-ethyl-1H-1,2,4-triazol-5-yl | |
| I-b-238 | b | OH | 3-(4-Cl-2-CF₃—Ph)-1-ethyl-1H-1,2,4-triazol-5-yl | |
| I-b-239 | c | OH | 3-(4-Cl-2-CF₃—Ph)-1-ethyl-1H-1,2,4-triazol-5-yl | |
| I-b-240 | a | OH | 3-(4-Cl-2-CF₃—Ph)-1-cyclopropyl-1H-1,2,4-triazol-5-yl | |
| I-b-241 | b | OH | 3-(4-Cl-2-CF₃—Ph)-1-cyclopropyl-1H-1,2,4-triazol-5-yl | |
| I-b-242 | c | OH | 3-(4-Cl-2-CF₃—Ph)-1-cyclopropyl-1H-1,2,4-triazol-5-yl | |
| I-b-243 | a | OH | 3-(2-Cl-4-Me—Ph)-1-methyl-1H-1,2,4-triazol-5-yl | |
| I-b-244 | b | OH | 3-(2-Cl-4-Me—Ph)-1-methyl-1H-1,2,4-triazol-5-yl | |
| I-b-245 | c | OH | 3-(2-Cl-4-Me—Ph)-1-methyl-1H-1,2,4-triazol-5-yl | |
| I-b-246 | a | OH | 3-(2-Cl-4-Me—Ph)-1-ethyl-1H-1,2,4-triazol-5-yl | |
| I-b-247 | b | OH | 3-(2-Cl-4-Me—Ph)-1-ethyl-1H-1,2,4-triazol-5-yl | |
| I-b-248 | c | OH | 3-(2-Cl-4-Me—Ph)-1-ethyl-1H-1,2,4-triazol-5-yl | |
| I-b-249 | a | OH | 3-(2-Cl-4-Me—Ph)-1-cyclopropyl-1H-1,2,4-triazol-5-yl | |
| I-b-250 | b | OH | 3-(2-Cl-4-Me—Ph)-1-cyclopropyl-1H-1,2,4-triazol-5-yl | |
| I-b-251 | c | OH | 3-(2-Cl-4-Me—Ph)-1-cyclopropyl-1H-1,2,4-triazol-5-yl | |
| I-b-252 | c | OC(O)OEt | 3-Ph-5-methyl-1H-pyrazol-1-yl | 400 MHz, DMSO-d₆: 9.66 (s, 1H); 7.75 (m, 2H); 7.42 (m, 2H); 7.32 (m, 1H); 6.72 (d, 1H); 5.18 (m, 2H); 4.12 (m, 2H); 3.30 (m, 1H); 2.19 (d, 3H); 1.01 (t, 3H) |
| I-b-253 | b | OC(O)SMe | 3-(4-Cl—Ph)-5-propyl-1H-pyrazol-1-yl | 400 MHz, DMSO-d₆: 9.64 (s, 1H); 7.81 (m, 2H); 7.47 (m, 2H); 6.79 (br s, 1H); 6.46 (tt, 1H); 4.87 (td, 2H); 2.52 (m, 1H); 2.37 (m, 1H); 2.31 (s, 3H); 1.63 (m, 2H); 0.90 (t, 3H) |

TABLE 72-continued

Compounds according to the invention in which R¹ represents hydrogen. R² represents methyl (a), 2,2-difluoroethyl (b) or propargyl (c). Ph represents phenyl. Py represents pyridine.

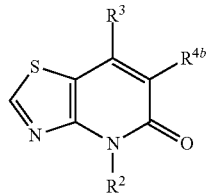

| No. | R² | R³ | R⁴ᵇ | ¹H NMR |
|---|---|---|---|---|
| I-b-254 | b | OC(O)SMe | 3-Ph-5-methyl-1H-pyrazol-1-yl | 400 MHz, DMSO-$d_6$: 9.64 (s, 1H); 7.77 (m, 2H); 7.42 (m, 2H); 7.32 (m, 1H); 6.71 (d, 1H); 6.47 (tt, 1H); 4.88 (td, 2H); 2.31 (s, 3H); 2.18 (d, 3H) |
| I-b-255 | a | OC(O)SMe | 3-Ph-5-methyl-1H-pyrazol-1-yl | 400 MHz, DMSO-$d_6$: 9.62 (s, 1H); 7.76 (m, 2H); 7.41 (m, 2H); 7.31 (m, 1H); 6.70 (d, 1H); 3.85 (s, 3H); 2.30 (s, 3H); 2.17 (d, 3H) |
| I-b-256 | b | OC(O)SMe | 3-(3-CF₃—Ph)-5-methyl-1H-pyrazol-1-yl | 400 MHz, DMSO-$d_6$: 9.65 (s, 1H); 8.08 (m, 2H); 7.68 (m, 2H); 6.89 (d, 1H); 6.47 (tt, 1H); 4.88 (td, 2H); 2.30 (s, 3H); 2.20 (d, 3H) |
| I-b-257 | c | OC(O)SMe | 3-(3-Br—Ph)-5-methyl-1H-pyrazol-1-yl | 400 MHz, DMSO-$d_6$: 9.67 (s, 1H); 7.74 (m, 2H); 7.62 (m, 2H); 6.75 (s, 1H); 5.18 (t, 2H); 3.31 (t, 1H); 2.31 (s, 3H); 2.17 (d, 3H) |
| I-b-258 | b | OC(O)SMe | 3-(3-Cl—Ph)-5-methyl-1H-pyrazol-1-yl | 400 MHz, DMSO-$d_6$: 9.65 (s, 1H); 7.81 (t, 1H); 7.74 (dt, 1H); 7.46 (t, 1H); 7.39 (m, 1H); 6.80 (d, 1H); 6.47 (tt, 1H); 4.88 (td, 2H); 2.32 (s, 3H); 2.18 (br s, 3H) |
| I-b-259 | b | OC(O)SMe | 3-(4-Br—Ph)-5-methyl-1H-pyrazol-1-yl | 400 MHz, DMSO-$d_6$: 9.64 (s, 1H); 7.72 (m, 2H); 7.61 (m, 2H); 6.75 (d, 1H); 6.50 (tt, 1H); 4.88 (td, 2H); 2.31 (s, 3H); 2.18 (d, 3H) |
| I-b-260 | c | OC(O)SMe | 3-Ph-5-methyl-1H-pyrazol-1-yl | 400 MHz, DMSO-$d_6$: 9.67 (s, 1H); 7.78 (m, 2H); 7.42 (m, 2H); 7.32 (m, 1H); 6.72 (d, 1H); 5.18 (m, 2H); 3.31 (t, 1H); 2.31 (s, 3H); 2.17 (d, 3H) |
| I-b-261 | a | OC(O)SMe | 3-(4-Br—Ph)-5-methyl-1H-pyrazol-1-yl | 400 MHz, DMSO-$d_6$: 9.62 (s, 1H); 7.72 (m, 2H); 7.60 (m, 2H); 6.73 (d, 1H); 3.85 (s, 3H); 2.31 (s, 3H); 2.17 (s, 3H) |
| I-b-262 | a | OC(O)SMe | 3-(3-Cl—Ph)-5-methyl-1H-pyrazol-1-yl | 400 MHz, DMSO-$d_6$: 9.63 (s, 1H); 7.80 (t, 1H); 7.74 (dt, 1H); 7.45 (t, 1H); 7.37 (m, 1H); 6.79 (d, 1H); 3.85 (s, 3H); 2.32 (s, 3H); 2.18 (d, 3H) |
| I-b-263 | b | OC(O)SMe | 3-(4-CF₃—Ph)-5-methyl-1H-pyrazol-1-yl | 400 MHz, DMSO-$d_6$: 9.65 (s, 1H); 8.00 (m, 2H); 7.80 (m, 2H); 6.85 (d, 1H); 6.47 (tt, 1H); 4.88 (td, 2H); 2.31 (s, 3H); 2.20 (d, 3H) |

TABLE 72-continued

Compounds according to the invention inwhich R¹ represents hydrogen. R² represents methyl (a), 2,2-difluoroethyl (b) or propargyl (c). Ph represents phenyl. Py represents pyridine.

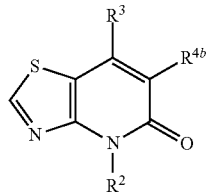

| No. | R² | R³ | R⁴ᵇ | ¹H NMR |
|---|---|---|---|---|
| I-b-264 | b | OC(O)OEt | 3-(3,4-Cl₂—Ph)-5-methyl-1H-pyrazol-1-yl | 400 MHz, DMSO-d₆: 9.65 (s, 1H); 7.97 (d, 1H); 7.76 (dd, 1H); 7.69 (d, 1H); 6.85 (d, 1H); 6.47 (tt, 1H); 4.88 (td, 1H); 4.14 (m, 2H); 2.19 (d, 3H); 1.03 (t, 3H) |
| I-b-265 | b | OC(O)OEt | 3-(4-CF₃—Ph)-5-methyl-1H-pyrazol-1-yl | 400 MHz, DMSO-d₆: 9.65 (s, 1H); 7.98 (d, 2H); 7.78 (d, 2H); 6.86 (d, 1H); 6.48 (tt, 1H); 4.88 (td, 2H); 4.12 (m, 2H); 2.21 (d, 3H); 0.99 (t, 3H) |
| I-b-266 | b | OC(O)SMe | 3-(3,4-Cl₂—Ph)-5-methyl-1H-pyrazol-1-yl | 400 MHz, DMSO-d₆: 9.65 (s, 1H); 7.99 (d, 1H); 7.77 (dd, 1H); 7.69 (d, 1H); 6.84 (d, 1H); 6.47 (tt, 1H); 4.88 (td, 2H); 2.32 (s, 3H); 2.19 (d, 3H) |
| I-b-267 | c | OC(O)SMe | 3-(3-Cl—Ph)-1-ethyl-1H-1,2,4-triazol-5-yl | 400 Hz, CDCl₃: 9.09 (s, 1H); 8.14 (m, 1H); 8.01 (m, 1H); 7.35 (m, 2H); 5.29 (d, 2H); 4.17 (q, 2H); 2.28 (s, 3H); 2.26 (t, 1H); 1.57 (t, 3H) |
| I-b-268 | c | OC(O)OEt | 3-(3-Cl—Ph)-1-ethyl-1H-1,2,4-triazol-5-yl | 400 MHz, CDCl₃: 9.10 (s, 1H); 8.12 (m, 1H); 8.00 (m, 1H); 7.35 (m, 2H); 5.29 (d, 2H); 4.19 (q, 2H); 4.15 (q, 2H); 2.27 (t, 1H); 1.58 (t, 3H); 1.16 (t, 3H) |
| I-b-269 | b | OC(O)OEt | 3-(3-Cl—Ph)-1-ethyl-1H-1,2,4-triazol-5-yl | 400 MHz, CDCl₃: 9.06 (s, 1H); 8.11 (m, 1H); 8.00 (m, 1H); 7.35 (m, 2H); 6.28 (tt, 1H); 4.93 (td, 2H); 4.16 (m, 4H); 1.57 (t, 3H); 1.16 (t, 3H) |
| I-b-270 | b | OCH₂CHF₂ | 3-(2,4-F₂—Ph)-1-ethyl-1H-1,2,4-triazol-5-yl | 400 MHz, CDCl₃: 9.04 (s, 1H); 8.06 (m, 1H); 6.96 (m, 2H); 6.25 (tt, 1H); 5.95 (tt, 1H); 4.86 (td, 2H); 4.17 (q, 2H); 4.12 (m, 2H); 1.56 (t, 3H) |
| I-b-271 | c | OC(O)OEt | 3-(2,4-F₂—Ph)-1-ethyl-1H-1,2,4-triazol-5-yl | 400 MHZ, CDCl₃: 9.09 (s, 1H); 8.04 (m, 1H); 6.93 (m, 2H); 5.29 (d, 2H); 4.22 (q, 2H); 4.16 (q, 2H); 2.27 (t, 1H); 1.58 (t, 3H); 1.17 (t, 3H) |
| I-b-272 | a | OC(O)OEt | 3-(2,4-F₂—Ph)-1-ethyl-1H-1,2,4-triazol-5-yl | 400 MHz, CDCl₃: 9.04 (s, 1H); 8.05 (m, 1H); 6.94 (m, 2H); 4.21 (q, 2H); 4.16 (q, 2H); 3.96 (s, 3H); 1.57 (t, 3H); 1.18 (t, 3H) |
| I-b-273 | a | OC(O)SMe | 3-(2,4-F₂—Ph)-1-ethyl-1H-1,2,4-triazol-5-yl | 400 Hz, CDCl₃: 9.04 (s, 1H); 8.07 (m, 1H); 6.93 (m, 2H); 4.19 (q, 2H); 3.96 (s, 3H); 2.29 (s, 3H); 1.56 (t, 3H) |

TABLE 72-continued

Compounds according to the invention in which R¹ represents hydrogen. R² represents methyl (a), 2,2-difluoroethyl (b) or propargyl (c). Ph represents phenyl. Py represents pyridine.

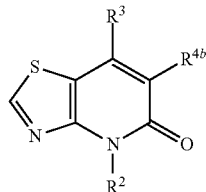

| No. | R² | R³ | R⁴ᵇ | ¹H NMR |
|---|---|---|---|---|
| I-b-274 | b | OC(O)OEt | 3-(2,4-F₂—Ph)-1-ethyl-1H-1,2,4-triazol-5-yl | 400 MHz, CDCl₃: 9.06 (s, 1H); 8.04 (m, 1H); 6.94 (m, 2H); 6.28 (tt, 1H); 4.93 (td, 2H); 4.18 (m, 4H); 1.57 (t, 3H); 1.17 (t, 3H) |
| I-b-275 | a | OH | 3-(2,4-Cl₂—Ph)-1-(2,2-difluoroethyl)-1H-1,2,4-triazol-5-yl | 400 MHz, DMSO-d₆: 9.10 (s, 1H); 7.96 (d, 1H); 7.71 (d, 1H); 7.53 (dd, 1H); 6.42 (tt, 1H); 4.43 (td, 2H); 3.54 (s, 3H) |
| I-b-276 | Et | OH | 3-(2,4-Cl₂—Ph)-1-ethyl-1H-1,2,4-triazol-5-yl | 400 MHz, CDCl₃: 9.00 (s, 1H); 7.91 (d, 1H); 7.54 (d, 1H); 7.35 (dd, 1H); 4.67 (q, 2H); 4.56 (q, 2H); 1.55 (t, 3H); 1.41 (t, 3H) |
| I-b-277 | Et | OH | 3-(4-Cl—Ph)-1-ethyl-1H-1,2,4-triazol-5-yl | 400 MHz, DMSO-d₆: 12.06 (br s, 1H); 9.49 (s, 1H); 7.81 (m, 2H); 7.45 (m, 2H); 6.69 (br s, 1H); 4.35 (q, 2H); 2.08 (s, 3H); 1.26 (t, 3H) |
| I-b-278 | a | OC(O)SMe | 3-(2,4-Cl₂—Ph)-1-(2,2-difluoroethyl)-1H-1,2,4-triazol-5-yl | 400 MHz, DMSO-d₆: 9.66 (s, 1H); 7.93 (d, 1H); 7.78 (d, 1H); 7.60 (dd, 1H); 6.41 (tt, 1H); 4.71 (td, 2H); 3.84 (s, 3H); 2.39 (s, 3H) |
| I-b-279 | a | OC(O)SMe | 3-(2,4-Cl₂—Ph)-1-ethyl-1H-1,2,4-triazol-5-yl | 400 MHz, CDCl₃: 9.04 (s, 1H); 7.88 (d, 1H); 7.50 (d, 1H); 7.30 (dd, 1H); 4.19 (q, 2H); 3.96 (s, 3H); 2.29 (s, 3H); 1.58 (t, 3H) |

B. FORMULATION EXAMPLES a) A dusting product is obtained by mixing 10 parts by weight of a compound of the formula (I) and/or salts thereof and 90 parts by weight of talc as inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
75 parts by weight of a compound of the formula (I) and/or salts thereof,
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill, and granulating the powder in a fluidized bed by spray application of water as a granulating liquid.

f) Water-dispersible granules are also obtained by homogenizing and precomminuting
25 parts by weight of a compound of the formula (I) and/or salts thereof,
5 parts by weight of sodium 2,2'-dinaphthylmethane-6,6'-disulfonate,
2 parts by weight of sodium oleoylmethyltaurate,
1 part by weight of polyvinyl alcohol, 17 parts by weight of calcium carbonate and 50 parts by weight of water in a colloid mill, then grinding the mixture in a bead mill and atomizing and drying the resulting suspension in a spray tower by means of a one-phase nozzle.

C. BIOLOGICAL EXAMPLES

1. Pre-Emergence Herbicidal Action Against Weed Plants

Seeds of monocotyledonous and dicotyledonous weed plants and crop plants are placed in wood-fiber pots in sandy loam and covered with soil. The compounds according to the invention, formulated in the form of wettable powders (WP) or as emulsion concentrates (EC), are then applied as aqueous suspension or emulsion at a water application rate of 600 to 800 l/ha (converted) with the addition of 0.2% of wetting agent to the surface of the covering soil. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). Here, the compound No. I-a-19, for example, shows, at an application rate of 1280 g/ha, an activity of at least 80% against *Alopecurus myosuroides* and *Cyperus serotinus* and at the same time no damage in rice and wheat. The compound No. I-a-32 shows, at an application rate of 1280 g/ha, an activity of at least 80% against *Polygonum convolvulus* and at the same time no damage in corn and oilseed rape. The compounds Nos. I-a-38 and I-a-39 each show, at an application rate of 1280 g/ha, an of at least 80% against *Echinochloa crus galli* and *Veronica persica* and at the same time no damage in corn and oilseed rape. The compound No. I-a-42 shows, at an application rate of 1280 g/ha, an activity of at least 80% against *Lolium multiflorum* and *Setaria viridis* and at the same time no damage in wheat.

2. Post-Emergence Herbicidal Action Against Weed Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed as aqueous suspension or emulsion at a water application rate of 600 to 800 l/ha (converted) with the addition of 0.2% of wetting agent onto the green parts of the plants. After the test plants have been left to stand in the greenhouse under optimal growth conditions for about 3 weeks, the action of the formulations is assessed visually in comparison to untreated controls (herbicidal action in percent (%): 100% activity=the plants have died, 0% activity=like control plants). Here, the compounds Nos. I-a-39 and I-a-42, for example, show, at an application rate of 320 g/ha, an activity of at least 80% against *Setaria viridis* and at the same time no damage in corn and oilseed rape. The compound No. I-a-38 shows, at an application rate of 320 g/ha, an activity of at least 80% against *Echinochloa crus galli* and *Lolium multiflorum* and at the same time no damage in corn and rice. The compound No. I-a-42 shows, at an application rate of 80 g/ha, an activity of at least 80% against *Echinochloa crus galli* and *Setaria viridis* and at the same time no damage in wheat, corn and rice.

3. Insecticidal Action

Example A

Phaedon Test (PHAECO Spray Treatment)

Solvent: 78.0 parts by weight of acetone
 1.5 parts by weight of dimethylformamide
Emulsifier: 0.5 part by weight of alkylaryl polyglycol ether
To produce a suitable preparation of active compound, 1 part by weight of active compound is mixed with the stated amounts of solvent and emulsifier, and the concentrate is diluted with emulsifier-containing water to the desired concentration. Discs of Chinese cabbage leaves (*Brassica pekinensis*) are sprayed with an active compound formulation of the desired concentration and, after drying, populated with larvae of the mustard beetle (*Phaedon cochleariae*). After 7 days, the activity in % is determined. 100% means that all of the beetle larvae have been killed; 0% means that none of the beetle larvae have been killed. In this test, for example, the following compounds of the Preparation Examples show, at an application rate of 500 g/ha, an activity of 100%: I-a-29, I-a-40.

Example B

*Spodoptera frugiperda* Test (SPODFR Spray Treatment)

Solvent: 78.0 parts by weight of acetone
 1.5 parts by weight of dimethylformamide
Emulsifier: 0.5 parts by weight of alkylaryl polyglycol ether
To produce a suitable preparation of active compound, 1 part by weight of active compound is mixed with the stated amounts of solvent and emulsifier, and the concentrate is diluted with emulsifier-containing water to the desired concentration. Disks of corn leaves (*Zea mays*) are sprayed with an active compound preparation of the desired concentration and, after drying, populated with caterpillars of the armyworm (*Spodoptera frugiperda*). After 7 days, the activity in % is determined. 100% means that all of the caterpillars have been killed; 0% means that none of the caterpillars have been killed. In this test, for example, the following compounds of the Preparation Examples show, at an application rate of 500 g/ha, an activity of 85%: I-a-38, I-a-39, I-a-40. In this test, for example, the following compounds of the Preparation Examples show, at an application rate of 500 g/ha, an activity of 100%: I-a-38, I-a-39.

Example C

*Tetranychus* Test, OP-Resistant (TETRUR Spray Treatment)

Solvent: 78.0 parts by weight of acetone
 1.5 parts by weight of dimethylformamide
Emulsifier: 0.5 parts by weight of alkylaryl polyglycol ether
To produce a suitable preparation of active compound, 1 part by weight of active compound is mixed with the stated amounts of solvent and emulsifier, and the concentrate is diluted with emulsifier-containing water to the desired concentration. Discs of bean leaves (*Phaseolus vulgaris*) infested by all stages of the greenhouse red spider mite (*Tetranychus urticae*) are sprayed with an active compound formulation of the desired concentration. After 6 days, the activity in % is determined. 100% means that all of the spider mites have been killed; 0% means that none of the spider mites have been killed.

In this test, for example, the following compounds of the Preparation Examples show, at an application rate of 500 g/ha, an activity of 85%: I-a-8, I-a-37, I-a-38, I-a-39.

In this test, for example, the following compounds of the Preparation Examples show, at an application rate of 500 g/ha, an activity of 90%: I-a-8, I-a-37, I-a-39.

In this test, for example, the following compounds of the Preparation Examples show, at an application rate of 500 g/ha, an activity of 100%: I-a-8.

We claim:

1. A thiazolopyridinone of formula (I) and/or a salt thereof

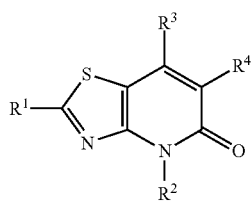

(I)

in which $R^1$ represents hydrogen, halogen, nitro, cyano,
($C_1$-$C_6$)-alkyl, ($C_2$-$C_6$)-alkenyl, ($C_2$-$C_6$)-alkynyl, ($C_1$-$C_6$)-alkoxy, ($C_1$-$C_6$)-alkylthio, ($C_1$-$C_6$)-alkylsulfinyl, ($C_1$-$C_6$)-alkylsulfonyl, ($C_3$-$C_6$)-cycloalkyl, ($C_1$-$C_6$)-alkoxy-($C_1$-$C_6$)-alkyl, di-($C_1$-$C_6$)-alkoxy-($C_1$-$C_6$)-alkyl or ($C_1$-$C_6$)-alkylthio-($C_1$-$C_6$)-alkyl, each of which is substituted by n halogen atoms, $R^2$ represents hydrogen,
($C_1$-$C_6$)-alkyl, ($C_2$-$C_6$)-alkenyl, ($C_3$-$C_6$)-alkynyl, ($C_3$-$C_6$)-cycloalkyl, ($C_1$-$C_6$)-alkoxy-($C_1$-$C_6$)-alkyl or di-($C_1$-$C_6$)-alkoxy-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_3$-$C_6$)-cycloalkyl-($C_1$-$C_6$)-alkyl, cyano-($C_1$-$C_6$)-alkyl, each of which is substituted by n halogen atoms, or phenyl or benzyl, each of which is substituted by n radicals from the group consisting of halogen, ($C_1$-$C_6$)-alkyl and ($C_1$-$C_6$)-alkoxy, $R^3$ represents hydroxy, O—C(=O)$R^7$, O—C(=L)M$R^8$, O—SO$_2R^9$, O—P(=L)$R^{10}R^{11}$, O—C(=L)N$R^{12}R^{13}$, O-E or O—$R^{14}$, $R^4$ represents $R^{4a}$ or $R^{4b}$, $R^{4a}$ represents aryl which is substituted by n radicals $R^5$ and one radical $R^6$, $R^{4b}$ represents 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-1-yl, 1,2,4-triazol-3-yl, 1,2,4-triazol-4-yl, 1,2,4-triazol-5-yl, 1,2,3-triazol-1-yl, 1,2,3-triazol-2-yl, 1,2,3-triazol-4-yl, tetrazol-1-yl, tetrazol-2-yl, tetrazol-5-yl, indol-1-yl, indol-2-yl, indol-3-yl, isoindol-1-yl, isoindol-2-yl, benzofur-2-yl, benzothiophen-2-yl, benzofur-3-yl, benzothiophen-3-yl, benzoxazol-2-yl, benzothiazol-2-yl, benzimidazol-2-yl, indazol-1-yl, indazol-2-yl, indazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl or 1,2,4-triazin-6-yl, substituted by n radicals $R^5$ and by m radicals $R^6$, $R^5$ represents hydrogen, halogen, nitro, cyano,
($C_1$-$C_6$)-alkyl, ($C_2$-$C_6$)-alkenyl, ($C_2$-$C_6$)-alkynyl, ($C_1$-$C_6$)-alkoxy, ($C_1$-$C_6$)-alkylthio, ($C_1$-$C_6$)-alkylsulfinyl, ($C_1$-$C_6$)-alkylsulfonyl, ($C_3$-$C_6$)-cycloalkyl, ($C_1$-$C_6$)-alkoxy-($C_1$-$C_6$)-alkyl or ($C_1$-$C_6$)-alkylthio-($C_1$-$C_6$)-alkyl, each of which is substituted by n halogen atoms, $R^6$ represents aryl or heteroaryl, each of which is substituted by s radicals $R^5$, E represents a metal ion equivalent or an ammonium ion, L represents oxygen or sulfur, M represents oxygen or sulfur, $R^7$ represents ($C_1$-$C_6$)-alkyl, ($C_2$-$C_6$)-alkenyl, ($C_1$-$C_6$)-alkoxy-($C_1$-$C_6$)-alkyl, di-($C_1$-$C_6$)-alkoxy-($C_1$-$C_6$)-alkyl or ($C_1$-$C_6$)-alkylthio-($C_1$-$C_6$)-alkyl, each of which is substituted by n halogen atoms, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, ($C_1$-$C_6$)-alkyl and ($C_1$-$C_6$)-alkoxy, or ($C_3$-$C_6$)-cycloalkyl, phenyl, phenyl-($C_1$-$C_6$)-alkyl, phenoxy-($C_1$-$C_6$)-alkyl or heteroaryloxy-($C_1$-$C_6$)-alkyl, each of which is substituted by n radicals from the group consisting of halogen, ($C_1$-$C_6$)-alkyl and ($C_1$-$C_6$)-alkoxy, $R^8$ represents ($C_1$-$C_6$)-alkyl, ($C_2$-$C_6$)-alkenyl, ($C_1$-$C_6$)-alkoxy-($C_1$-$C_6$)-alkyl or di-($C_1$-$C_6$)-alkoxy-($C_1$-$C_6$)-alkyl, each of which is substituted by n halogen atoms, or ($C_3$-$C_6$)-cycloalkyl, phenyl or benzyl, each of which is substituted by n radicals from the group consisting of halogen, ($C_1$-$C_6$)-alkyl and ($C_1$-$C_6$)-alkoxy, $R^9$, $R^{10}$, $R^{11}$ independently of one another represent ($C_1$-$C_6$)-alkyl, ($C_1$-$C_6$)-alkoxy, N—($C_1$-$C_6$)-alkylamino, N,N-di-($C_1$-$C_6$)-alkylamino, ($C_1$-$C_6$)-alkylthio, ($C_2$-$C_6$)-alkenyl or ($C_3$-$C_6$)-cycloalkylthio, each of which is substituted by n halogen atoms, or phenyl, benzyl, phenoxy or phenylthio, each of which is substituted by n radicals from the group consisting of halogen, ($C_1$-$C_6$)-alkyl and ($C_1$-$C_6$)-alkoxy, $R^{12}$, $R^{13}$ independently of one another each represent hydrogen,
($C_1$-$C_6$)-alkyl, ($C_3$-$C_6$)-cycloalkyl, ($C_2$-$C_6$)-alkenyl, ($C_1$-$C_6$)-alkoxy or ($C_1$-$C_6$)-alkoxy-($C_1$-$C_6$)-alkyl, substituted by n halogen atoms, phenyl or benzyl, each of which is substituted by n radicals from the group consisting of halogen, ($C_1$-$C_6$)-alkyl and ($C_1$-$C_6$)-alkoxy, or $R^{12}$ and $R^{13}$ together with the nitrogen atom to which they are attached form a 3- to 6-membered ring containing 2 to 5 carbon atoms and in each case 0 or 1 oxygen or sulfur atoms, $R^{14}$ represents ($C_1$-$C_6$)-alkyl, ($C_2$-$C_6$)-alkenyl, ($C_2$-$C_6$)-alkynyl, ($C_1$-$C_6$)-alkoxy-($C_1$-$C_6$)-alkyl, ($C_1$-$C_6$)-alkylthio-($C_1$-$C_6$)-alkyl or di-($C_1$-$C_6$)-alkoxy-($C_1$-$C_6$)-alkyl, each of which is substituted by n halogen atoms, ($C_3$-$C_6$)-cycloalkyl substituted by n radicals from the group consisting of halogen, ($C_1$-$C_6$)-alkyl and ($C_1$-$C_6$)-alkoxy, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, $(C_1-C_6)$-alkyl and $(C_1-C_6)$-alkoxy, phenyl, phenyl-$(C_1-C_6)$-alkyl, heteroaryl, phenoxy-$(C_1-C_6)$-alkyl or heteroaryloxy-$(C_1-C_6)$-alkyl, substituted by n radicals from the group consisting of halogen, $(C_1-C_6)$-alkyl and $(C_1-C_6)$-alkoxy, m represents 0 or 1, n represents 0, 1, 2 or 3, s represents 0, 1, 2, 3 or 4.

2. The thiazolopyridinone as claimed in claim 1 in which $R^1$ represents hydrogen, $(C_1-C_6)$-alkyl, $(C_1-C_6)$-alkoxy, $(C_1-C_6)$-alkylthio, $(C_1-C_6)$-alkylsulfonyl, $(C_3-C_6)$-cycloalkyl, $(C_1-C_6)$-alkoxy-$(C_1-C_6)$-alkyl or $(C_1-C_6)$-alkylthio-$(C_1-C_6)$-alkyl, each of which is substituted by n halogen atoms, $R^2$ represents hydrogen, $(C_1-C_6)$-alkyl, $(C_2-C_6)$-alkenyl, $(C_3$-CO-alkynyl, $(C_1-C_6)$-alkoxy-$(C_1-C_6)$-alkyl, $(C_1-C_6)$-alkylthio-$(C_1-C_6)$-alkyl, $(C_3-C_6)$-cycloalkyl-$(C_1-C_6)$-alkyl, cyano-$(C_1-C_6)$-alkyl, each of which is substituted by n halogen atoms, or phenyl or benzyl, each of which is substituted by n radicals from the group consisting of halogen, $(C_1-C_6)$-alkyl and $(C_1-C_6)$-alkoxy, $R^3$ represents hydroxy, O—C(=O)$R^7$, O—C(=L)M$R^8$, O—SO$_2R^9$, O—P(=L)$R^{10}R^{11}$, O—C(=L)N$R^{12}R^{13}$, O-E or O—$R^{14}$, $R^4$ represents $R^{4a}$ or $R^{4b}$, $R^{4a}$ represents phenyl which is substituted by one, two or three radicals $R^5$ and one radical $R^6$, $R^{4b}$ represents 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-1-yl, 1,2,4-triazol-3-yl, 1,2,4-triazol-4-yl, 1,2,4-triazol-5-yl, 1,2,3-triazol-1-yl, 1,2,3-triazol-2-yl, 1,2,3-triazol-4-yl, tetrazol-1-yl, tetrazol-2-yl, tetrazol-5-yl, indol-1-yl, indol-2-yl, indol-3-yl, isoindol-1-yl, isoindol-2-yl, benzofur-2-yl, benzothiophen-2-yl, benzofur-3-yl, benzothiophen-3-yl, benzoxazol-2-yl, benzothiazol-2-yl, benzimidazol-2-yl, indazol-1-yl, indazol-2-yl, indazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl or 1,2,4-triazin-6-yl, substituted by one or two radicals $R^5$ and by m radicals $R^6$, $R^5$ represents hydrogen, halogen, $(C_1-C_6)$-alkyl, $(C_2-C_6)$-alkenyl, $(C_2-C_6)$-alkynyl, $(C_1-C_6)$-alkoxy, $(C_3-C_6)$-cycloalkyl or $(C_1-C_6)$-alkoxy-$(C_1-C_6)$-alkyl, each of which is substituted by n halogen atoms, $R^6$ represents phenyl substituted by n radicals $R^5$ or heteroaryl substituted by one, two or three radicals $R^5$, E represents a metal ion equivalent or an ammonium ion, L represents oxygen or sulfur, M represents oxygen or sulfur, $R^7$ represents $(C_1-C_6)$-alkyl, $(C_2-C_6)$-alkenyl, $(C_1-C_6)$-alkoxy-$(C_1-C_6)$-alkyl, di-$(C_1-C_6)$-alkoxy-$(C_1-C_6)$-alkyl or $(C_1-C_6)$-alkylthio-$(C_1-C_6)$-alkyl, each of which is substituted by n halogen atoms, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, $(C_1-C_6)$-alkyl and $(C_1-C_6)$-alkoxy, or $(C_3-C_6)$-cycloalkyl, phenyl, phenyl-$(C_1-C_6)$-alkyl, phenoxy-$(C_1-C_6)$-alkyl or heteroaryloxy-$(C_1-C_6)$-alkyl, each of which is substituted by n radicals from the group consisting of halogen, $(C_1-C_6)$-alkyl and $(C_1-C_6)$-alkoxy, $R^8$ represents $(C_1-C_6)$-alkyl, $(C_2-C_6)$-alkenyl, $(C_1-C_6)$-alkoxy-$(C_1-C_6)$-alkyl or di-$(C_1-C_6)$-alkoxy-$(C_1-C_6)$-alkyl, each of which is substituted by n halogen atoms, or $(C_3-C_6)$-cycloalkyl, phenyl or benzyl, each of which is substituted by n radicals from the group consisting of halogen, $(C_1-C_6)$-alkyl and $(C_1-C_6)$-alkoxy, $R^9$, $R^{10}$, $R^{11}$ independently of one another represent $(C_1-C_6)$-alkyl, $(C_1-C_6)$-alkoxy, N—$(C_1-C_6)$-alkylamino, N,N-di-$(C_1-C_6)$-alkylamino, $(C_1-C_6)$-alkylthio, $(C_2-C_6)$-alkenyl or $(C_3-C_6)$-cycloalkylthio, each of which is substituted by n halogen atoms, or phenyl, benzyl, phenoxy or phenylthio, each of which is substituted by n radicals from the group consisting of halogen, $(C_1-C_6)$-alkyl and $(C_1-C_6)$-alkoxy, $R^{12}$, $R^{13}$ independently of one another each represent hydrogen, $(C_1-C_6)$-alkyl, $(C_3-C_6)$-cycloalkyl, $(C_2-C_6)$-alkenyl, $(C_1-C_6)$-alkoxy or $(C_1-C_6)$-alkoxy-$(C_1-C_6)$-alkyl, substituted by n halogen atoms, phenyl or benzyl, each of which is substituted by n radicals from the group consisting of halogen, $(C_1-C_6)$-alkyl and $(C_1-C_6)$-alkoxy, or $R^{12}$ and $R^{13}$ together with the nitrogen atom to which they are attached form a 3- to 6-membered ring containing 2 to 5 carbon atoms and in each case 0 or 1 oxygen or sulfur atoms, $R^{14}$ represents $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_1-C_6)$-alkylthio-$(C_1-C_6)$-alkyl or di-$(C_1-C_6)$-alkoxy-$(C_1-C_6)$-alkyl, each of which is substituted by n halogen atoms, $(C_3-C_6)$-cycloalkyl substituted by n radicals from the group consisting of halogen, $(C_1-C_6)$-alkyl and $(C_1-C_6)$-alkoxy, a fully saturated 3- to 6-membered ring consisting of 3 to 5 carbon atoms and 1 to 3 heteroatoms from the group consisting of oxygen, sulfur and nitrogen, which ring is substituted by n radicals from the group consisting of halogen, $(C_1-C_6)$-alkyl and $(C_1-C_6)$-alkoxy, phenyl, phenyl-$(C_1-C_6)$-alkyl, heteroaryl, phenoxy-$(C_1-C_6)$-alkyl or heteroaryloxy-$(C_1-C_6)$-alkyl, substituted by n radicals from the group consisting of halogen, $(C_1-C_6)$-alkyl and $(C_1-C_6)$-alkoxy, m represents 0 or 1, n represents 0, 1, 2 or 3, s represents 0, 1, 2, 3 or 4.

3. A herbicidal composition, comprising a herbicidally active content of at least one compound of the formula (I) as claimed in claim 1.

4. The herbicidal composition as claimed in claim 3 in a mixture with formulation auxiliaries.

5. The herbicidal composition as claimed in claim 3, comprising at least one further pesticidally active substance selected from the group consisting of insecticides, acaricides, herbicides, fungicides, safeners and growth regulators.

6. The herbicidal composition as claimed in claim 5, comprising a safener.

7. The herbicidal composition as claimed in claim 6, comprising cyprosulfamide, cloquintocet-mexyl, mefenpyr-diethyl or isoxadifen-ethyl.

8. The herbicidal composition as claimed in claim 5, comprising a further herbicide.

9. A method for controlling unwanted plants, comprising applying an effective amount of at least one compound of formula (I) as claimed in claim 1 to plants and/or to a site of unwanted plant growth.

10. A compound of formula (I) as claimed in claim 1 capable of being used for controlling unwanted plants.

11. The compound as claimed in claim 10, wherein the compound of formula (I) is capable of being used for controlling unwanted plants in crops of useful plants.

12. The compound as claimed in claim 11, wherein the useful plants are transgenic useful plants.

13. An insecticidal composition, comprising an insecticidally effective amount of at least one compound of formula (I) as claimed in claim 1.

14. The insecticidal composition as claimed in claim 13 in a mixture with one or more formulation auxiliaries.

15. The insecticidal composition as claimed in claim 13, comprising at least one further pesticidally active substance selected from the group consisting of insecticides, acaricides, herbicides, fungicides, safeners and growth regulators.

16. A method for controlling unwanted insects, comprising applying an effective amount of at least one compound of formula (I) as claimed in claim 1 to one or more plants and/or to one or more insects.

17. A compound of formula (I) as claimed in claim 1 capable of being used for controlling unwanted insects.

* * * * *